＊ ＊ ＊ ＊ ＊

(12) United States Patent
Lentzsch

(10) Patent No.: US 11,382,974 B2
(45) Date of Patent: Jul. 12, 2022

(54) METHODS AND COMPOSITIONS FOR TREATMENT OF AMYLOID DEPOSITION DISEASES

(71) Applicant: The Trustees of Columbia University in the City of New York, New York, NY (US)

(72) Inventor: Suzanne Lentzsch, Bronx, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/021,168

(22) Filed: Jun. 28, 2018

(65) Prior Publication Data
US 2019/0038745 A1 Feb. 7, 2019

Related U.S. Application Data

(60) Provisional application No. 62/637,609, filed on Mar. 2, 2018, provisional application No. 62/539,821, filed on Aug. 1, 2017.

(51) Int. Cl.
*A61K 39/395* (2006.01)
*C07K 16/18* (2006.01)
*A61K 39/00* (2006.01)
*A61P 43/00* (2006.01)

(52) U.S. Cl.
CPC .... *A61K 39/3955* (2013.01); *A61K 39/39541* (2013.01); *A61P 43/00* (2018.01); *C07K 16/18* (2013.01); *A61K 2039/545* (2013.01); *A61K 2039/55* (2013.01); *A61K 2039/57* (2013.01); *A61K 2039/58* (2013.01)

(58) Field of Classification Search
CPC .......... A61K 39/3955; A61K 39/39541; A61K 2039/545; A61K 2039/55; A61K 2039/57; A61K 2039/58; A61P 43/00; C07K 16/18; C07K 2317/24
See application file for complete search history.

(56) References Cited

U.S. PATENT DOCUMENTS

| | | | |
|---|---|---|---|
| 7,256,273 B2 | 8/2007 | Basi et al. | |
| 7,927,594 B2 | 4/2011 | Rosenthal et al. | |
| 8,105,594 B2 | 1/2012 | Solomon et al. | |
| 8,195,594 B1 | 6/2012 | Bryce | |
| 8,404,815 B2 | 3/2013 | Schenk et al. | |
| 8,591,894 B2 | 11/2013 | Holtzman et al. | |
| 2009/0297439 A1 | 12/2009 | Comoglio et al. | |
| 2010/0150906 A1 | 6/2010 | Pfeifer et al. | |
| 2010/0322932 A1 | 12/2010 | Solomon et al. | |
| 2011/0177066 A1* | 7/2011 | Schenk | A61K 39/0007 424/133.1 |
| 2013/0295082 A1* | 11/2013 | Garidel | A61K 39/3955 424/133.1 |
| 2016/0024197 A1 | 1/2016 | Burbidge et al. | |
| 2016/0243230 A1 | 8/2016 | Wall et al. | |
| 2016/0264637 A1 | 9/2016 | Romeuf et al. | |

FOREIGN PATENT DOCUMENTS

| | | | |
|---|---|---|---|
| EP | 2730659 A2 | 5/2014 | |
| JP | 2009-530374 A | 8/2009 | |
| KR | 20150002879 A | 1/2015 | |
| RU | 2475500 C2 | 2/2013 | |
| WO | 9960024 A1 | 11/1999 | |
| WO | 1999060024 A1 | 11/1999 | |
| WO | 2007108756 A1 | 9/2007 | |
| WO | 2016187546 A1 | 11/2016 | |
| WO | 2017184973 A1 | 10/2017 | |
| WO | 2019006062 A1 | 1/2019 | |
| WO | WO-2019006062 A1 * | 1/2019 | ............. A61P 25/28 |

OTHER PUBLICATIONS

Comenzo RL et al. Managing systemic light-chain amyloidosis. J. National Comprehensive Cancer Network, 2007, 5, 179-187. (Year: 2007).*
Lin CY et al. Toxic human islet amyloid polypeptide (h-IAPP) oligomers are intracellular, and vaccination to induce anti-toxic oligomer antibodies does not prevent h-IAPP-induced beta-cell apoptosis in h-IAPP transgenic mice. Diabetes, 2007, 56, 1324-1332. (Year: 2007).*
Study of Chimeric Fibril-Reactive Monoclonal Antibody 11-1F4 in Patients with AL Amyloidosis, ClinicalTrials.gov, Identifier: NCT02245867, first posted Sep. 22, 2014, retrieved from internet Dec. 9, 2019. (Year: 2014).*
Lentzsch, Suzanne. Phase 1a/1b study of 11-1F4 mAb for the treatment of AL amyloidosis, 2015 NIH Grant# 1R01FD005110-01, retrieved from Grantome.com on Dec. 9, 2019. (Year: 2019).*
Langer AL et al. Results of phase I study of chimeric fibril-reactive monoclonal antibody 11-1F4 in patients with AL amyloidosis. Blood, 2015, 126(23), 188, Meeting abstract 653. (Year: 2015).*
Guidance for Industry: Estimating the maximum safe starting dose in initial clinical trials for therapeutics in adult healthy volunteers. US Dept. of Health and Human Service, Food and Drug Administration (FDA), Center for Drug Evaluation and Research (CDER), Jul. 2005, 30 pages. (Year: 2005).*
Buss SJ et al. Longitudinal left ventricular function for prediction of survival in systemic light-chain amyloidosis. J. Amer. College Cardiology, 2012, 60(12), 1067-76. (Year: 2012).*

(Continued)

*Primary Examiner* — Kimberly Ballard
(74) *Attorney, Agent, or Firm* — McCormick, Paulding & Huber PLLC

(57) ABSTRACT

Methods and pharmaceutical compositions for treatment of amyloid deposition diseases using chimeric (e.g., mouse-human) antibody are disclosed, including a method for treating amyloid deposition diseases with cardiac involvement by administering pharmaceutical compositions comprising a chimeric anti-amyloid fibril antibody. The methods herein can improve myocardial function in patients diagnosed with light chain amyloid light chain amyloidosis (ALA) having a cardiac involvement in as little as three weeks after treatment.

88 Claims, 17 Drawing Sheets
Specification includes a Sequence Listing.

(56) References Cited

OTHER PUBLICATIONS

Van Doren et al. Nonchemotherapy treatment of immunoglobulin light chain amyloidosis. Acta Haematol. 2020, 143:373-380. (Year: 2020).*

Lavatelli F et al. Biochemical markers in early diagnosis and management of systemic amyloidoses. Clin. Chem. Lab Med. 2014, 52(11):1517-1531. (Year: 2014).*

Merlini G. AL amyloidosis: from molecular mechanisms to targeted therapies. Hematology, Am Soc Hematol Educ Program, 2017 Dec. 8, 2017(1): 1-12. (Year: 2017).*

Edwards et al. "Analysis of the Phase 1 a/b Study of Chimeric Fibril-Reactive Monoclonal Antibody 11-1 F4 in Patients with AL Amyloidosis," Blood, Dec. 1, 2016 (Dec. 1, 2016), vol. 128, No. 22, p. 643. entire document.

Edwards et al. "Final Analysis of the Phase 1 a/b Study of Fibril-Reactive Monoclonal Antibody 11-1 F4 (CAEL-101) in Patients with AL Amyloidosis," Columbia University Medical Center, Dec. 10, 2017 (Dec. 10, 2017), pp. 1-24. Retrieved from the Internet: www.caelumbio.com/wp-content/uploads/2017/02/11-1 F4-ASH-Presentation-2017-12-Dec2017.pdf> on Nov. 28, 2018 (Nov. 11, 2018). entire document.

Pun et al. "Prognostic and Added Value of Two-Dimensional Global Longitudinal Strain for Prediction of Survival in Patients with Light Chain Amyloidosis Undergoing Autologous Hematopoietic Cell Transplantation," Journal of the American Society of Echocardiography, Oct. 27, 2017 (Oct. 27, 2017), vol. 31, Iss. 1, pp. 64-70. entire document.

Solomon et al. "Therapeutic Potential of Chimeric Amyloid-reactive Monoclonal Antibody 11-1F4," Clinical Cancer Research, Sep. 1, 2003 (Sep. 1, 2003), vol. 9, Iss. 10, pp. 3831s-3838s. entire document.

Leng et al. "958: Improvement in Global Longitudinal Strain (GLS) Correlates with NT-Probnp Response in Patients with Cardiac Amyloidosis Treated on a Phase 1 b Study of Anti-Amyloid Mab Cael-101," 2018 ASH Annual Meeting, San Diego Convention Center, Nov. 2, 2018 (Nov. 2, 2018), pp. 1-3. Retrieved from the Internet: ash.confex.com/ash/2018/webprogram/Paper118464.html> on Nov. 28, 2018 (Nov. 28, 2018). entire document.

International Search Report dated Sep. 24, 2018 for PCT Application No. PCT/US2018/039905.

International Search Report dated Dec. 26, 2018 for PCT Application No. PCT/US2018/043374.

Merlini G. et al., Molecular mechanisms of amyloidosis, N. Engl. J. Med., 2003, vol. 349, Issue 6, pp. 583-596.

Tuzovic M. et al., Cardiac Amyloidosis: Diagnosis and Treatment Strategies, Curr Oncol Rep., 2017, vol. 19, Issue 7, p. 46.

Riechmann L. et al., Reshaping human antibodies for therapy, Nature, 1988, vol. 332, Issue 6162, pp. 323-327.

Vajdos F.F. et al., Comprehensive Functional Maps of the Antigenbinding Site of an Anti-ErbB2 Antibody Obtained with Shotgun Scanning Mutagenesis, J. Mol. Biol., 2002, vol. 320, pp. 415-428.

De Pascalis R. et al., Grafting of "abbreviated" complementarity-determining regions containing specificity-determining residues essential for ligand contact to engineer a less immunogenic humanized monoclonal antibody, J Immunol., 2002, vol. 169, Issue 6, pp. 3076-3084.

Desport, E., et al. "AL-AMYLOIDOSIS" pp. 36-50 , (2014).

Russian Search Report for corresponding Russian Applcation No. 2020108100 dated Oct. 7, 2020.

Australian Examination Report for corresponding Australian Application No. 2018290898 dated Nov. 12, 2020.

Wall, Jonathan, "Radioimmunodetection of amyloid deposits in patients with AL amyloidosis", Blood, 2010, vol. 116, No. 13, pp. 2241-2244.

Japanese Office Action dated Dec. 15, 2020 for corresponding Japanese Application No. 2019-572403.

Japanese Office Action for corresponding Japanese Application No. 2020-505320 dated Apr. 27, 2021.

Edwards C. V. et al. Interim analysis of the phase 1a/b study of chimeric fibril-reactive monoclonal antibody 11-1F4 in patients with AL amyloidosis // Amyloid.—2017.—V. 24.—No. sup1.—p. 58-59. [Найдено Jun. 3, 2020], URL: www.tandfonline.com/doi/abs/10.1080/13506129.2017.1292900.

Examination Report in corresponding Australian Application No. 2018311688 dated Feb. 16, 2021.

Extended European Search Report dated Apr. 23, 2021 for corresponding European Application No. 18 840 642.5.

Columbian Office Action and its English translation dated Dec. 6, 2021 for corresponding Columbian Application No. 20200000260.

Endocardium,Wikipedia entry retrieved Mar. 11, 2022, en.wikipedia.org/wiki/Endocardium2, pages. (Year: 2022).

Indian First Examination Report and its English translation dated Mar. 28, 2022 for corresponding Indian Application No. 201947053227.

\* cited by examiner

Figure 2

```
         10                  30                  50
caggtgcagctgaaggagtcaggacctggcctggtggcgccctcacagagcctgtccatc
---------+---------+---------+---------+---------+---------+
gtccacgtcgacttcctcagtcctggaccggaccaccgcgggagtgtctcggacaggtag
 Q  V  Q  L  K  E  S  G  P  G  L  V  A  P  S  Q  S  L  S  I 70                  90                 110
                                  -----CDR1------
acatgcactgtctcagggttctcattaagcagctatggtgtaagctgggttcgccagcct
---------+---------+---------+---------+---------+---------+
tgtacgtgacagagtcccaagagtaattcgtcgataccacattcgacccaagcggtcgga
 T  C  T  V  S  G  F  S  L  S  S  Y  G  V  S  W  V  R  Q  P 130                 150                 170
                                ------------------------------
ccaggaaagggtctggagtggctgggagtaatatggggtgacgggagcacaaattatcat
---------+---------+---------+---------+---------+---------+
ggtcctttcccagacctcaccgaccctcattataccccactgccctcgtgtttaatagta
 P  G  K  G  L  E  W  L  G  V  I  W  G  D  G  S  T  N  Y  H 190                 210                 230
------CDR2-------------------
ccaaatctcatgtccagactgagtatcagcaaggatatttccaagagccaagttctcttc
---------+---------+---------+---------+---------+---------+
ggtttagagtacaggtctgactcatagtcgttcctataaaggttctcggttcaagagaag
 P  N  L  M  S  R  L  S  I  S  K  D  I  S  K  S  Q  V  L  F 250                 270                 290
                                                  --CDR3---
aaactgaatagtctgcaaactgatgacacagccacgtactactgtgtcaccttggactac
---------+---------+---------+---------+---------+---------+
tttgacttatcagacgtttgactactgtgtcggtgcatgatgacacagtggaacctgatg
 K  L  N  S  L  Q  T  D  D  T  A  T  Y  Y  C  V  T  L  D  Y 310                 330
tggggtcaaggaacctcagtcaccgtctcctca
---------+---------+---------+---
accccagttccttggagtcagtggcagaggagt
 W  G  Q  G  T  S  V  T  V  S  S
```

Figure 3

```
              10                  30                  50
      gatgttgtgatgacccaaactccactctccctgcctgtcagtcttggagatcaagcctcc
      ------------+---------+---------+---------+---------+---------+
      ctacaacactactgggtttgaggtgagagggacggacagtcagaacctctagttcggagg
       D   V   V   M   T   Q   T   P   L   S   L   P   V   S   L   G   D   Q   A   S 70                  90                 110
                            ------------------CDR1------------------
      atctcttgcagatctagtcagagccttgtacatagaaatggaaacacctatttacattgg
      ------------+---------+---------+---------+---------+---------+
      tagagaacgtctagatcagtctcggaacatgtatctttaccttTgtggataaatgtaacc
       I   S   C   R   S   S   Q   S   L   V   H   R   N   G   N   T   Y   L   H   W 130                 150                 170
                                                  --------CDR2---
      tacctgcagaagccaggccagtctccaaagctcctgatctacaaagtttccaaccgattt
      ------------+---------+---------+---------+---------+---------+
      atggacgtcttcggtccggtcagaggtttcgaggactagatgtttcaaaggttggctaaa
       Y   L   Q   K   P   G   Q   S   P   K   L   L   I   Y   K   V   S   N   R   F 190                 210                 230
      tctggggtcccagacaggttcagtggcagtggatcagggacagatttcacactcaagatc
      ------------+---------+---------+---------+---------+---------+
      agaccccagggtctgtccaagtcaccgtcacctagtccctgtctaaagtgtgagttctag
       S   G   V   P   D   R   F   S   G   S   G   S   G   T   D   F   T   L   K   I 250                 270                 290
                                              ------------CDR3---
      agcagagtggaggctgaggatttgggactttatttctgttttcaaactacatatgttccg
      ------------+---------+---------+---------+---------+---------+
      tcgtctcacctccgactcctaaacccTgaaataaagacaaaagtttgatgtatacaaggc
       S   R   V   E   A   E   D   L   G   L   Y   F   C   F   Q   T   T   Y   V   P 310                 330
      aacacgttcggaggggggaccaagctggaaataaaa
      ------------+---------+---------+------
      ttgtgcaagcctccccctggttcgacctttatttt
       N   T   F   G   G   G   T   K   L   E   I   K
```

5'-aagcttgccgccaccatgaagttgcctgttaggctgttggtgc-3'

HindIII Kozak                    Leader
aagcttgccgccaccatgaagttgcctgttaggctgttggtgctgatgttctggattcctgcttccagcagt
ttcgaacggcggtggtacttcaacggacaatccgacaaccacgactacaagacctaaggacgaaggtcgtca
      M  K  L  P  V  R  L  L  V  L  M  F  W  I  P  A  S  S  S 10               30                50
gatgttgtgatgacccaaactccactctccctgcctgtcagtcttggagatcaagcctcc
ctacaacactactgggtttgaggtgagagggacggacagtcagaacctctagttcggagg
 D  V  V  M  T  Q  T  P  L  S  L  P  V  S  L  G  D  Q  A  S 70               90               110
                              ---------------CDR1-----------------
atctcttgcagatctagtcagagccttgtacatagaaatggaaacacctatttacattgg
tagagaacgtctagatcagtctcggaacatgtatctttacctttgtggataaatgtaacc
 I  S  C  R  S  S  Q  S  L  V  H  R  N  G  N  T  Y  L  H  W 130              150              170
                                               ----------CDR2---
tacctgcagaagccaggccagtctccaaagctcctgatctacaaagtttccaaccgattt
atggacgtcttcggtccggtcagaggtttcgaggactagatgtttcaaaggttggctaaa
 Y  L  Q  K  P  G  Q  S  P  K  L  L  I  Y  K  V  S  N  R  F 190              210              230
tctggggtcccagacaggttcagtggcagtggatcagggacagatttcacactcaagatc
agaccccagggtctgtccaagtcaccgtcacctagtccctgtctaaagtgtgagttctag
 S  G  V  P  D  R  F  S  G  S  G  S  G  T  D  F  T  L  K  I 250              270              290
                                         --------------CDR3---
agcagagtggaggctgaggatttgggactttatttctgttttcaaactacatatgttccg
tcgtctcacctccgactcctaaaccctgaaataaagacaaaagtttgatgtatacaaggc
 S  R  V  E  A  E  D  L  G  L  Y  F  C  F  Q  T  T  Y  V  P 310              330
------                                          BamHI
aacacgttcggagggggggaccaagctggaaatcaaacgtgagtggatcc
ttgtgcaagcctccccctggttcgacctttagtttgcactcacctagg
 N  T  F  G  G  G  T  K  L  E  I  K 3'-agcctccccctggttcgacctttagtttgcactcacctagg-5'

5'-aagctttccgccaccatggctgtcctggggctgctcttctgc-3'

HindIII Kozak                    Leader
aagcttgccgccaccatggctgtcctggggctgctcttctgcctggtgacattcccaagctgtgtcctgtcc
ttcgaacggcggtggtaccgacaggaccccgacgagaagacggaccactgtaagggttcgacacaggacagg
      M  A  V  L  G  L  L  F  C  L  V  T  F  P  S  C  V  L  S
              10              30              50 caggtgcagctgaaggagtcaggacctggcctggtggcgcctcacagagcctgtccatc
gtccacgtcgacttcctcagtcctggaccggaccaccgcgggagtgtctcggacaggtag
   Q  V  Q  L  K  E  S  G  P  G  L  V  A  P  S  Q  S  L  S  I
              70              90              110
                                    ------CDR1------
acatgcactgtctcagggttctcattaagcagctatggtgtaagctgggttcgccagcct
tgtacgtgacagagtcccaagagtaattcgtcgataccacattcgacccaagcggtcgga
   T  C  T  V  S  G  F  S  L  S  S  Y  G  V  S  W  V  R  Q  P
              130             150             170
                                                    ---------
ccaggaaagggtctggagtggctgggagtaatatggggtgacgggagcaccaattatcat
ggtcctttcccagacctcaccgaccctcattataccccactgccctcgtgttaatagta
   P  G  K  G  L  E  W  L  G  V  I  W  G  D  G  S  T  N  Y  H
              190             210             230
   ------CDR2----------------------
ccaaatctcatgtccagactgagtatcagcaaggatatttccaagagccaagttctcttc
ggtttagagtacaggtctgactcatagtcgttcctataaaggttctcggttcaagagaag
   P  N  L  M  S  R  L  S  I  S  K  D  I  S  K  S  Q  V  L  F
              250             270             290
                                                    --CDR3---
aaactgaatagtctgcaaactgatgacacagccacgtactactgtgtcaccttggactac
tttgacttatcagacgtttgactactgtgtcggtgcatgatgacacagtggaacctgatg
   K  L  N  S  L  Q  T  D  D  T  A  T  Y  Y  C  V  T  L  D  Y
              310             330
                                        ----------CH1---------→
tggggtcaaggaacctcagtcaccgtctcctcagcctccaccaagggcccatcgg
accccagttccttggagtcagtggcagaggagtcggaggtggttcccgggtagcc
   W  G  Q  G  T  S  V  T  V  S  S
                                                    ApaI 3'-ccttggagtcagtggcagaggagtcggaggtggttcccgggtagcc-5'

Figure 9
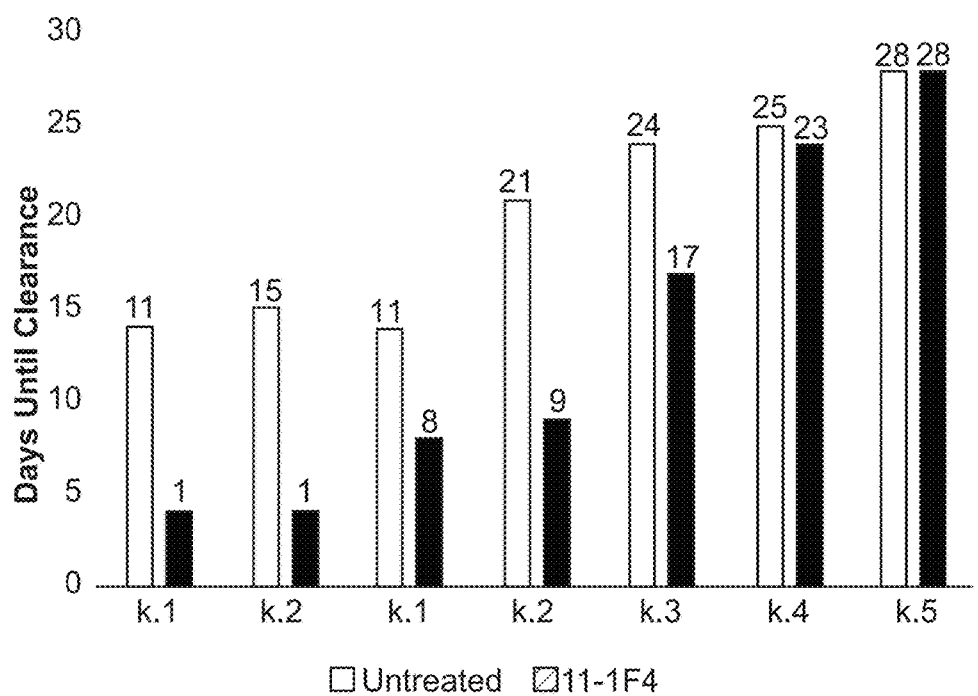
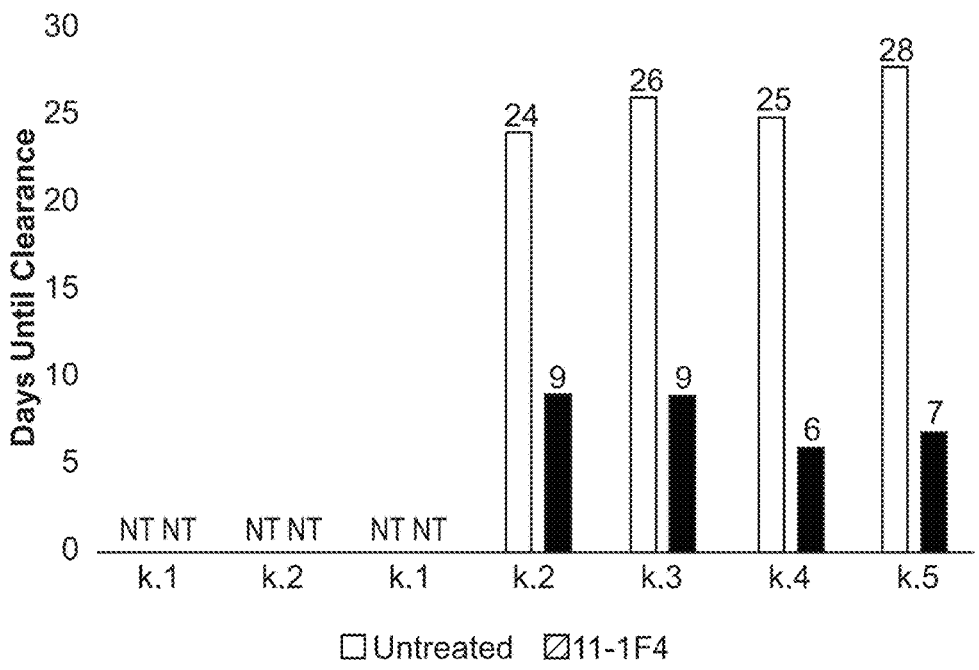
Notes: Days until clearance of untreated vs 11-1F4 treated human amiodarona deposits injected subcutaneously into mice
1 100μg al day 0 2 100 μg al days 0,2,4,6  11-1F4 are mAb designation

Figure 10
A.
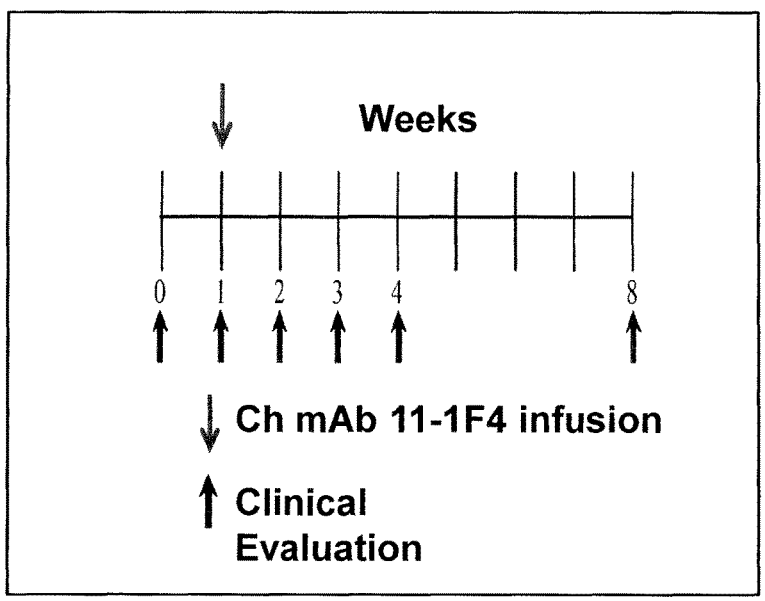
B.
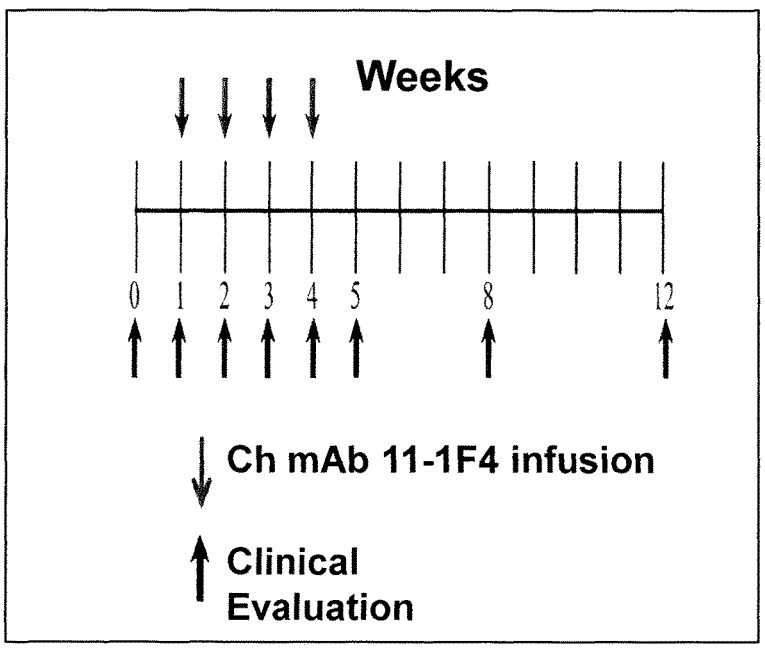
C.
| Level | Dose (mg/m²) |
|---|---|
| -2 | 0.125 |
| -1 | 0.25 |
| 1 | 0.5* |
| 2 | 5 |
| 3 | 10 |
| 4 | 50 |
| 5 | 100 |
| 6 | 250 |
| 7 | 500 |

PATIENT PROFILE:

Refractory λ AL Amyloidosis

Baseline NT-proBNP in ng/L
approx. 13,000

Previous treatments
1

Best Hematologic response to chemotherapy
VGPR

Organ response to chemotherapy
No organ response
Persistently elevated NT-proBNP
NYHA Class III

Organ response to 11-1F4
NYHA Class I
NT-proBNP

Figure 13
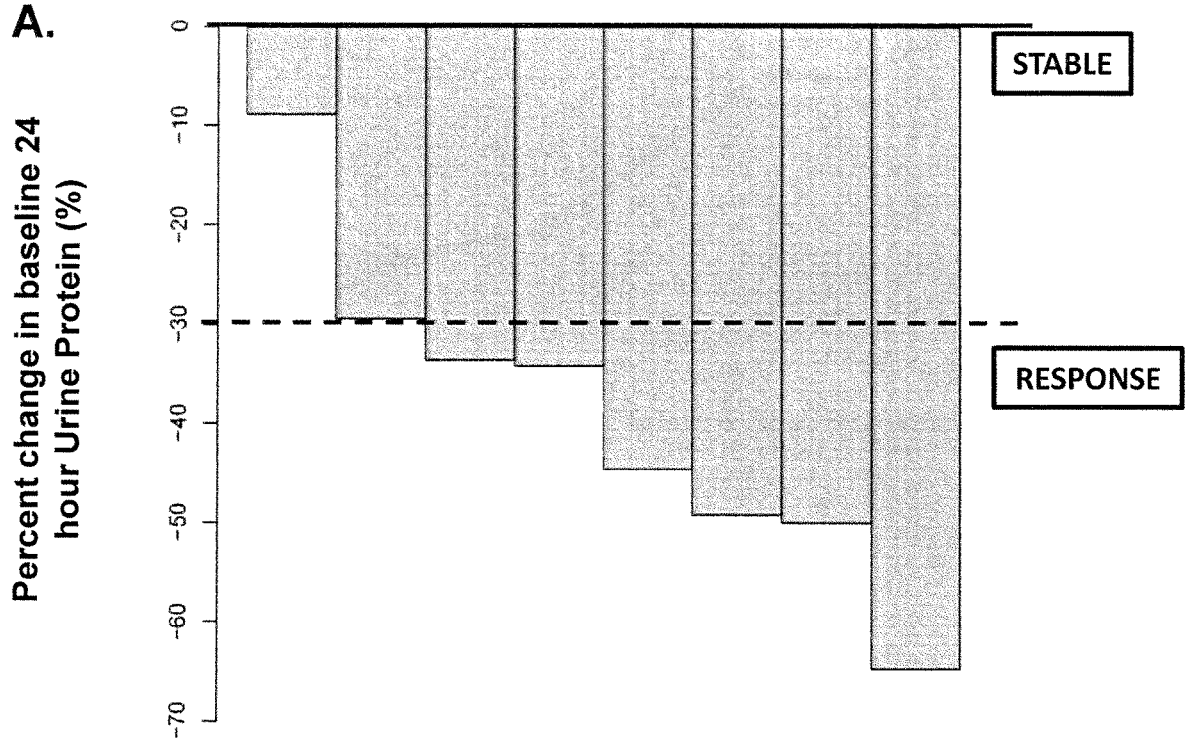
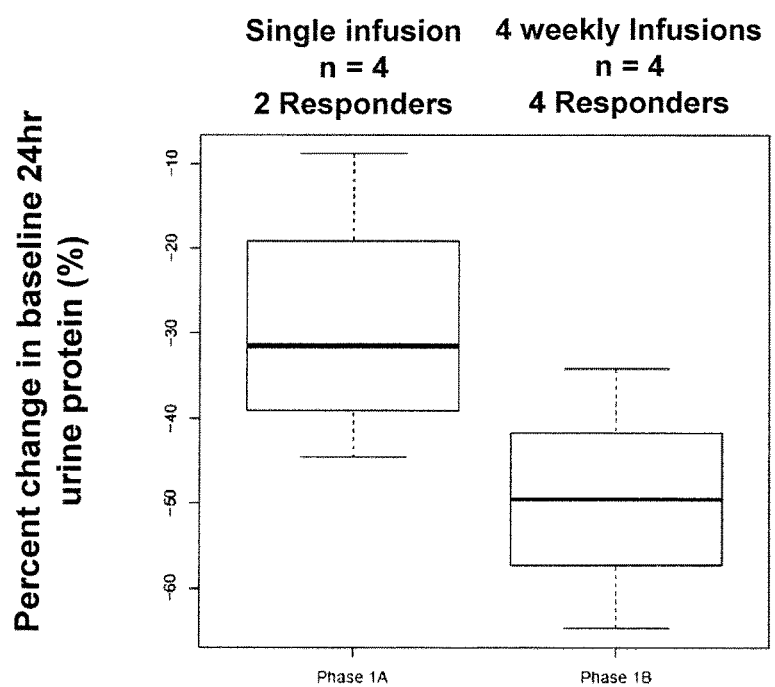

24 hour urine protein in a patient before and during Phase 1a/b clinical trial of 11-1F4 antibody

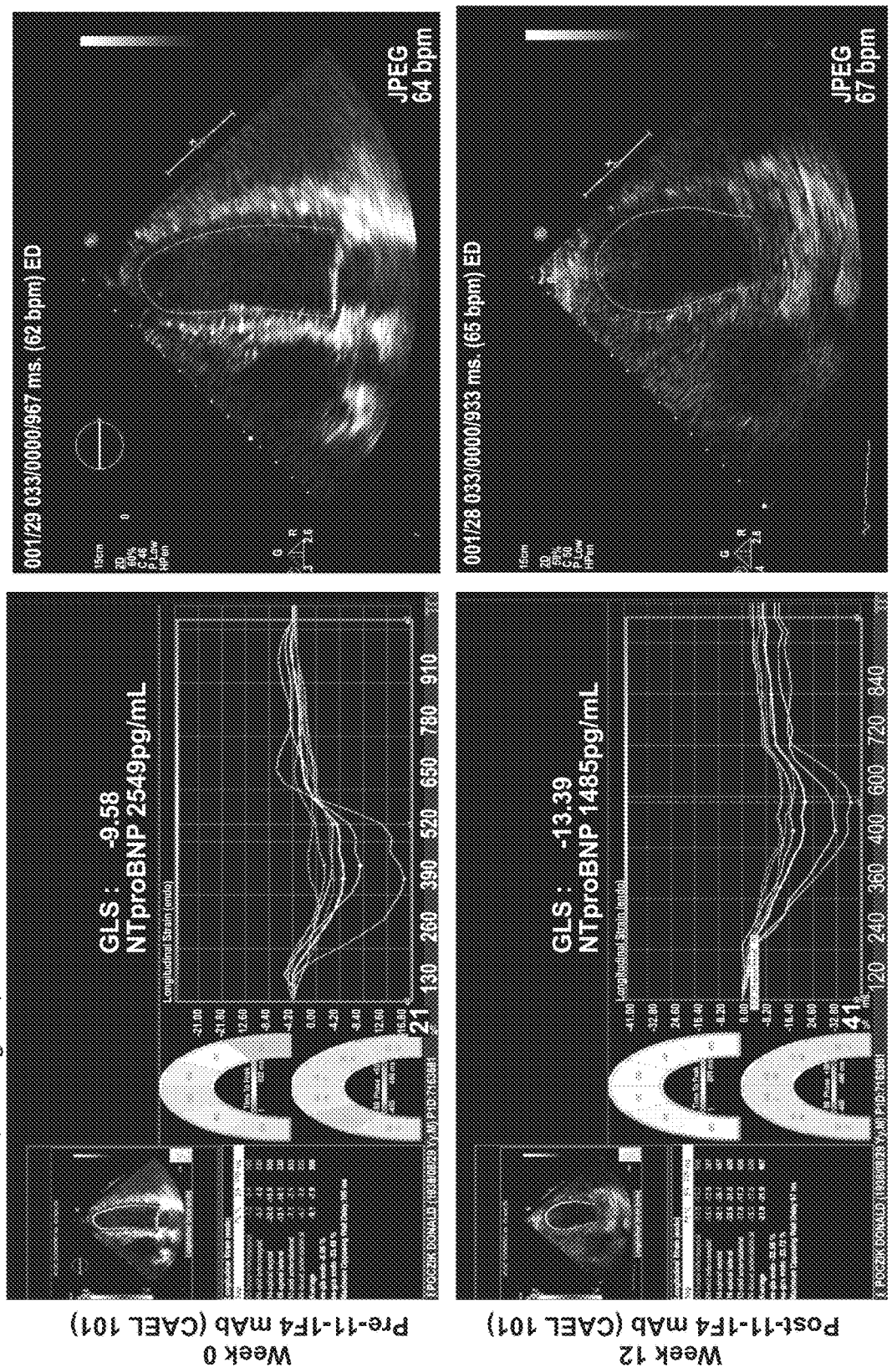

METHODS AND COMPOSITIONS FOR TREATMENT OF AMYLOID DEPOSITION DISEASES

CLAIM FOR PRIORITY

This application claims priority from U.S. provisional patent applications 62/539,821, filed Aug. 1, 2017, and 62/637,609, filed Mar. 2, 2018, which applications are incorporated herein in their entirety.

GOVERNMENT RIGHTS

This invention was made with United States government support under grant FD-U-005110, awarded by the Food and Drug Administration. Thus, the United States government may have certain rights to the invention described and claimed herein.

REFERENCE TO A SEQUENCE LISTING SUBMITTED BY EFS-WEB

The contents of the ASCII file of the sequence listing named "8441-0009-1(rev)-ST25", which is 17.3 kb in size, was created on Apr. 11, 2020, and was electronically submitted vis EFS-Web on Apr. 16, 2020 is incorporated herein by reference in its entirety.

FIELD OF THE INVENTION

The present disclosure relates to humanized and chimeric (e.g., mouse-human) antibodies and antigen-binding fragments thereof useful to treat amyloid deposition diseases, particularly primary (AL) amyloidosis, pharmaceutical compositions comprising such antibodies, and methods of treating amyloid deposition diseases using said antibodies and pharmaceutical compositions. The disclosure additionally relates to methods of treating amyloid deposition diseases with amyloid fibril-reactive antibodies. In particular, the present disclosure relates to methods of improving myocardial function in patients diagnosed with amyloid light chain amyloidosis (ALA) that includes cardiac involvement (i.e., amyloid deposition in or around the heart). Such patients may have ALA deposits comprising light chain lambda amyloid or light chain kappa amyloid. Moreover, the patients may have a disease that is hematologically controlled or uncontrolled.

BACKGROUND OF THE INVENTION

The following discussion is provided merely to aid the reader in understanding the disclosure and is not admitted to describe or constitute prior art thereto.

Native antibodies are usually heterotetrameric glycoproteins of about 150,000 daltons composed of two identical light chains and two identical heavy chains. Each light chain is linked to a heavy chain by one disulfide bond, while the number of additional disulfide linkages between the heavy chains varies with different antibody isotypes. The simplest isotype is IgG, which comprises just two light chains and two heavy chains, in which the two heavy chains are linked by two disulfide linkages. Each heavy chain has a variable domain ($V_H$) at one end with a number of adjacent constant domains. Each light chain has a variable domain ($V_L$) at one end and a constant domain at its other end. Each variable domain of the light and heavy chain in an antibody comprises three segments called complementarity-determining regions ("CDR") or hypervariable regions. Each CDR in a light chain, together with the corresponding CDR in the adjacent heavy chain, form an antigen-binding site of the antibody. Light chains are of two major types, κ and λ, depending on their constant region. Both κ and λ light chains may combine with any of the different heavy chain types.

Amyloid light-chain amyloidosis (AL amyloidosis, AL, or ALA), also called primary amyloidosis, is the most common form of systemic amyloidosis in the United States. The term "amyloidosis" refers to a cluster of diseases which share a common feature, i.e., the extracellular deposition of pathologic insoluble fibrillar proteins in organs and tissues (Rodney, et al. —*NEJM,* 25:898). Amyloidosis is caused by malfunction of a person's antibody-producing cells causing production of abnormal protein fibers which aggregate to form insoluble amyloid deposits in organs and tissues. The type of amyloidosis is determined by the nature of the precursor proteins which form the fibril deposit. In primary amyloidosis, the fibrils comprise fragments of immunoglobulin light chains and in secondary amyloidosis, the fibrils comprise amyloid A protein. Modern classification of amyloidosis is based on the nature of the precursor plasma proteins which form the fibril deposit.

The precursor plasma proteins are diverse and unrelated. Nevertheless, all precursor deposits produce amyloid deposits that share a common typical β-pleated-sheet configuration, which is responsible for the typical staining properties of the fibrillar deposits. The final stage in the development of amyloidosis is the deposit of amyloid fibrils in the organs of the sufferer. Amyloidosis mortality is high, with current five-year survival rates of about 28%.

To date, the treatment of AL has been directed towards reducing the synthesis of amyloidogenic precursor light chains by attacking the malfunctioning cells through conventional or high dose cytotoxic chemotherapy. This treatment suffers from two disadvantages. First, the fibrillar deposits are often asymptomatic until after significant deposition has taken place. Therefore, treatment is unlikely to be undertaken before significant deposits have already occurred. Second, since this treatment is, at best, effective only to stop the production of precursor abnormal protein but not to remove the existing deposits, prognosis for AL patients remains exceedingly poor due to persistence (or progression) of the pathologic deposits (Solomon, et al. —*Int. J. Exp. Clin. Invest.* 2:269)

As a result, therapeutic targeting and clearance of amyloid deposits is an area of intense medical interest. However, the FDA has not approved any such therapeutic products to date, and therefore, there is still a significant unmet medical need. The compositions and methods disclosed herein fulfill this need.

SUMMARY OF THE INVENTION

Described herein are compositions and methods for treating amyloid deposition diseases, specifically primary (AL) amyloidosis. The disclosed compositions and methods employ humanized or chimeric antibodies or fragments thereof that specifically bind to amyloid fibrils (e.g., amyloid light chain fibrils) to target the fibrils for clearance by the immune system.

In one aspect, the present compositions and methods comprise humanized or chimeric antibodies (e.g., mouse-human chimeric antibodies) useful for treatment of amyloid deposition diseases, particularly primary (ALA) amyloidosis. In some embodiments, the disclosed antibody comprises a V$_K$ region comprising SEQ ID NO: 47 and a V$_H$ region comprising SEQ ID NO: 48. In some embodiments, the antibody comprises a constant region derived from a human IgG1. In some embodiments, the antibody binds to amyloid fibrils with a higher affinity than its murine equivalent. In some embodiments, the antibody binds to an epitope expressed by the β-pleated sheet configuration of amyloid fibrils with higher affinity than a mouse antibody comprising a V$_K$ region of SEQ ID NO: 36 and a V$_H$ region of SEQ ID NO: 35. And in some embodiments, the antibody binds to kappa and lambda amyloid fibrils in vivo.

In another aspect, the present disclosure provides pharmaceutical compositions comprising the disclosed humanized or chimeric antibody and a pharmaceutically acceptable carrier.

A chimeric antibody useful in the subject methods and pharmaceutical compositions may be produced by co-transfection in mammalian cells of the vector constructs 11-1F4VK.pKN100 and 11-F4VH.pG1D200 or transfection in mammalian cells of the supervector construct pG1KD200-11-1F4. In some embodiments, the co-transfection of the vector constructs 11-1F4VK.pKN100 and 11-F4VH.pG1D200 or transfection of a supervector construct pG1KD200-11-1F4 takes place in COS cells. The antibody produced is designated "chimeric 11-1F4 antibody".

In another aspect, the present disclosure provides methods for treating or ameliorating amyloid deposition diseases, such as primary (AL) amyloidosis, in a human in need of such treatment by administering to a human patient in need of such treatment or amelioration a therapeutically effective amount of at least one of the disclosed antibodies or fragments in an amount effective to treat or ameliorate the amyloid deposition disease and/or the symptoms of the disease. In some embodiments, the disclosed antibody may be administered together with a pharmaceutically acceptable carrier.

In some embodiments, the amyloid deposition disease is primary amyloidosis. In some embodiments, the antibody is administered in a dose of about 500 mg/m$^2$ or less, while in some embodiments, the effective dose of a chimeric 11-1F4 antibody is about 2,200 mg, and in some embodiments, the effective amount is about 1-50 mg/kg.

In some embodiments, the primary amyloidosis comprises involvement of at least one organ or tissue selected from the group consisting of heart, kidneys, liver, lung, gastrointestinal tract, nervous system, muscular skeletal system, soft tissue, and skin.

In some embodiments when the amyloidosis is effecting the heart, the patient's N-terminal pro b-type natriuretic peptide (NT-proBNP) level may decrease following administration of the antibody by at least about 30% or about 40% compared to baseline levels. In some embodiments, the patient's N-terminal pro b-type natriuretic peptide (NT-proBNP) level may decrease to less than about 9100, about 8000, about 7000, about 6000, or about 5000 ng/L following administration of the antibody. In some embodiments, the patient was classified as New York Heart Association (NYHA) Functional Classification class II or III prior to administration of the antibody and is classified as class I following administration of the antibody.

In some embodiments when the amyloidosis is affecting the kidneys, the patient's urine protein level may decrease by at least about 30% or about 40% compared to baseline levels following administration of the antibody. In some embodiments, the patient's urine protein may decrease to less than about 7000, about 6000, about 5000, or about 4000 mg/24 hours following administration of the antibody.

In some embodiments, administration of the antibody does not cause any serious adverse events.

The present disclosure provides methods of treating ALA with cardiac involvement. The disclosed methods are uniquely able to provide beneficial clinical results within about 3 weeks of the commencement of treatment and in a patient population that was previously considered incapable of treating due to an extremely short life expectancy.

In one aspect, the present disclosure provides methods of improving myocardial function in a patient diagnosed with amyloid light chain amyloidosis (ALA) with cardiac involvement comprising: administering to a patient diagnosed with ALA with cardiac involvement a therapeutically effective amount of a humanized or chimeric antibody or an antigen-binding fragment thereof, the antibody or antigen-binding fragment comprising: a variable heavy chain (V$_H$) comprising: a complementarity determining region (CDR) H1 comprising SEQ ID NO: 52; a CDRH2 comprising SEQ ID NO: 53; and a CDRH3 comprising SEQ ID NO: 54; and a variable light chain (V$_K$) comprising a CDRL1 comprising SEQ ID NO: 49; a CDRL2 comprising SEQ ID NO: 50; and a CDRL3 comprising SEQ ID NO: 51; thereby improving the myocardial function of the patient within about three weeks of administration of the antibody or an antigen-binding fragment thereof.

In another aspect, the present disclosure provides methods of monitoring improvement in myocardial function in a patient diagnosed with light chain amyloidosis (ALA) with cardiac involvement comprising observing an improvement in myocardial function in a patient diagnosed with ALA having a cardiac involvement within about three weeks after administration to said patient of a therapeutically effective amount of a humanized or chimeric 11-1F4 antibody or an antigen-binding fragment thereof.

In another aspect, the present disclosure provides methods of treating amyloid light chain amyloidosis (ALA) with cardiac involvement in a patient, wherein the ALA is not hematologically controlled, the method comprising administering to a patient with ALA characterized by cardiac involvement and a lack of hematological control a therapeutically effective amount of a humanized or chimeric antibody or an antigen-binding fragment thereof comprising: a variable heavy chain (V$_H$) comprising: a complementarity determining region (CDR) H1 comprising SEQ ID NO: 52; a CDRH2 comprising SEQ ID NO: 53; and a CDRH3 comprising SEQ ID NO: 54; and a variable light chain (V$_K$) comprising a CDRL1 comprising SEQ ID NO: 49; a CDRL2 comprising SEQ ID NO: 50; and a CDRL3 comprising SEQ ID NO: 51.

In some embodiments of the foregoing aspects, the antibody or antigen-binding fragment thereof may be a humanized antibody, while in some embodiments, the antibody or antigen-binding fragment thereof may be a chimeric antibody.

In some embodiments of the foregoing aspects, the V$_K$ region of the antibody or antigen-binding fragment may comprise SEQ ID NO: 47 and the V$_H$ region may comprise SEQ ID NO: 48.

In some embodiments of the foregoing aspects, the antibody or antigen-binding fragment may comprise a constant region that is derived from a human IgG1.

In some embodiments of the foregoing aspects, the methods may provide improvement in myocardial function that persists for at least three months after administration of the antibody or antigen-binding fragment thereof. In some embodiments, the improvement may persist for four, five, six, seven, eight, nine, ten, eleven, or twelve or more months.

In some embodiments of the foregoing aspects, the antibody or antigen-binding fragment thereof may be administered no more than once, twice, three, or four times within a three month period. In some embodiments, the antibody or antigen-being fragment may be administered even less, for example, once every other month or once every three months.

In some embodiments of the foregoing aspects, the methods provide an improvement in myocardial function that may comprise an improvement in global longitudinal strain (GLS) compared with pretreatment GLS level.

In some embodiments of the foregoing aspects, the patient exhibits a pretreatment NT-proBNP level greater than 650 pg/mL.

In some embodiments of the foregoing aspects, the therapeutically effective dose or amount of the antibody or antibody fragment is effective to cause a reduction in the patient's post-treatment NT-proBNP level of about 300 pg/mL or more compared to pretreatment NT-proBNP level. In some embodiments, the reduction in NT-proBNP may be about 400, about 500, about 600, about 700, about 800, about 900, or about 1000 or more pg/mL.

In some embodiments of the foregoing aspects, the methods provide an improvement in myocardial function that may comprise a reduction in post-treatment NT-proBNP level of about 30% or more compared to pretreatment NT-proBNP level.

In some embodiments of the foregoing aspects, the patient may suffer from relapse or refractory ALA.

In some embodiments of the foregoing aspects, the ALA may be further characterized as having light chain lambda amyloid cardiac involvement, while in some embodiments, the ALA may be further characterized as having light chain kappa amyloid cardiac involvement.

In some embodiments of the foregoing aspects, the ALA may not be hematologically controlled. For example, the difference between involved and uninvolved free light chains in the subject's serum may be >40 mg/L or the subject may have detectable levels of toxic amyloid precursor proteins in his or her blood or serum.

In some embodiments of the foregoing aspects, the methods may further comprise administering a chemotherapeutic compound to the patient.

In another aspect, the present disclosure provides methods of detection of an amyloid deposition disease in a patient suspected of having such disease by administering a labeled antibody or an antigen-binding fragment thereof and detecting the presence of the label in the patient. In some embodiments, the label may be a radiolabel, such as $^{124}I$, but other sorts of labels can be readily envisioned by one of skill in the art.

In another aspect, the present disclosure provides methods of treating a patient with an amyloid deposit disease comprising administering a therapeutically effective amount of a humanized or chimeric 11-1F4 antibody or an antigen-binding fragment thereof to said patient less frequently than once per month. For instance, in some embodiments, treatment may require that the patient is administered a therapeutically effective amount of the humanized or chimeric 11-1F4 antibody or antigen-binding fragment only once every two months, once every three months, once every four months, once every five months, once every six months, once every seven months, once every eight months, once every nine months, once every ten months, once every eleven months, or once a year.

In some embodiments of this aspect, the humanized or chimeric 11-1F4 antibody comprises a constant region is derived from a human IgG1.

In some embodiments of this aspect, the amyloid deposition disease is primary light chain (AL) amyloidosis, and the disease may comprise aggregates of lambda light chain fibrils. In some embodiments, the presence of aggregates of lambda light chain fibrils is significantly reduced following administration of the antibody.

In some embodiments of this aspect, the therapeutically effective amount of the humanized or chimeric 11-1F4 antibody or antigen-binding fragment is 500 mg/m$^2$ or less, while in some embodiments, the therapeutically effective amount of the humanized or chimeric 11-1F4 antibody or antigen-binding antibody fragment is about 2,200 mg, and in some embodiments, the therapeutically effective amount is about 1-50 mg/kg.

In some embodiments of this aspect, the therapeutically effective amount of the humanized or chimeric 11-1F4 mAb or antigen-binding fragment is administered once every two, three, four, five, or six months. In some embodiments, the therapeutically effective amount of the chimeric 11-1F4 mAb or antigen-binding fragment is administered biannually or only once a year.

In another aspect, the present disclosure provides methods of treating a patient with primary light chain (AL) amyloidosis involving the heart comprising administering a dose of a humanized or chimeric 11-1F4 antibody to said patient, said dose being effective to cause at least a 30% reduction in N-terminal pro b-type natriuretic peptide (NT-proBNP) level in said patient following administration of the chimeric 11-1F4 antibody compared to pre-treatment level. In some embodiments, the AL amyloidosis is refractory.

In some embodiments of this aspect, the humanized or chimeric 11-1F4 antibody comprises a constant region is derived from a human IgG1.

In some embodiments of this aspect, the humanized or chimeric 11-1F4 antibody is administered once a month, while in some embodiments, the humanized or chimeric 11-1F4 antibody is administered once a week.

In some embodiments of this aspect, the therapeutically effective amount of the humanized or chimeric 11-1F4 antibody is 500 mg/m$^2$ or less, while in some embodiments, the therapeutically effective amount of the humanized or chimeric 11-1F4 antibody is about 2,200 mg, and in some embodiments, the effective amount is about 1-50 mg/kg.

In some embodiments of this aspect, the reduction in NT-proBNP is sustained in the patient for at least about six months after the administration of the chimeric 11-1F4 antibody.

In another aspect, the present disclosure provides methods of treating a patient with primary light chain (AL) amyloidosis involving the kidneys comprising administering a dose of a humanized or chimeric 11-1F4 antibody or antigen-binding antibody fragment to said patient, said dose being effective to cause at least a 40% reduction in proteinuria in said patient following administration of the humanized or chimeric 11-1F4 antibody compared to pre-treatment level. In some embodiments, the AL amyloidosis is refractory.

In some embodiments of this aspect, the humanized or chimeric 11-1F4 antibody comprises a constant region is derived from a human IgG1.

In some embodiments of this aspect, the humanized or chimeric 11-1F4 antibody is administered once a month, while in some embodiments, the humanized or chimeric 11-1F4 antibody is administered once a week.

In some embodiments of this aspect, the therapeutically effective amount of the humanized or chimeric 11-1F4 antibody is 500 mg/m² or less, while in some embodiments, the therapeutically effective amount of the humanized or chimeric 11-1F4 antibody is about 2,200 mg, and in some embodiments, the therapeutically effective amount is about 1-50 mg/kg.

In some embodiments of this aspect, the reduction in proteinuria is sustained in the patient for at least about six months after the administration of the chimeric 11-1F4 antibody.

In another aspect, the present disclosure provides methods of decreasing the amount of kappa or lambda light chain fibril aggregate deposits in a patient in need thereof comprising, administering to said patient a dose of an antibody comprising: (a) a $V_K$ region comprising SEQ ID NO: 47, (b) a $V_H$ region comprising SEQ ID NO: 48, and (c) a human IgG1 constant region; said dose being effective to decrease the amount of kappa or lambda light chain fibril aggregate deposits in the patient.

In some embodiments of this aspect, the primary amyloidosis consists of lambda light chain fibril aggregate deposits, while in some embodiments, the primary amyloidosis consists of kappa light chain fibril aggregate deposits, and in still other embodiments, the primary amyloidosis consists of kappa and lambda light chain fibril aggregate deposits.

In some embodiments of this aspect, the humanized or chimeric 11-1F4 antibody is administered once a month, while in some embodiments, the humanized or chimeric 11-1F4 antibody is administered once a week.

In some embodiments of this aspect, the therapeutically effective amount of the humanized or chimeric 11-1F4 antibody is 500 mg/m² or less, while in some embodiments, the therapeutically effective amount of the humanized or chimeric 11-1F4 antibody is about 2,200 mg, and in some embodiments, the therapeutically effective amount is about 1-50 mg/kg.

In another aspect, the present disclosure provide methods of treating AL amyloidosis comprising administering to a patient with AL amyloidosis a monoclonal comprising the complementarity determining regions (CDRs) of an 11-1F4 antibody, wherein the antibody is not murine 11-14F.

In some embodiments of this aspect, the antibody may be a mouse-human chimeric antibody.

In some embodiments of this aspect, the antibody comprises a human IgG1 constant region.

In some embodiments of any of the foregoing methods, organ dysfunction in the patient is decreased following administration of the antibody. In some embodiments of any of the foregoing methods, the patient shows signs of a therapeutic response in less than 5 weeks after treatment, sometimes in less than 4 weeks after treatment, sometimes in less than 3 weeks after treatment, sometimes in less than 2 weeks after treatment, while in some other embodiments, the patient shows signs of a therapeutic response within about a week or less after treatment.

The foregoing general description and following detailed description are exemplary and explanatory and are intended to provide further explanation of the invention.

BRIEF DESCRIPTION OF THE DRAWINGS

FIG. 2 is a listing of DNA and amino acid sequences of the murine 11-1F4 antibody $V_H$ region gene, SEQ ID NO: 39 and NO: 35, respectively.

FIG. 3 is a listing of DNA and amino acid sequences of the murine 11-1F4 antibody $V_K$ region gene, SEQ ID NO: 40 and NO: 36, respectively.

FIG. 6 is a listing of the DNA and amino acid sequences of the modified murine 11-1F4 antibody $V_K$ region gene (SEQ ID NO: 42 and NO: 47, respectively) and the sequences of the oligonucleotide primers used to modify the $V_K$ gene (SEQ ID NO: 41 and NO: 43, respectively).

FIG. 7 is a listing of the DNA and amino acid sequences of the modified murine 11-1F4 antibody $V_H$ region gene (SEQ ID NO: 45 and NO: 48, respectively) and the sequences of the oligonucleotide primers used to modify the $V_H$ gene (SEQ ID NO: 44 and NO: 46, respectively).

FIG. 9 shows clearance of human ALκ and human ALλ amyloidomas in mice treated with murine 11-1F4. Mice were treated with either a single dose (Panel A) or multiple doses (Panel B) of murine 11-1F4. The results indicate that murine 11-1F4 quickly clears ALκ amyloidomas, but in most instances multiple doses were required to clear ALλ amyloidomas from the mice.

FIG. 10 shows the dosing/evaluation scheme of Phase 1a/b trials of chimeric 11-1F4. Panel A shows the scheme for Phase 1a and Panel B shows the scheme for Phase 1b. Panel C shows the doses that were used in these studies.

FIG. 13 shows that administration of chimeric 11-1F4 provides an improvement in renal function in most patients.

Panel A shows the results from a Phase 1a/b trial in a bar graph, and Panel B shows the results as a box plot.

Figure 14:
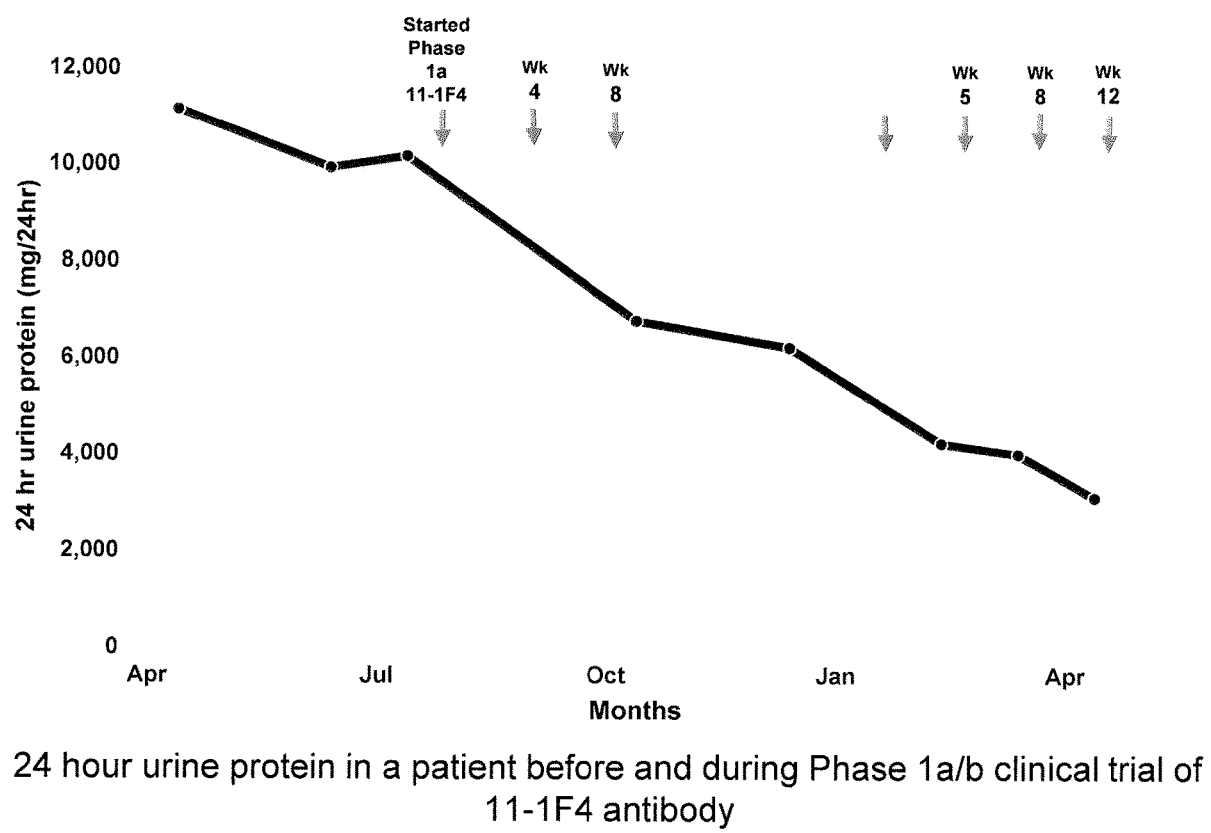

FIG. 14 shows renal response (proteinuria) in an exemplary patient during Phase 1a/b clinical trial of chimeric 11-1F4 antibody.

Figure 15:
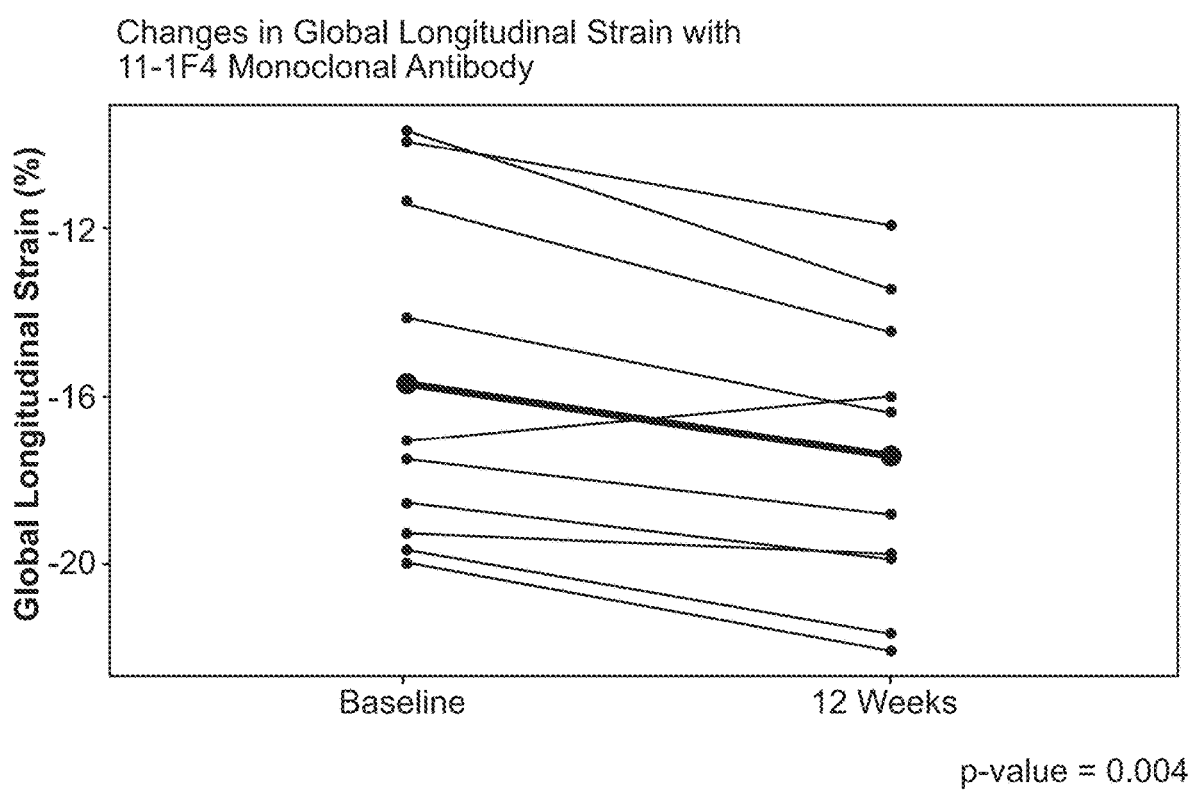

FIG. 15 shows a graphical depiction of changes in global longitudinal strain with the chimeric 11-1F4 monoclonal antibody.

Figure 16:
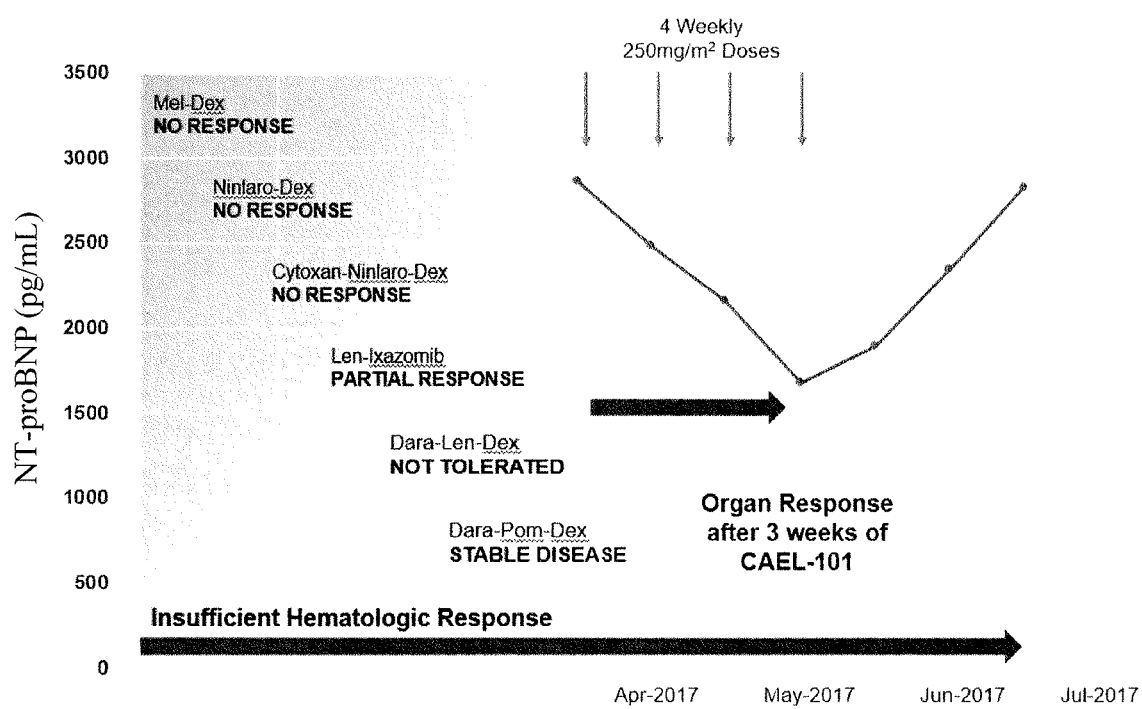

FIG. 16 shows a graphical depiction of organ response (NT-proBNP) upon chimeric 11-1F4 antibody treatment in a patient who had a partial hematological response to chemotherapy with no organ response prior to the chimeric antibody treatment.

FIG. 17 shows an echocardiogram of an amyloidosis patient with cardiac involvement at week 0 and at week 12 post chimeric 11-1F4 mAb treatment.

DETAILED DESCRIPTION OF THE INVENTION

In accordance with the present disclosure, methods and compositions comprising humanized antibodies, chimeric antibodies (e.g., mouse-human antibodies) or antigen-binding fragments thereof are provided that are useful for administration to humans suffering from amyloid deposition diseases to treat or ameliorate the disease and symptoms of the disease. The antibodies and antibody fragments of the invention bind to amyloid deposits and activate the patient's immune system to clear the bound materials while producing little or no human anti-mouse antibody (HAMA) reaction. The disclosure provides pharmaceutical compositions comprising at least one of said antibodies or antibody fragments and a pharmaceutically acceptable carrier and methods of treating or ameliorating the amyloidosis and the symptoms of amyloidosis by administering to a patent an amount of said antibody or antibody fragment effective to remove at least some of the amyloid deposits from the patient's organs and thus to treat or ameliorate the disease and its symptoms.

Further in accordance with the present disclosure, methods are provided for treating amyloid deposition diseases. In particular, the present disclosure is directed towards improving myocardial function in a patient diagnosed with amyloid light chain amyloidosis (ALA) that has cardiac involvement. The methods comprise administering to a patient a humanized or chimeric antibody (e.g., mouse-human antibody) or an antigen-binding fragment thereof that binds to amyloid fibril deposits, circulating amyloids, and toxic amyloid precursor protein. In particular, the disclosure shows that administering the disclosed amyloid fibril-binding antibodies to patients diagnosed with ALA with cardiac involvement results in improved global longitudinal strain (GLS) compared to pretreatment GLS level, and/or a reduction in NT-proBNP level compared to pretreatment NT-proBNP level. Additionally, patients may be effectively treated even if their disease is not hematologically controlled (i.e., the patient has detectable levels of toxic amyloid precursor proteins in circulation or when the difference between involved and uninvolved free light chains of >40 mg/L) and regardless of whether the disease involves fibrils of kappa or lambda proteins.

Definitions

It is to be understood that methods are not limited to the particular embodiments described, and as such may vary. It is also to be understood that the terminology used herein is for the purpose of describing particular embodiments only, and is not intended to be limiting. The scope of the present technology will be limited only by the appended claims.

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "about" means plus or minus 10%.

As used herein, "optional" or "optionally" means that the subsequently described event or circumstance may or may not occur, and that the description includes instances where said event or circumstance occurs and instances where it does not.

As used herein, the terms "individual", "patient", or "subject" can be an individual organism, a vertebrate, a mammal (e.g., a bovine, a canine, a feline, or an equine), or a human. In a preferred embodiment, the individual, patient, or subject is a human.

As used herein, the term an "isolated antibody" is intended to refer to an antibody which is substantially free of other antibodies having different antigenic specificities (e.g., an isolated antibody that specifically binds to an amyloid fibril is substantially free of antibodies that do not bind to amyloid fibrils). An isolated antibody that specifically binds to an epitope of an amyloid light chain fibril (e.g., a kappa and/or lambda fibril) may, however, have cross-reactivity to other proteins, such as amyloid A fibrils. However, the antibody preferably always binds to human amyloid light chain fibrils. In addition, an isolated antibody is typically substantially free of other cellular material and/or chemicals.

As used herein, the phrases "therapeutically effective amount" and "therapeutic level" mean an antibody dose or plasma concentration in a subject, respectively, that provides the specific pharmacological effect for which the antibody is administered in a subject in need of such treatment, i.e., to reduce, ameliorate, or eliminate the effects or symptoms of an amyloid deposition disease, such as AL amyloidosis. It is emphasized that a therapeutically effective amount or therapeutic level of a drug will not always be effective in treating the conditions/diseases described herein, even though such dosage is deemed to be a therapeutically effective amount by those of skill in the art. The therapeutically effective amount may vary based on the route of administration and dosage form, the age and weight of the subject, and/or the subject's condition, including the type and stage of the amyloidosis at the time that treatment commences, among other factors.

The terms "treatment" or "treating" as used herein with reference to amyloid diseases, such as AL amyloidosis, refer to reducing, ameliorating or eliminating one or more symptoms or effects of the amyloidosis, including but not limited to clearance or degradation of amyloid plaques or deposits, improving organ function of organs effected by the disease (e.g., the heart, kidney, liver, etc.), and increasing the patient's lifespan or 5-year survival.

A "therapeutic response" mean an improvement in at least one measure of amyloid disease, such as a reduction in the size of existing amyloid deposits or plaques, a decrease in the rate of amyloid deposition, or improved organ function as measured by standard techniques. For instance, in patients with amyloid deposits in the heart, improved organ function (i.e., a therapeutic response) may be indicated by a decrease in the level of the patient's N-terminal pro b-type natriuretic peptide (NT-proBNP) or a decrease in the patient's New York Heart Association (NYHA) Functional Classification level. In patients with amyloid deposits in the kidneys, improved organ function (i.e., a therapeutic response) may be indicated by a decrease in proteinuria or the rate of protein output in the urine.

As used herein, the term "humanized antibody" refers to an antibody that comprises the CDRs of antibodies derived from mammals other than human, and the framework region (FR) and the constant region of a human antibody. A humanized antibody is useful as a therapeutically effective component in a therapeutic agent according to the present disclosure since antigenicity of the humanized antibody in human body is lowered.

As used herein, "cardiac involvement" means that a patient suffering from an amyloid disease have amyloid deposits in the heart. Amyloid deposits in the heart result in release of NT-proBNP and increased NT-proBNP levels in the blood of the patient. Herein, a patient has cardiac involvement if NT-proBNP is greater than 650 pg/mL.

As used herein, the description of "not hematologically controlled" with respect to AL amyloidosis means that the disease is not in either complete remission or very good partial remission. For example, the disease is not hematologically controlled when the patient has detectable levels of toxic amyloid precursor proteins in circulation (i.e., blood or serum) or when the difference between involved and uninvolved free light chains is >40 mg/L in the patient's blood or serum.

As used herein, the term "serious adverse event" means an untoward medical event that results in death, is life-threatening, requires inpatient hospitalization or prolongation of existing hospitalization, or results in persistent or significant disfigurement or disability, as defined in 21 CFR 312.32(a).

As used herein, the term "pharmaceutically-acceptable carrier" means a material for admixture with a pharmaceutical compound (e.g., a chimeric antibody) for administration to a patient as described, for example, in "Ansel's Pharmaceutical Dosage Forms and Delivery Systems", Tenth Edition (2014).

Anti-AL Antibodies
Murine Anti-Fibril Antibodies

Recent animal studies have shown that the administration of the murine 11-1F4 antibody and other murine anti-human light chain specific antibodies directed against an epitope common to the β-pleated-sheet structure present on AL fibrils results in complete degradation of the human ALκ and ALλ amyloid deposits. Some of these murine antibodies are described in U.S. Pat. No. 8,105,594 ("the '594 patent"), which is incorporated herein by reference in its entirety.

Murine antibodies are generally unsuitable for administration to other animal species (such humans) because the receiving species will recognize the murine antibody as antigenic and will produce antibodies against it. The antigenicity of an antibody from one species when injected into another species is normally caused by a portion of a constant domain. Such an antigenic response will impede or prevent the desired therapeutic effect of the murine antibody. In humans, this antigenic response is called human anti-mouse antibody (HAMA). The antibodies described in the '594 patent have the potential to be highly immunogenic in humans via the human anti-mouse antibody (HAMA) response. Since the HAMA response usually results in the rapid clearance of a mouse antibody from the human recipient, HAMA would severely limit any potential human therapeutic benefit a murine antibody could have. Therefore, these murine antibodies are unsuitable for administration to a patient to halt or reverse the deposition of amyloid fibrils in a patient. Thus, the present disclosure provides compositions and methods for treating amyloid deposition diseases that is less likely to produce an immunogenic HAMA response in a patient following administration.

Humanized and Chimeric Anti-Fibril Antibodies

The present disclosure provides humanized and chimeric antibodies or antigen-binding fragments thereof for treating amyloidosis. Typically, an antibody consists of four polypeptides: two identical copies of a heavy (H) chain polypeptide and two copies of a light (L) chain polypeptide. Typically, each heavy chain contains one N-terminal variable ($V_H$) region and three C-terminal constant (CH1, CH2 and CH3) regions, and each light chain contains one N-terminal variable ($V_L$ or $V_K$) region and one C-terminal constant (CL) region. Each variable domain of the light and heavy chain in an antibody also comprises three segments called complementarity-determining regions ("CDR") or hypervariable regions. Each CDR in a light chain, together with the corresponding CDR in the adjacent heavy chain, form an antigen-binding site of the antibody. The variable regions of each pair of light and heavy chains form the antigen binding site of an antibody, whereas the constant region provides structural support and modulates the immune response initiated by the antigen binding.

Chimeric antibodies incorporate the variable region of a non-human antibody into the constant region of a human antibody. A chimeric 11-1F4, for instance, may be created by expressing the murine variable region with the Fc region of a human antibody, such as a human IgG1.

Humanized forms of non-human (e.g., murine) antibodies can be obtained, which contain minimal sequences derived from non-human immunoglobulin. In general, a humanized antibody may comprise one or two or more variable domains in which variable regions are derived from non-human immunoglobulin and framework regions (FR) correspond to a human immunoglobulin sequence. Thus, in some embodiments, a humanized anti-AL antibody comprises a human antibody framework region. Such antibodies can be prepared by known techniques.

The murine 11-1F4 monoclonal antibody is an anti-AL antibody produced by the SP2/0 hybridoma cell deposited Alan Solomon, MD (University of Tennessee Medical Center at Knoxville, Tenn.). The hybridoma cell line is available from the American Type Culture Collection (ATCC access PTA-105). The $V_K$ region (SEQ ID NO: 36) and the $V_H$ region (SEQ ID NO: 35) of the 11-1F4 antibody are shown in Table 1 below. The CDR sequences for the heavy and light chains and provided in Table 2.

TABLE 1

11-1F4 monoclonal antibody variable sequences

SEQ ID NO: 36
$V_K$ region:
Asp Val Val Met Thr Gln Thr Pro Leu Ser Leu Pro
Val Ser Leu Gly Asp Gln Ala Ser Ile Ser Cys Arg
Ser Ser Gln Ser Leu Val His Arg Asn Gly Asn Thr
Tyr Leu His Trp Tyr Leu Gln Lys Pro Gly Gln Ser
Pro Lys Leu Leu Ile Tyr Lys Val Ser Asn Arg Phe
Ser Gly Val Pro Asp Arg Phe Ser Gly Ser Gly Ser
Gly Thr Asp Phe Thr Leu Lys Ile Ser Arg Val Glu
Ala Glu Asp Leu Gly Leu Tyr Phe Cys Phe Gln Thr
Thr Tyr Val Pro Asn Thr Phe Gly Gly Gly Thr Lys
Leu Glu Ile Lys SEQ ID NO: 35
$V_H$ region:
Gln Val Gln Leu Lys Glu Ser Gly Pro Gly Leu Val
Ala Pro Ser Gln Ser Leu Ser Ile Thr Cys Thr Val
Ser Gly Phe Ser Leu Ser Ser Tyr Gly Val Ser Trp
Val Arg Gln Pro Pro Gly Lys Gly Leu Glu Trp Leu
Gly Val Ile Trp Gly Asp Gly Ser Thr Asn Tyr His
Pro Asn Leu Met Ser Arg Leu Ser Ile Ser Lys Asp
Ile Ser Lys Ser Gln Val Leu Phe Lys Leu Asn Ser
Leu Gln Thr Asp Asp Thr Ala Thr Tyr Tyr Cys Val
Thr Leu Asp Tyr Trp Gly Gln Gly Thr Ser Val Thr
Val Ser Ser The complementarity determining regions (CDRs) of the variable sequences are shown in boldface type in the table above.

TABLE 2

11-1F4 monoclonal antibody CDR sequences

| Sequence | Amino Acid |
|---|---|
| CDRL1 (SEQ ID NO: 49) | Arg Ser Ser Gln Ser Leu Val His Arg Asn Gly Asn Thr Tyr Leu His |
| CDRL2 (SEQ ID NO: 50) | Lys Val Ser Asn Arg Phe Ser |
| CDRL3 (SEQ ID NO: 51) | Phe Gln Thr Thr Tyr Val Pro Asn Thr |
| CDRH1 (SEQ ID NO: 52) | Ser Tyr Gly Val Ser Trp |
| CDRH2 (SEQ ID NO: 53) | Val Ile Trp Gly Asp Gly Ser Thr Asn Tyr His Pro Asn Leu Met Ser Arg Leu Ser Ile Ser |
| CDRH3 (SEQ ID NO: 54) | Leu Asp Tyr |

One can clone the genes for the $V_H$ and $V_K$ regions shown above to produce a chimeric 11-1F4 antibody using known human antibody sequences. The chimeric 11-1F4 antibody binds to an epitope expressed by the β-pleated sheet configuration of amyloids, just as its murine counterpart does, but surprisingly, as shown in Example 6 below, the chimeric antibody binds to AL amyloid fibrils with higher affinity than the 11-1F4 mouse antibody from which it was derived.

One can also clone the genes for the CDR regions to produce a humanized form of the antibody using known human antibody sequences. Like the chimeric form of the 11-1F4 antibody, the humanized form may also have a binding affinity for amyloid fibrils that is higher than that of the murine counterpart.

Those of skill in the art will understand that the disclosed humanized and chimeric antibodies may utilize all different types of human constant regions and/or framework regions. For example, the disclosed humanized and chimeric antibodies may comprise the constant regions and/or framework regions of a human IgG (including IgG1, IgG2, IgG3, and IgG4), IgA, IgE, IgH, or IgM. In preferred embodiments, the disclosed humanized or chimeric 11-1F4 antibody comprises a human IgG1 constant region.

In some embodiments, the disclosed antibodies may comprise one or more substitutions, insertions, or deletions, so long as the antibody maintains the ability to bind to amyloid fibrils (e.g., kappa and/or lambda light chain fibrils). For example, in some embodiments, a chimeric 11-1F4 antibody of the present disclose may comprise heavy and light chains with about 85%, about 86%, about 87%, about 88%, about 89%, about 90%, about 91%, about 92%, about 93%, about 94%, about 95%, about 96%, about 97%, about 98%, about 99%, or about 100% identity compared to the corresponding heavy and light chain sequences disclosed herein, so long as the antibody maintains the ability to bind to amyloid fibrils. In some embodiments, a humanized 11-1F4 antibody of the present disclose may comprise CDRs that have about 85%, about 86%, about 87%, about 88%, about 89%, about 90%, about 91%, about 92%, about 93%, about 94%, about 95%, about 96%, about 97%, about 98%, about 99%, or about 100% identity compared to the corresponding CDR sequences disclosed herein, so long as the antibody maintains the ability to bind to amyloid fibrils.

In some embodiments, the disclosed humanized or chimeric antibody binds to amyloid fibrils with a higher affinity than its murine equivalent in vitro and/or in vivo as determined by, for example, the direct binding ELISA assay described in Example 6. Without being bound by theory, it is thought that the disclosed humanized and chimeric 11-1F4 antibodies can bind and neutralize toxic circulating amyloid proteins that have not yet formed deposits or fibrils, and the disclosed humanized and chimeric antibodies can dissolve amyloid deposits. Indeed, chimeric 11-1F4 antibodies were demonstrated to bind to fibrils and to dissolve human amyloidomas in mice. This is of note because it is believed that the precursor light chain protein is toxic to cardiomyocytes, and therefore a treatment approach that can target the circulating toxic amyloid precursor proteins as well the aggregated amyloid fibrils deposited within organs could improve cardiovascular outcomes in patients with AL Amyloidosis that has myocardial involvement, even if the patient's disease is not hematologically controlled (i.e., the patient has detectable levels of toxic amyloid precursor proteins in the patient's blood or serum or the difference between involved and uninvolved free light chains of >40 mg/L).

ABBREVIATIONS

Dulbecco's Modified Eagles Medium (DMEM), Fetal Bovine Serum (FBS), ribonucleic acid (RNA); messenger RNA (mRNA); deoxyribonucleic acid (DNA); copy DNA (cDNA); polymerase chain reaction (PCR); minute (min); second (sec); Tris-borate buffer (TBE).

Amino acids are represented by the IUPAC abbreviations, as follows: Alanine (Ala), Arginine (Arg), Asparagine (Asn), Aspartic acid (Asp), Cysteine (Cys), Glutamine (Gln), Glutamic acid (Glu), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), Valine (Val). Similarly for nucleotides: Adenine (A), Cytosine (C), Guanine (G), Thymine (T), Uracil (U), Adenine or Guanine (R), Cytosine or Thymine (Y), Guanine or Cytosine (S), Adenine or Thymine (W), Guanine or Thymine (K), Adenine or Cytosine (M), Cytosine or Guanine or Thymine (B), Adenine or Guanine or Thymine (D), Adenine or Cytosine or Thymine (H), Adenine or Cytosine or Guanine (V), and any base (N).

Humanized or Chimeric Antibodies

To produce the chimeric antibodies of the invention, the murine 11-1F4 monoclonal antibody heavy and kappa light chain variable region genes described in U.S. Pat. No. 8,105,594 were PCR modified to facilitate the expression of the chimeric 11-1F4 antibody in mammalian cells. A detailed sequence analysis of the modified variable region genes was performed. The modified variable region genes were cloned into the appropriate mammalian expression vectors, creating the constructs 11-1F4VHpG1D200 and 11-1F4VK.pKN100. A single supervector construct, pG1KD200-11-1F4, was made from the 11-1F4VHpG1D200 and 11-IF4VK.pKN100 constructs by EcoRI restriction enzyme digest and ligation. Finally, the chimeric 11-1F4 antibody was transiently expressed in COS cells by both cotransfection and single supervector transfection. While COS cells were chosen for the co-transfection or transfection as a matter of convenience, those of skill in the art would recognize that other mammalian cell lines could be used. The characterization of the binding capacity of the chimeric 11-1F4 antibody for amyloid fibrils was determined by direct binding ELISA. Unexpectedly and beneficially, the chimeric 11-1F4 antibody bound to amyloid fibrils with higher affinity than the murine 11-1F4 antibody.

Typically, an antibody consists of four polypeptides: two identical copies of a heavy (H) chain polypeptide and two copies of a light (L) chain polypeptide. Typically, each heavy chain contains one N-terminal variable ($V_H$) region and three C-terminal constant (CH1, CH2 and CH3) regions, and each light chain contains one N-terminal variable ($V_L$ or $V_K$) region and one C-terminal constant (CL) region. The variable regions of each pair of light and heavy chains form the antigen binding site of an antibody.

An antibody useful in the compositions and methods of the invention may be a chimeric mouse-human monoclonal antibody comprising the $V_K$ region of SEQ ID NO: 47 and the $V_H$ region of SEQ ID NO: 48 or a humanized monoclonal antibody comprising CDR sequences of SEQ ID NOs: 49-54. These antibodies bind to an epitope expressed by the β-pleated sheet configuration of amyloid fibrils. Moreover, surprisingly the antibodies bind to this epitope with higher affinity than the 11-1F4 mouse antibody from which they were derived, which comprises the $V_K$ region of SEQ ID NO: 36 and the $V_H$ region of SEQ ID NO: 35. The invention includes methods of treating an amyloid deposition disease in a human patient in need of such treatment which comprises administering to the patient a therapeutically effective dose of one of the above antibodies in a pharmaceutically-acceptable carrier. The amount of antibody administered should be effective, for example, to reduce the amount of amyloid fibrils deposited in the tissues of the patient. The antibody composition may be administered by any conventional route of administration, but parenteral administration (such as intravenous) is preferred. Pharmaceutically-acceptable carriers are well-known in the art and a suitable one can be selected by one of skill in the medical field. The amyloid deposition disease is preferably primary (AL) amyloidosis.

Figure 5:
FIG. 5 is a map of the immunoglobulin gamma 1 heavy chain expression vector pG1D200. It consists of a pSV2dhfr vector fragment, which has the SV40 early and crippled SV40 late promoter, the SV40 origin, and the Co1E1 origin. It also has the ampicillin resistance and dhfr genes. The crippled SV40 late promoter drives the dhfr gene. Consequently, expression is poor, allowing for the selection of multigene/high expression level clones using comparatively low levels of methotrexate. It also has the HCMVi promoter fragment, a multiple cloning site, cDNA for a human gamma 1 constant region gene (intron minus) which is followed by a spaC2 termination signal sequence ("Arnie").

A chimeric antibody useful for the compositions and methods of the described and claimed herein (and a method of making the chimeric antibody) is disclosed in co-owned Patent Cooperation Treaty application PCT/US2018/039905 (with priority to U.S. patent application 62/526,835, filed Jun. 29, 2017), filed on even date herewith and incorporated herein in its entirety. Materials useful to make the subject antibody include vector constructs selected from the group consisting of 11-1F4VK.pKN100 and 11-F4VH.pG1D200, shown in FIGS. 5 and 6, respectively, and the superconstruct pG.1KD20011-1F4 made from the two above vector constructs. Other useful materials include the modified murine 11-1F4 antibody $V_K$ region gene (SEQ ID NO: 42) and the modified 11-1F4 antibody $V_H$ region gene (SEQ ID NO: 45), as well as the respective primers SEQ ID NO: 41, 43, 44, and 46. The subject antibody may be made by co-transfection of the vector constructs 11-1F4VK.pKN100 and 11-F4VH.pG1D200 or the superconstruct pG.1KD20011-1F4 in a suitable mammalian host cell, such as COS (Chinese hamster ovary) cells.

Methods of making, testing, and using the humanized or chimeric 11-1F4 antibody are discussed in further detail in the Examples section below.

Pharmaceutical Formulations

Pharmaceutical compositions suitable for use in the methods described herein can include the disclosed humanized or chimeric 11-1F4 antibodies, humanized antibodies, or antigen-binding antibody fragments and a pharmaceutically acceptable carrier or diluent.

The composition may be formulated for intravenous, subcutaneous, intraperitoneal, intramuscular, oral, nasal, pulmonary, ocular, vaginal, or rectal administration. In some embodiments, the antibodies are formulated for intravenous, subcutaneous, intraperitoneal, or intramuscular administration, such as in a solution, suspension, emulsion, liposome formulation, etc. The pharmaceutical composition can be formulated to be an immediate-release composition, sustained-release composition, delayed-release composition, etc., using techniques known in the art.

Pharmacologically acceptable carriers for various dosage forms are known in the art. For example, excipients, lubricants, binders, and disintegrants for solid preparations are known; solvents, solubilizing agents, suspending agents, isotonicity agents, buffers, and soothing agents for liquid preparations are known. In some embodiments, the pharmaceutical compositions include one or more additional components, such as one or more preservatives, antioxidants, stabilizing agents and the like.

Additionally, the disclosed pharmaceutical compositions can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In some embodiment, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Pharmaceutical compositions of the disclosure can be administered in combination with other therapeutics that are part of the current standard of care for amyloidosis and amyloid diseases. Alternatively, the disclosed pharmaceutical compositions may be administered to a patient that has previously received conventional treatment for amyloidosis and amyloid diseases, but who has not responded to conventional treatment (i.e., the disease is refractory or continues to progress).

Methods of Treatment

In the present invention, at least one chimeric antibody, humanized antibody, or antigen-binding antibody fragment thereof is administered to a patient (e.g., a human patient) suffering from amyloidosis to promote the degradation and removal of at least some of the amyloid fibrils which have become deposited in the organs of the patient and/or which are circulating in the patient's bloodstream. In some embodiments, therapeutically effective amount of the antibody is administered together with a pharmaceutically acceptable carrier. Suitable pharmaceutically acceptable carriers are well-known in the art, as discussed infra. A typical route of administration is parenterally (e.g., intravenously, subcutaneously, or intramuscularly), as is well understood by those skilled in the medical arts. Other routes of administration are, of course, possible. Administration may be by single or multiple doses. The amount of antibody administered and the frequency of dosing may be optimized by the physician for the particular patient.

Amyloidosis can affect different organs in different people, and there are different types of amyloid. Amyloidosis frequently affects the heart, kidneys, liver, spleen, nervous system and digestive tract. Severe amyloidosis can lead to life-threatening organ failure.

Signs and symptoms of amyloidosis may include, but are not limited to: swelling of the ankles and legs; severe fatigue and weakness; shortness of breath; numbness, tingling or pain in the hands or feet, especially pain in the wrist (carpal tunnel syndrome); diarrhea, possibly with blood, or constipation; unintentional, significant weight loss; an enlarged tongue; skin changes, such as thickening or easy bruising, and purplish patches around the eyes; an irregular heartbeat; or difficulty swallowing.

In general, amyloidosis is caused by the buildup of an abnormal protein called amyloid. Amyloid is produced in the bone marrow and can be deposited in any tissue or organ. The specific cause of the condition depends on the type of amyloidosis.

There are several types of amyloidosis or amyloid diseases, including AL amyloidosis, AA amyloidosis, and hereditary amyloidosis.

AL amyloidosis (immunoglobulin light chain amyloidosis) is the most common type and can affect the heart, kidneys, skin, nerves and liver. Previously known as primary amyloidosis, AL amyloidosis occurs when the bone marrow produces abnormal antibodies that cannot be broken down. The antibodies are deposited in various tissues as amyloid plaques, which interfere with normal function of the tissue or organ.

AA amyloidosis generally affects the kidneys but occasionally also affects the digestive tract, liver or heart. It was previously known as secondary amyloidosis. It often occurs along with chronic infectious or inflammatory diseases, such as rheumatoid arthritis or inflammatory bowel disease.

Hereditary amyloidosis (familial amyloidosis) is an inherited disorder that usually often affects the liver, nerves, heart, and/or kidneys. Many different types of gene abnormalities present at birth are associated with an increased risk of amyloid disease or hereditary amyloidosis. The type and location of an amyloid gene abnormality can affect the risk of certain complications, the age at which symptoms first appear, and the way the disease progresses over time.

When an amyloid disease affects the heart, it can cause numerous types of complications. Amyloid deposits or plaques reduce the heart's ability to fill with blood between heartbeats. Less blood is pumped with each beat, and this may lead to shortness of breath. Amyloid deposits or plaques in or around the heart may also cause irregular heartbeats and congestive heart failure, among other organ dysfunctions When an amyloid disease affects the kidneys, it will often harm the kidneys' filtration ability, allowing protein to leak from the blood into the urine (i.e., proteinuria). Moreover, the kidneys' ability to remove waste products from your body is lowered, which may eventually lead to kidney failure.

Provided herein are methods of treating an amyloid deposition diseases, such as primary (AL) amyloidosis, in a patient (e.g., a human patient) in need of such treatment which comprises administering to the patient a humanized or chimeric 11-1F4 antibody together with a pharmaceutically acceptable carrier, in an amount effective to treat the amyloid deposition disease.

In some embodiments, the amyloid deposition disease (e.g., primary amyloidosis) comprises involvement of at least one organ or tissue selected from the group consisting of heart, kidneys, liver, lung, gastrointestinal tract, nervous system, muscular skeletal system, soft tissue, and skin.

In embodiments when the disease involves amyloid deposits or plaques in the patient's heart, treatment with the disclosed humanized or chimeric 11-1F4 antibody may decrease the levels of the patient's N-terminal pro b-type natriuretic peptide (NT-proBNP) by at least about 30% compared to baseline levels taken prior to administration of the antibody. In some embodiments, the decrease in NT-proBNP may be at least about 40%, at least about 50%, at least about 60% or more compared to baseline levels taken prior to administration of the antibody. In some embodiments, treatment with the disclosed human or chimeric 11-1F4 antibody may result in the patient's NT-proBNP level decreasing to less than about 9100 ng/L following administration of the antibody. In some embodiments, the patient's NT-proBNP level may decrease to less than about 8000, 7000, 6000, 5000, or 4000 ng/L following administration of the antibody. In some embodiments, the patient may initially be classified as New York Heart Association (NYHA) Functional Classification class II or III prior to administration of the antibody, but after treatment with the disclosed chimeric 11-1F4 antibody the patient may be classified as class I on the NYHA classification scale.

Provided herein are methods of improving myocardial function in patient suffering from amyloidosis with cardiac involvement, as well as methods for treating specific subpopulations of patients, such as those with ALA that has cardiac involvement (i.e., NT-proBNP is greater than 650 pg/mL) and that is not hematologically controlled.

When an amyloid disease affects the heart, it can cause numerous types of complications and this cardiac involvement portends poor prognosis. Amyloid deposits or plaques reduce the heart's ability to fill with blood between heartbeats. Less blood is pumped with each beat, and this may lead to shortness of breath, among other serious complicating factors. Amyloid deposits or plaques in or around the heart may also cause irregular heartbeats and congestive heart failure, among other organ dysfunctions.

Provided herein are methods of improving myocardial function in a patient diagnosed with amyloid light chain amyloidosis (ALA) with cardiac involvement comprising administering to a patient diagnosed with ALA with cardiac involvement a therapeutically effective amount of a humanized or chimeric 11-1F4 antibody or an antigen-binding fragment thereof. The antibody or an antigen-binding fragment thereof may bind to amyloid fibrils with higher affinity than murine 11-1F4 antibody, as determined by direct binding ELISA. Further, the improvements in myocardial function may be apparent within about three weeks after administering the antibody or antigen-binding fragment thereof. For example, improvement in various measures of myocardial function may be seen within about 1, about 2, about 3, about 4, about 5, about 6, about 7, about 8, about 9, about 10, about 11, about 12, about 13, about 14, or about 15 weeks of the initiation of treatment.

The myocardial function of patients having cardiac involvement can be determined by measuring N-terminal pro b-type natriuretic peptide (NT-proBNP) levels. Tissue damage caused by amyloid deposits in the heart of ALλ patients increases NT-proBNP levels in the patients. In some embodiments, the patients diagnosed with ALA having cardiac involvement exhibits a pre-treatment NT-proBNP level greater than 650 pg/mL.

Myocardial function and improvement therein can be measured by using echocardiography to measure global longitudinal strain (GLS) as described in Smiseth et al.—*Eur Heart J*, 37:1196. Echocardiography uses ultrasound to measure the average deformation within segments of the myocardium, and GLS is the average of these segments as a measure of global left ventricular function. Amyloid deposits can result in thickened left and right ventricular walls and in a non-dilated ventricle that is stiff and poorly compliant, resulting in "strain" on the heart and vasculature. In echocardiography parlance, the term "strain" is used to describe deformation in the myocardium, which may include but is not limited to local shortening, thickening, and/or lengthening of the myocardium. Strain can be used as a measure of ventricular function. A person having ordinary skill in the art will know how to use echocardiography to determine GLS and will understand that it may be calculated in various ways. For example, the Lagrangian formula $(\varepsilon_L=(L-L_0)/L_0=\Delta L/L_0$, where $L_0$ is baseline length and L is the resulting length), defines strain in relation to the original length as a dimensionless measure, in which shortening will be negative, and lengthening will be positive. It is usually expressed in percent. An alternative definition, Eulerian strain, defines the strain in relation to the instantaneous length: $\varepsilon_E=\Delta L/L$. For a change over time, the Lagrangian strain will be: $\varepsilon_L=\Sigma \Delta L/L_0$, and Eulerian Strain $\varepsilon_E=\Sigma(\Delta L/L)$. The term was first used by Mirsky and Parmley in describing regional differences in deformation between normal and ischemic myocardium.

Hence, in some embodiments, the patients of the presently disclosed method exhibits an improvement in global longitudinal strain (GLS) compared with pretreatment GLS level. For instance, in a study of 19 patients treated with the disclosed chimeric antibody, 10 of these patients had cardiac involvement per screening NT-proBNP levels, and 8 patients were cardiac evaluable per baseline NT-proBNP, wherein cardiac involvement is defined by having NT-proBNP level greater than 650 pg/mL. In some embodiments, a patient with ALA with cardiac involvement may have a baseline NT-proBNP of at least 650 pg/ml, while in some embodiments, a patient with ALA with cardiac involvement may have a baseline NT-proBNP of at least 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, or 2300 or more pg/ml.

As disclosed in Example 9 below, 9 out of the 10 patients having cardiac involvement exhibited improvement in myocardial function upon exposure to the disclosed chimeric antibody as shown in FIG. 15. Hence, in some embodiments, the patient treated with a therapeutically effective dose of the chimeric antibody exhibits an improvement in global longitudinal strain (GLS) compared with pretreatment GLS level. Concomitant with reduced GLS, the patients treated with the disclosed antibodies may also exhibit reduced NT-proBNP levels.

In some embodiments, the improvement in GLS may occur within about 1, about 2, about 3, about 4, about 5, about 6, about 7, about 8, about 9, about 10, about 11, about 12, about 13, about 14, or about 15 weeks of the initiation of treatment. In some embodiments, the improvement in GLS may be represented by a 1, 2, 3, 4, 5, 6, 7, 8, 9, 10, 11, 12, 13, 14, 15, 16, 17, 18, 19, 20, 21, 22, 23, 24, 25, or more percent reduction in GLS compared to baseline as calculated by the Lagrangian formula. A reduction in GLS level compared to baseline of about 2% percent or more is considered clinically relevant.

In some embodiments, the disclosed treatments with the humanized or chimeric 11-1F4 antibody or an antigen-binding fragment thereof may decrease the levels of the patient's N-terminal pro b-type natriuretic peptide (NT-proBNP) by at least about 30% compared to baseline levels taken prior to administration of the antibody. In some embodiments, the decrease in NT-proBNP may be at least about 40%, at least about 50%, at least about 60% or more compared to baseline levels taken prior to administration of the antibody. In some embodiments, treatment with the disclosed chimeric 11-1F4 antibody may result in the patient's NT-proBNP level decreasing to less than about 9100 ng/L following administration of the antibody. In some embodiments, the patient's NT-proBNP level may decrease to less than about 8000, 7000, 6000, 5000, or 4000 ng/L following administration of the antibody. In some embodiments, the patient may initially be classified as New York Heart Association (NYHA) Functional Classification class II or III prior to administration of the antibody, but after treatment with the disclosed chimeric 11-1F4 antibody the patient may be classified as class I on the NYHA classification scale.

In some embodiments, the disclosed methods comprise treating a patient suffering from relapse or refractory ALA. In some embodiments, the patient may have kappa ALA. In some embodiments, the patient may have lambda ALA.

Immunoglobulins are composed of four protein chains: two light chains, either kappa (κ) or lambda (λ) light chains, and two heavy chains, of which there are several types. In AL amyloidosis, either kappa light chains or lambda light chain may be misfolded and form amyloid fibrils or plaques. Hence, in some patients, both kappa and lambda fragments may be misfolded. Subgroup analysis showed that patients with both lambda cardiac involvement and kappa cardiac involvement showed improvement by having reduced GLS compared to pre-treatment levels as shown in Example 8.

Hence, in some embodiments the patient is further characterized as having light chain lambda amyloid cardiac involvement. In some embodiments, the patient is further characterized as having light chain kappa amyloid cardiac involvement.

In some embodiments, the disclosed methods of treatment may further comprise administering a chemotherapeutic drug that may be intended to kill the dysfunctional cells that are creating the toxic precursor protein. In some cases, such therapy may be successful, thereby resulting in a decrease in dysfunctional cells and a concomitant decrease in the amount of circulating toxic amyloid precursor proteins in the patient's blood. However, in some cases, chemotherapy may be ineffective in decreasing the number of dysfunctional cells and/or the ability of these cells to produce the toxic amyloid precursor proteins. Those patients that continue to have detectable levels of circulating toxic amyloid precursor proteins in their blood are said to have ALA that is not hematologically controlled.

The disclosed methods of treatment may be particularly beneficial for patients with disease that is not hematologically controlled (i.e., in neither complete remission nor very good partial remission) because the presently disclosed humanized and chimeric 11-1F4 antibodies are believed to be able to bind to and neutralize toxic amyloid precursor proteins in circulation, even before the proteins aggregate to form an amyloid deposit. Complete remission is defined as negative serum and urine immunofixation and normal ratio in a free-light-chain (FLC) assay, while very good partial remission is defined as having a difference between involved and uninvolved free light chains of <40 mg/L.

Monitoring Improvement

Echocardiography is non-invasive and can be used to monitor improvement in myocardial function in a patient diagnosed with light chain amyloidosis (ALA) having a cardiac involvement comprising observing an improvement in myocardial function in a patient diagnosed with ALA having a cardiac involvement within about three weeks after administration to said patient of a therapeutically effective amount of a humanized or chimeric 11-1F4 antibody (c11-1F4 Ab) or an antigen-binding fragment thereof, said humanized or chimeric 11-1F4 Ab or an antigen-binding fragment thereof having a binding affinity to amyloid fibrils, which is higher than that of murine 11-1F4 antibody, as determined by direct binding ELISA. Hence, the improved myocardial function can be observed in about three weeks after administration of the humanized or chimeric 11-1F4 antibody as shown in Example 8. In some embodiments, the improvement in myocardial function persists for a period extending at least three months after administration of the humanized or chimeric 11-1F4 Ab or an antigen-binding fragment thereof.

In embodiments when the disease involves amyloid deposits or plaques in the patient's kidneys, treatment with the disclosed humanized or chimeric 11-1F4 antibody may decrease the level of protein in the patient's urine (i.e., proteinuria) by at least about 30% compared to baseline levels determined prior to administration of the antibody. In some embodiments, the decrease in protein in the patient's urine may be at least about 40%, at least about 50%, at least about 60% or more compared to baseline levels determined prior to administration of the antibody. In some embodiments, the patient's urine protein output may decrease to less than about 7000, less than about 6000, less than about 5000, less than about 4000, or less than about 3000 mg/24 hours following administration of the antibody.

Therapeutically Effective Doses and Dosing Regimens

In some embodiment, the therapeutically effective dose of the antibody may be administered no more than once, twice, three, or four times within a three month period. In some embodiments, the reduction in NT-proBNP or improvement in GLS is sustained in the patient for at least about three months after the administration of a humanized or chimeric 11-1F4 antibody.

Therapeutically effective doses and dosing regimens of the foregoing methods may vary, as would be readily understood by those of skill in the art. Dosage regimens may be adjusted to provide the optimum desired response (e.g., a therapeutic response clearance of amyloid plaques or reduction in the amount of deposited amyloid fibrils). For example, in some embodiments, a single dose of the antibody may be administered, while in some embodiments, several divided doses may be administered over time, or the dose may be proportionally reduced or increased in subsequent dosing as indicated by the situation. For example, in some embodiments the disclosed antibodies may be administered once or twice weekly by subcutaneous, intravenous, or intramuscular injection. In some embodiments, the disclosed antibodies or antigen-binding fragments thereof may be administered once or twice monthly by subcutaneous, intravenous, or intramuscular injection. In some embodiments, the disclosed antibodies or antigen-binding fragments thereof may be administered once or twice annually by subcutaneous, intravenous, or intramuscular injection. In some embodiments, the disclosed antibodies or antigen-binding fragments thereof may be administered once every week, once every other week, once every three weeks, once every four weeks, once every month, once every other month, once every three months, once every four months, once every five months, once every six months, once every seven months, once every eight months, once every nine months, once every ten months, once every eleven months, twice a year, or once a year, as the situation or condition of the patient may indicate.

Moreover, the data disclosed herein indicates that patient response to treatment with humanized or chimeric 11-1F4 antibody is not only sustained, but rapid as well. In some embodiments, a patient may experience a therapeutic response (i.e., a decrease in the size of amyloid deposits or plaques, a decrease in the rate of plaque formation, or improved organ function) in one week or less, two weeks or less, three weeks or less, four weeks or less, five weeks or less, six weeks or less, seven weeks or less, eight weeks or less, nine weeks or less, ten weeks or less, eleven weeks or less, twelve weeks or less, or any time frame in between. For example, depending on the dose and dosing regimen, a patient may experience a therapeutic response in about a week or about 4.5 weeks.

The therapeutically effective dose of antibody administered to the patient (whether administered in a single does or multiple doses) should be sufficient to reduce the amount of deposited amyloid fibrils in the patient. Such therapeutically effective amount may be determined by evaluating the symptomatic changes in the patient or by evaluating the change in the amount of deposited amyloid fibrils (e.g., by radioimmune detection of deposited amyloid deposits using $^{124}$I tagged antibody). Thus, a labeled antibody of the disclosure may be used to detect the presence of amyloid deposition disease in a patient suspected of having the disease as well as to determine the effectiveness of treatment.

Exemplary doses can vary according to the size and health of the individual being treated, as well as the condition being treated. In some embodiments, a therapeutically effective amount of a disclosed humanized or chimeric 11-1F4 antibody may be about 500 mg/m$^2$ or less; however, in some situations the dose may be higher. In some embodiments, a therapeutically effective dose may be 10-1000 mg/m$^2$, 25-900 mg/m$^2$, 50-800 mg/m$^2$, 75-700 mg/m$^2$, 100-600 mg/m$^2$, or any value in between. For instance, in some embodiments, the therapeutically effective amount may be about 1000, about 975, about 950, about 925, about 900, about 875, about 850, about 825, about 800, about 775, about 750, about 725, about 700, about 675, about 650, about 625, about 600, about 575, about 550, about 525, about 500, about 475, about 450, about 425, about 400, about 375, about 350, about 325, about 300, about 275, about 250, about 225, about 200, about 175, about 150, about 125, about 100 or less mg/m$^2$.

Similarly, in some embodiments, the effective amount of a humanized or chimeric 11-1F4 antibody is about 2,200 mg; however, in some situations the dose may be higher or lower. In some embodiments, a therapeutically effective amount may be between 50 and 5000 mg, between 60 about 4500 mg, between 70 and 4000 mg, between 80 and 3500 mg, between 90 and 3000 mg, between 100 and 2500 mg, between 150 and 2000 mg, between 200 and 1500 mg, between 250 and 1000 mg, or any dose in between. For instance, in some embodiments, the therapeutically effective amount may be about 50 about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000 or more mg.

Similarly, in some embodiments, the effective amount of a humanized or chimeric 11-1F4 antibody is about 25 mg/kg; however, in some embodiments, the concentration may be higher or lower. In some embodiments, the effective amount may be about 1-50 mg/kg, about 5-40 mg/kg, about 10-30 mg/kg, or about 15-25 mg/kg or any value in between. For instance, in some embodiments, the effective amount may be 1, 2, 3, 4, 5, 6, 7, 8, 9, 10, 11, 12, 13, 14, 15, 16, 17, 18, 19, 20, 21, 22, 23, 24, 25, 26, 26, 28, 29, 30, 31, 32, 33, 34, 35, 36, 37, 38, 39, 40, 41, 42, 43, 44, 45, 46, 47, 48, 49, or 50 or more mg/kg.

The disclosed methods of treatment may also be combined with other known methods of treatment as the situation may require. The current standard of care for AL amyloidosis, for example, generally involves autologous blood stem cell transplantation (ASCT) or an autologous bone marrow transplant. Many of the same chemotherapy medications that treat multiple myeloma are used in AL amyloidosis to stop the growth of abnormal or dysfunctional cells that produce amyloid/toxic amyloid precursor proteins. Thus, in some embodiments, the disclosed humanized or chimeric 11-1F4 antibodies may be administered before, after, or concurrently with other known treatments. In some embodiments, the disclosed humanized or chimeric 11-1F4 antibodies may be administered only after other treatment options have failed or the disease has continued to progress.

In other words, in some embodiments, the disclosed antibodies are used to treat refractory amyloid disease, such as refractory AL amyloidosis.

In embodiments when the disease involves amyloid deposits or plaques in the patient's kidneys, treatment with the disclosed chimeric 11-1F4 antibody may decrease the level of protein in the patient's urine (i.e., proteinuria) by at least about 30% compared to baseline levels determined prior to administration of the antibody. In some embodiments, the decrease in protein in the patient's urine may be at least about 40%, at least about 50%, at least about 60% or more compared to baseline levels determined prior to administration of the antibody. In some embodiments, the patient's urine protein output may decrease to less than about 7000, less than about 6000, less than about 5000, less than about 4000, or less than about 3000 mg/24 hours following administration of the antibody.

Also provided herein are methods of treating a patient with an amyloid deposition disease (e.g., AL amyloidosis) comprising administering a therapeutically effective amount of a humanized or chimeric 11-1F4 antibody to a patient in need thereof less frequently than once per month. In some embodiments, the AL amyloidosis may comprise aggregates of lambda light chain fibrils, in which case the presence of aggregates of lambda light chain fibrils is significantly reduced following administration of the antibody.

In some embodiment, the therapeutically effective dose of the antibody may be administered once every two months, once every three months, once every four months, once every five months, once every six months, or biannually, and more specific dosing regimens are discussed below.

Also provided herein are methods of treating a patient with primary light chain (AL) amyloidosis involving the heart comprising administering to said patient a dose of a humanized chimeric 11-1F4 antibody, said dose being effective to cause at least a 30% reduction in N-terminal pro b-type natriuretic peptide (NT-proBNP) level following administration of the humanized or chimeric 11-1F4 antibody as compared to pre-treatment level. Also included are methods of treating a patient with primary light chain (AL) amyloidosis involving the kidneys comprising administering to said patient a dose of a humanized or chimeric 11-1F4 antibody, said dose effective to cause at least a 40% reduction in proteinuria following administration of the humanized or chimeric 11-1F4 antibody compared to pre-treatment levels.

In some embodiments, the reduction in NT-proBNP and/or proteinuria is sustained in the patient for at least about six months after the administration of the humanized or chimeric 11-1F4 antibody.

As described above, immunoglobulins are composed of four protein chains: two light chains, either kappa (κ) or lambda (λ) light chains, and two heavy chains, of which there are several types. In AL amyloidosis, either kappa light chains or lambda light chain may be misfolded and form amyloid fibrils or plaques. In some patients, both kappa and lambda fragments may be misfolded. Thus, provided herein are methods of decreasing the amount of kappa and/or lambda light chain fibril aggregate deposits in a patient in need thereof comprising, administering to a patient with primary amyloidosis comprising kappa or lambda light chain fibril aggregate deposits a dose of an antibody comprising: (i) a $V_K$ region comprising SEQ ID NO: 47, a $V_H$ region comprising SEQ ID NO: 48 or (ii) CDR sequences comprising SEQ ID NOs: 49-54, and a human IgG1 constant region; wherein the does is effective to decrease the amount of kappa or lambda light chain fibril aggregate deposits in the patient.

In some embodiments, the primary amyloidosis consists of lambda light chain fibril deposits or plaques, while in some embodiments, the primary amyloidosis consists of kappa light chain fibril aggregate deposits, and in some embodiments, the primary amyloidosis consists of kappa and lambda light chain fibril aggregate deposits.

It was surprisingly discovered herein that chimeric 11-1F4 is unexpectedly efficacious in clearing lambda light chain fibrils. Indeed, preclinical experiments such as the mouse study provided in Example 7 suggested that lambda fibrils were resistant to clearance and would requirement multiple recurrent treatments in order for the deposits to clear. However, as shown in Example 8, when the chimeric 11-1F4 antibody was administered to humans, the treatment resulted in a decrease in lambda chain amyloid deposits after only a single dose. This result was entirely unexpected prior to performing the disclosed methods. It is believed that a humanized 11-1F4 antibody would exhibit a similar capacity to clear lambda light chain fibrils.

In any of the foregoing methods, administration of the disclosed humanized or chimeric 11-1F4 antibody is expected to decrease organ dysfunction. Additionally, in any of the foregoing methods, the constant region of the antibody may be a human IgG constant region. More specifically, in some embodiments, the constant region of the antibody may be a human IgG1 constant region.

Therapeutically effective doses and dosing regimens of the foregoing methods may vary, as would be readily understood by those of skill in the art. Dosage regimens may be adjusted to provide the optimum desired response (e.g., a therapeutic response clearance of amyloid plaques or reduction in the amount of deposited amyloid fibrils). For example, in some embodiments, a single bolus dose of the antibody may be administered, while in some embodiments, several divided doses may be administered over time, or the dose may be proportionally reduced or increased in subsequent dosing as indicated by the situation. For example, in some embodiments the disclosed antibodies may be administered once or twice weekly by subcutaneous, intravenous, or intramuscular injection. In some embodiments, the disclosed antibodies or functional fragments may be administered once or twice monthly by subcutaneous, intravenous, or intramuscular injection. In some embodiments, the disclosed antibodies or functional fragments may be administered once or twice annually by subcutaneous, intravenous, or intramuscular injection. In some embodiments, the disclosed antibodies may be administered once every week, once every other week, once every three weeks, once every four weeks, once every month, once every other month, once every three months, once every four months, once every five months, once every six months, once every seven months, once every eight months, once every nine months, once every ten months, once every eleven months, twice a year, or once a year, as the situation or condition of the patient may indicate.

Moreover, the data disclosed herein indicates that patient response to treatment with humanized or chimeric 11-1F4 antibody is not only sustained, but also rapid as well. In some embodiments, a patient may experience a therapeutic response (i.e., a decrease in the size of amyloid deposits or plaques, a decrease in the rate of plaque formation, or improved organ function) in one week or less, two weeks or less, three weeks or less, four weeks or less, five weeks or less, six weeks or less, seven weeks or less, eight weeks or less, nine weeks or less, ten weeks or less, eleven weeks or less, twelve weeks or less, or any time frame in between. For example, depending on the dose and dosing regimen, a patient may experience a therapeutic response in about a week or about 4.5 weeks.

The following examples are given to illustrate the present invention. It should be understood, however, that the invention is not to be limited to the specific conditions or details described in these examples. All printed publications referenced herein are specifically incorporated by reference.

Example 1

PCR Cloning and DNA Sequencing of the Mouse 11-1F4 Antibody

The murine 11-1F4 monoclonal antibody heavy and light chain variable region genes were PCR cloned and a detailed sequence analysis of all variable region genes isolated (both pseudo and functional) was performed. Detailed DNA and amino acid sequences of the murine 11-1F4 antibody heavy and light chain variable region genes were obtained.

Materials

Media components and all other tissue culture materials were obtained from Life Technologies (UK). The RNA solution kit was obtained from Stratagene (USA), while the first strand cDNA synthesis kit was purchased from Pharmacia (UK). All the constituents and equipment for the RCR-reaction, including AmpliTaq® DNA polymerase, were purchased from Perkin Elmer (USA). The TOPO TA Cloning® kit was obtained from Invitrogen (USA). Agarose (UltraPure™) was obtained from Life Technologies (UK). The ABI PRISM® Big Dye™ terminator cycle sequencing ready reaction kit pre-mixed cycle sequencing kit and the ABI PRISM® 310 sequencing machine were both purchased from PE Applied Biosystems (USA). All other molecular biological products were obtained from New England Biolabs (USA) and Promega (USA).

Methods

Figure 1:
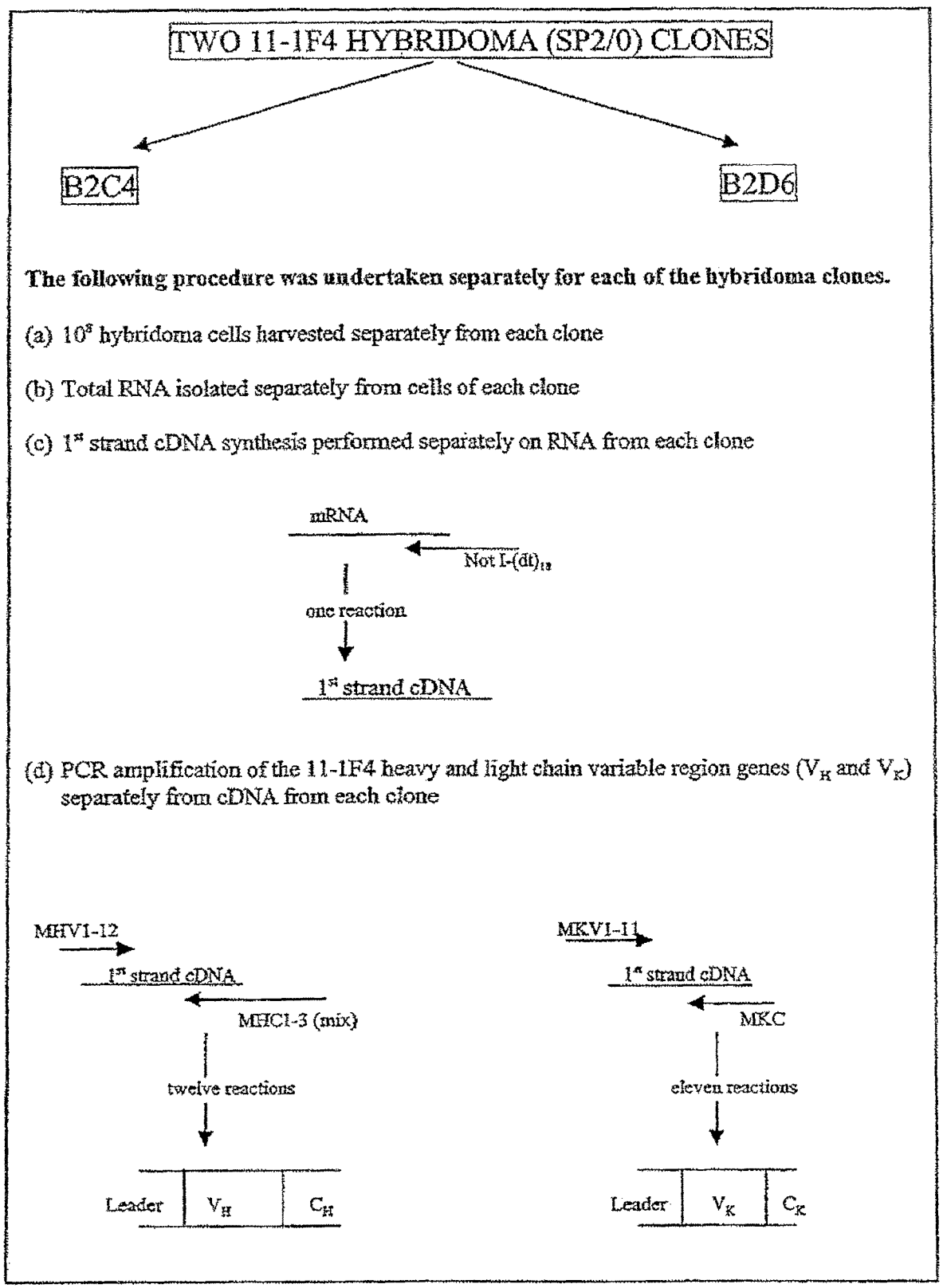
FIG. 1 outlines the strategy used to clone the murine $V_H$ and $V_K$ genes from a hybridoma cell line.

The strategy used to PCR clone the murine $V_H$ and $V_K$ genes from the hybridoma cell lines producing the murine monoclonal antibody 11-1F4 is outlined in FIG. 1.

Two clones (B2C4 and B2D6) of the SP2/0 hybridoma cell line producing the α-human light chain monoclonal antibody 11-1F4, were kindly provided by Alan Solomon, MD (University of Tennessee Medical Center at Knoxville, Tenn.). The hybridoma cell line is available from the American Type Culture Collection (ATCC access PTA-105). The cell lines were cultured using DMEM media supplemented with 20% (v/v) FBS, penicillin/streptomycin and L-Glutamine. Cells were cultured until a total viable cell count of $10^8$ cells was reached.

The cells were harvested separately from each clone as follows. The mouse hybridoma cell line was grown in suspension in an appropriate culture medium and in sufficient quantities to provide a total viable cell count of about $10^8$ cells. The culture supernatant was harvested and the hybridoma cells pelleted in a bench top centrifuge (250 g, 5 min). The cells were gently re-suspended in 20 ml PBS and a 100 µl aliquot was taken for a viable cell count. The cells in the aliquot were pelleted once more and 200 µl of PBS and 200 µl of trypan blue were added to the 100 µl of cells and mixed gently. Ten µl of this mixture was pipetted into a disposable cell-counting slide and the number of white cells in 9 small squares was counted under a microscope. Blue cells (i.e., dead cells) were not counted. The count process was repeated, the results averaged, and the average results multiplied by $9 \times 10^5$ to obtain a viable cell count for the cells in 20 ml PBS. Once sufficient cells had been harvested, they were re-suspended in 10 ml of Solution D for RNA isolation (see below, Stratagene RNA Isolation Kit).

Total RNA was then isolated separately from the cells of each clone using a Stratagene RNA isolation kit, according to the manufacturer's instructions. One ml of 2 M sodium acetate (pH 4.0) was added to the sample and the contents of the tube were thoroughly mixed by repeatedly inverting the tube. To the tube was added 10.0 ml of phenol (pH 5.3-5.7) and the contents again mixed thoroughly by inversion. To the mixture was added 2.0 ml of chloroform-isoamyl alcohol mixture, the tube was capped and vigorously shaken for 10 seconds, and the tube was incubated in ice for 15 minutes. The sample was transferred to a 50-ml thick-walled, round-bottom centrifuge tube that had been pre-chilled on ice and the tube was spun in a centrifuge at 10,000×g for 20 minutes at 4° C. Two phases were visible in the tube after centrifugation. The upper, aqueous phase contained the RNA, while the lower phenol phase and interphase contained DNA and proteins. The RNA-containing upper, aqueous phase was transferred to a fresh centrifuge tube and the lower phenol phase was discarded. An equal volume of isopropanol was added to the aqueous phase and the contents mixed by inversion, following which the tube was incubated for 1 hour at −20° C. to precipitate the RNA. The tube was spun in a centrifuge at 10,000×g for 20 minutes at 4° C. After centrifugation, the pellet at the bottom of the tube, which contains the RNA, was removed and the supernatant discarded. The pellet was dissolved in 3.0 ml of solution D, 3.0 ml of isopropanol was added to the tube and the contents mixed well. After incubating the tube for 1 hour at −20° C., it was again spun in a centrifuge at 10,000×g for 10 minutes at 4° C. and the supernatant removed from the tube and discarded. (Note: Up to this point. the RNA had been protected from ribonucleases by the presence of guanidine isothiocyanate but was now no longer protected.) The pellet was washed with 75% (v/v) ethanol (DEPC-treated water (25%)) and the pellet was dried under vacuum for 2-3 minutes. The RNA pellet is re-suspended in 0.5-2 ml of DEPC-treated water.

Following the manufacturer's instructions, an Amersham Pharmacia Biotech first strand cDNA synthesis kit was employed to produce a single-stranded DNA copy of the 11-1F4 hybridoma mRNA using the Not I-d(T)$^{18}$ primer supplied with the kit. One reaction was performed for each of the two RNA samples isolated, as follows. The components used were: Bulk first strand cDNA reaction mix, Cloned FPLCpure™ Murine Reverse Transcriptase, RNAguar™, BSA, dATP, dCTP, dGTP, and dTTP, 200 mM DIT aqueous solution, Not I-d(T)$^{18}$ primer: 5'-d[AACTGGAAGAATTCGCGGCCGCAGGAA$_{18}$]-3' (SEQ ID NO: 55), and DEPC treated water.

Approximately 5 μg of total RNA in 20 μl DEPC water was heated to 65° C. for 10 min and then chilled on ice. The bulk first strand cDNA reaction mix was pipetted gently to obtain a uniform suspension and the reaction set up in a 0.5 ml microcentrifuge tube as below. 20 μl denatured RNA solution, 11 μl Bulk first strand cDNA reaction mix, 1 μl Not I-d(T)$^{18}$ primer, and 1 μl DTT solution for 33 μl total volume. The reactants were mixed gently by pipetting and incubated 37° C. for 1 hour.

The murine heavy and kappa light chain variable region genes ($V_H$ genes and $V_K$ genes, respectively) were then PCR amplified from the ssDNA template using the method described by Jones and Bendig (*Bio/Technology* 9:88).

Separate PCR reactions were prepared for each of the degenerate leader sequence specific primers (MHVI-MHV12 for $V_H$ and MKVI-MKV11 for $V_K$) with the appropriate constant region primer (an equimolar mix of MHCI-MHC3 for $V_H$ and MKC for $V_K$). Tables I & 2 detail the primers used to amplify the $V_H$ and $V_K$ region genes, respectively. In total, 12 heavy chain reactions and 11 kappa light chain reactions were performed. AmpliTaq® DNA polymerase was used to amplify the template cDNA in all cases, as follows.

The completed cDNA first strand synthesis reaction was heated at 90° C. for 5 minutes to denature the RNA-cDNA duplex and inactivate the reverse transcriptase and chilled on ice. Eleven GeneAmp™ PCR reaction tubes were labeled MKV1-11. For each tube a 100 μl reaction mixture was prepared, each reaction mixture containing 69.3 μl of sterile water, 10 μl of 10×PCR buffer II, 6 μl of 25 mM MgCl$_2$, 2 μl each of the 10 mM stock solutions of dNTPs, 2.5 μl of 10 mM MKC primer, 2.5 μl of one of the 10 mM MKV primers and 1 μl of RNA-cDNA template mix. To each of the tubes was then added 0.7 μl of AmpliTaq® DNA polymerase and the completed reaction mix overlaid with 50 μl of mineral oil.

A similar series of reaction mixes was prepared as described above to PCR-clone the mouse heavy chain variable region gene. However, this time twelve reaction tubes were labeled and one of the twelve MHV primers and the appropriate MHC primer were added to each. That is, to PCR-amplify the variable domain gene of a mouse γ1 heavy chain, for example, the MHC G1 primer was used.

The reaction tubes were loaded into a DNA thermal cycler and cycled (after an initial melt at 94° C. for 1.5 min) at 94° C. for 1 min, 50° C. for I min and 72° C. for 1 min over 25 cycles. The last cycle was followed by a final extension step at 72° C. for 10 min before cooling to 4° C. Except for between the annealing (50° C.) and extension (72° C.) steps when an extended ramp time of 2.5 min was used, a 30 sec ramp time was used between each step of the cycle. A 10 μl aliquot from each PCR reaction was run on a 1% (w/v) agarose/1×TBE buffer gel containing 0.5 μg/ml ethidium bromide to determine which of the leader primers produced a PCR-product. Positive PCR-clones were about 420-500 bp in size.

The above PCR-amplification process was repeated twice more and those PCR-reactions that appeared to amplify full-length variable domain gene were selected. A 6 μl aliquot of each potential PCR-product was directly cloned into the pCR™ II vector provided by the TA Cloning® kit, as described in the manufacturers instructions. Aliquots of 10.0% (v/v), 1.0% (v/v) and 0.1% (v/v) aliquots of the transformed *E. coli* cells were pipetted onto individual 90 mm diameter LB agar plates containing 50 μg/ml ampicillin, overlaid with 25 μl of the X-Gal stock solution and 40 μl of IPTG stock solution, and incubated overnight at 37° C. Positive colonies were identified by PCR-screening.

TABLE 1

PCR primers for cloning mouse kappa light chain variable region genes

| Name | Sequence (5'→3') | SEQ ID NO: |
|---|---|---|
| MICV1 (31 mer) | ATGAAGATTGCCTGTTA GGCTGTTGGTGCTG | 1 |
| MKV2 (30 mer) | ATGGAGWCAGACACACT CCTGYTATGGGTG | 2 |

TABLE 1-continued

PCR primers for cloning mouse kappa light chain variable region genes

| Name | Sequence (5'→3') | SEQ ID NO: |
|---|---|---|
| MKV3 (30 mer) | ATGAGTGTGCTCACTCAGGTCCTGGSGTTG | 3 |
| MKV4 (33 mer) | ATGAGGRCCCCTGCTCAGWTTYTTGGMWTCTTG | 4 |
| MKV5 (30 mer) | ATGGATTTWCAGGTGCAGATTWTCAGCTTC | 5 |
| MKV6 (29 mer) | ATGAGGTKCYYTGYTSAYCTYCTCTGRGG | 6 |
| MKV7 (32 mer) | ATGGGCWTCAAAGATGGAGTCACAKWYYCWGG | 7 |
| MKV8 (30 mer) | ATGTGGGGAYCTKTTTYCMMTTTTTCAATG | 8 |
| MKV9 (25 mer) | ATGGTRTCCWCASCTCAGTTCCTTG | 9 |
| MKV10 (27 mer) | ATGTATATATGTTTGTTGTCTATTTCT | 10 |
| MKV11 (28 mer) | ATGGAAGCCCCAGCTCAGCTTCTCTTCC | 11 |
| MKC (20 mer) | ACTGGATGGTGGGAAGATGG | 12 |

TABLE 2

PCR primers for cloning mouse heavy chain variable region genes

| Name | Sequence (5'→3') | SEQ ID NO: |
|---|---|---|
| MHV1 (27 mer) | ATGAAATGCAGCTGGGGCATSTTCTTC | 13 |
| MHV2 (26 mer) | ATGGGATGGAGCTRTATCATSYTCTT | 14 |
| MHV3 (27 mer) | ATGAAGWTGTGGTTAAACTGGGTTTTT | 15 |
| MHV4 (25 mer) | ATGRACTTTGGGYTCAGCTTGRTTT | 16 |
| MHV5 (32 mer) | ATGGGACTCCAGGCTTCAATTTAGTTTTCCTT | 17 |
| MHV6 (29 mer) | ATGGCTTGTCYTTRGSGCTRCTCTTCTGC | 18 |
| MHV7 (27 mer) | ATGGRATGGAGCKGGRGTCTTTMTCTT | 19 |
| MHV8 (23 mer) | ATGAGAGTGCTGATTCTTTTGTG | 20 |
| MHV9 (31 mer) | ATGGMTTGGGTGTGGAMCTTGCTTATTCCTG | 21 |
| MHV10 (28 mer) | ATGGGCAGACTTACCATTCTCATTCCTG | 22 |
| MHV11 (28 mer) | ATGGATTTTGGGCTGATTTTTTTATTG | 23 |

TABLE 2-continued

PCR primers for cloning mouse heavy chain variable region genes

| Name | Sequence (5'→3') | SEQ ID NO: |
|---|---|---|
| MHV12 (27 mer) | ATGATGGTGTTAAGTCTTCTGTACCTG | 24 |
| MHCG1 (21 mer) | CAGTGGATAGACAGATGGGGG | 25 |
| MHCG2a (21 mer) | CAGTGGATAGACCGATGGGGG | 26 |
| MHCG2b (21 mer) | CAGTGGATGAGCTGATGGGGG | 27 |
| MHCG3 (21 mer) | CAAGGGATAGACAGATGGGGC | 28 |

Five μl aliquots from each PCR reaction were run on a 1% agarose/TBE (pH 8.8) gel to determine which had produced a PCR product of the correct size (ca. 450 bp). Those putative positive PCR products so identified were directly cloned into the pCR2.1 vector provided by the TA Cloning® kit and transformed into TOP10 competent cells as described in the manufacturer's protocol. Colonies containing the plasmid with a correctly sized insert were identified by PCR-screening the colonies using the 1212 and 1233 oligonucleotide primers (Table 3) according to the method of Güssow and Clackson (*Nucleic Acids Res.* 17:4000). Those putative positive clones so identified were double-stranded plasmid DNA sequenced using the ABI PRISM 310 Genetic Analyzer and the ABI PRISM BigDye™ terminator. Three positive clones each of the $V_H$ and $V_K$ genes from the B2C4 hybridoma cell line clone were sequenced, as were four positive clones of the $V_K$ gene and six of the $V_H$ gene from the B2D6 hybridoma cell line clone.

TABLE 3

Primers for PCR screening and sequencing transformed colonies

| Name | Sequence (5'→3') | SEQ ID NO: |
|---|---|---|
| 1212 (17 mer) | GTTTTCCCAGTCACGAC | 29 |
| 1233 (21 mer) | AGCGGATAATTTCACACAGGA | 30 |

The results of the 12 PCR reactions performed for each hybridoma clone (B2C4 and BCD6) to amplify the murine 11-1F4 antibody heavy chain variable region gene are presented in Table 4(a).

The degenerate leader sequence primer MHV7, in combination with a mix of the MHCGI-3 constant region primers (Table 1), yielded a PCR product of about 600 bp from template cDNAs derived from both the B2C4 and B2D6 hybridoma cell lines. Since this band was larger than the expected size for an average $V_H$ gene (450 bp), it was not investigated further. Conversely, the degenerate leader sequence primer MHV6, in combination with a mix of the MHCGI-3 constant region primers (Table 1), yielded a PCR product of the expected size (450 bp) for a $V_H$ gene from template cDNA derived from both the B2C4 and B2D6 hybridoma cell lines.

Table 4 shows the results of the PCR amplifications performed to clone the murine 11-1F4 monoclonal antibody variable region heavy (a) and light (b) chain genes from the SP2/0 hybridoma cell lines B2C4 and B2D6. Column three contains a record of the actual PCR results. Where a band was observed for a particular combination of primers its size in base pairs (bp) was recorded in the appropriate space.

TABLE 4

Results of PCR amplification (a)

| $C_H$ Region Primer | Leader Primer | Approximate Band Size (bp) | |
|---|---|---|---|
| | | B2C4 | B2D6 |
| MHCG1-3 (mix) | MHV1 | | |
| " | MHV2 | | |
| " | MHV3 | | |
| " | MHV4 | | |
| " | MHV5 | | |
| " | MHV6 | 450 | 450 |
| " | MHV7 | 600 | 600 |
| " | MHV8 | | |
| " | MHV9 | | |
| " | MHV10 | | |
| " | MHV11 | | |
| " | MHV12 | | |

(b)

| $C_K$ Region Primer | Leader Primer | Approximate Band Size (bp) | |
|---|---|---|---|
| | | B2C4 | B2D6 |
| MKC | MHV1 | 450 | 450 |
| " | MHV2 | <450 | <450 |
| " | MHV3 | | |
| " | MHV4 | | |
| " | MHV5 | | |
| " | MHV6 | 200 | |
| " | MHV7 | | |
| " | MHV8 | | |
| " | MHV9 | | |
| " | MHV10 | | |
| " | MHV11 | | |

Sequence analysis of three clones from the B2C4 derived PCR product and five clones from the B2D6 derived PCR product revealed a single heavy chain variable region sequence (FIG. 2).

The cloning strategy used (amplification of the entire variable region gene by using primers which flank this region, i.e., leader sequence and constant region sequence specific primers) allowed the complete FR1 sequence to be identified. All eight clones sequenced had identical sequence in this region (FIG. 2).

The results of the 11 PCR reactions performed for each hybridoma clone (B2C4 and BCD6) to amplify the murine 11-1F4 antibody kappa light chain variable region gene are presented in Table 4(b).

The degenerate leader sequence primer MHV6 in combination with the MKC constant region primer (Table 2), produced a PCR product of about 200 bp from template cDNA derived from the B2C4 hybridoma cell line only. Since this band was much smaller than the expected size for a $V_K$ gene (450 bp), it was not investigated further.

The degenerate leader sequence primer MHV2, in combination with the MKC constant region primer (Table 2), produced a PCR product which was smaller than the expected 450 bp band (when viewed on an agarose gel) from template cDNA derived from both the B2C4 and B2D6 hybridoma cell lines. In addition, previous $V_K$ cloning had found that the MKV2 primer amplified a well known kappa light chain pseudogene. Therefore, sequence analysis of one clone of each PCR product was performed in order to confirm that this product was a pseudogene and not the murine 11-1F4 antibody $V_K$ gene. This sequence analysis revealed that this PCR clone was indeed the pseudogene.

Finally, the degenerate leader sequence primer MKV1, in combination with the MKC constant region primer (Table 1), produced a PCR product of about the expected size (450 bp) for a $V_K$ gene, from template cDNA derived from both the B2C4 and B2D6 hybridoma cell lines.

Sequence analysis of three clones of the B2C4 derived PCR product and four clones of the B2D6 derived PCR product revealed a single kappa light chain variable region sequence which could not be identified as a pseudogene.

Thus, the 11-1F4 antibody heavy chain variable region gene was cloned (using constant region specific and leader sequence specific primers) from the hybridoma mRNA and sequenced.

When translated, the sequence gave a TVSS peptide sequence. Analysis of 122 rearranged human $V_H$ genes, recorded in the Kabat database (Kabat et al. —Sequences of Proteins of Immunological Interest), revealed that 84% of these sequences had a TVSS peptide sequence. It was therefore concluded that the $V_H$ gene isolated was the correct 11-1F4 antibody gene sequence.

The murine 11-1F4 antibody variable region kappa light chain gene was also successfully cloned and sequenced, as was a non-functional $V_K$ pseudogene gene. This pseudogene was first identified by Carroll et al (Molecular Immunology (1988) 25:991). The sequence arises from an aberrant mRNA transcript which is present in all standard fusion partners derived from the original MOPC-21 tumor (including SP2/0). As a result of the aberrant mRNA, the invariant cysteine at position 23 is replaced by a tyrosine residue, and the VJ joint is out of frame, resulting in a stop codon at position 105.

It is common for lymphoid or hybridoma cells to synthesize more than one rearranged light immunoglobulin mRNA. These mRNAs are usually non productive due to the presence of termination codons or frame shifts not usually seen in functional $V_K$ genes. These pseudo messengers often present major problems when cloning immunoglobulin genes from hybridomas because they are very good substrates for V region PCR, despite the fact that they do not encode functional polypeptides.

The 11-1F4 antibody $V_K$ gene sequence was identified after detailed sequence analysis of seven separate PCR clones, isolated from two different PCR products to yield SEQ. ID NO: 36. Since all sequences were identical, it was accepted as the correct 11-1F4 antibody kappa light chain variable region sequence.

The cloned $V_H$ and $V_K$ region genes were used to make the chimeric mouse-human 11-1F4 monoclonal antibody, which was then be analyzed to confirm specific binding to AL fibrils.

Example 2

Construction of Chimeric Mouse-Human 11-1F4 (c11-1F4) Antibody

In order to allow transient expression of the 11-1F4 $V_H$ and $V_K$ variable region genes described above in mammalian cells as part of a chimeric mouse-human antibody, it was necessary to modify the 5'- and 3'-ends using specifically designed PCR primers (Table 5). The oligonucleotide primers F39836 and F39837 were used to PCR modify the 11-1F4 $V_K$ gene, while primers F39835 and F58933 were used to PCR modify the 11-1F4 $V_H$ gene. The back (BAK) primers F39836 and F39835 introduced a HindIII restriction site, a Kozak translation initiation site, and an immunoglobulin leader sequence to the 5' ends of the $V_K$ and $V_H$ genes respectively. The forward (FOR) oligonucleotide primer F39837 introduced a splice donor site and a BamHI restriction site to the 3' end of the $V_K$ gene while the forward (FOR) oligonucleotide primer F58933 appended the first 22 base pairs of the gamma-1CH$_1$ gene including an ApaI restriction site to the 3' end of the $V_H$ gene.

TABLE 5

Oligonucleotide primers used to PCR modify the 11-1F4 heavy and kappa light chain variable region genes

| Name | Sequence (5'→3') | SEQ ID NO: |
|---|---|---|
| F39835 VH BAK | AAGCTTGCCGCCACCATGGCTGT CCTGGGGCTGCTCITCTGC | 31 |
| F58933 VH FOR | CCGATGGGCCCTTGGTGGAGGCT GAGGAGACGGTGACTGAGGTTCC | 32 |
| F39836 VK BAK | AAGCTTGCCGCCACCATGAAGTT GCCTGTTAGGCTGTTGGTGC | 33 |
| F39837 VK FOR | GGATCCACTCACGTTTGATTTCC AGCTTGGTCCCCCCTCCGA | 34 |

The Kozak consensus sequence is crucial to the efficient translation of a variable region sequence (Kozak—*J Mol Bio* 196:947). It defines the correct AUG codon from which a ribosome commences translation, and the single most critical base is the adenine (or less preferably, a guanine) at position −3, upstream of the AUG start.

The immunoglobulin leader sequence ensures that the expressed antibody is secreted into the medium and therefore is easily harvested and purified. The leader sequences used in this instance were the murine 11-1F4 $V_K$ and $V_H$ leader sequences cloned from the hybridoma cDNA during the $V_H$ and $V_K$ cloning process.

The splice donor sequence is important for the correct in-frame attachment of the light chain variable region to its appropriate constant region, thus splicing out the 130 bp $V_K$:$C_K$ intron. The heavy chain variable region was attached directly to its appropriate constant region gene via the ApaI site, thus eliminating the need for a splice donor site.

The sub-cloning restriction sites HindIII and BamHI, and HindIII and ApaI, respectively, bracket the modified $V_K$ and $V_H$ variable region genes, while the use of different unique restriction sites ensured directional sub-cloning into the appropriate mammalian expression vector.

The 11-1F4 light chain variable region gene was first carefully analyzed to identify any unwanted splice donor sites, splice acceptor sites, and Kozak sequences (see Table 6). Both the heavy and light chain variable region genes were analyzed for the presence of any extra sub-cloning restriction sites which would later interfere with the sub-cloning and/or expression of functional whole antibody. None were found.

TABLE 1

Sequences important for the efficient expression of immunoglobulin genes in mammalian cells

| Name | Consensus DNA Sequences |
|---|---|
| Kozak translation initiation site | CCGCCRCCAUGG (SEQ ID NO: 56) |
| Kappa light chain splice donor site | AC::GTRAGT |
| Heavy chain splice donor site | AG::GTRAGT |
| Immunoglobulin splice acceptor site | YYYYYYYYYYNCAG::G (SEQ ID NO: 57) |

Bases shown in bold are considered to be invariant within each consensus sequence.

Separate PCR reactions were prepared as follows, one for each variable region gene. The plasmids 11-1F4 $V_H$.pCR2.1 and 11-1F4 $V_K$.pCR2.1 described above were used as templates. A 100 µl reaction mixture was prepared in each PCR tube, each mixture containing up to 41 µl of sterile water, 10 µl of 10×PCR buffer I, 8 µl of the 10 mM stock solution of dNTPs, 1 µl of 10 mM of 5' forward primer, 1 µl of the 10 mM 3' Reverse primer, and 1 µl of a 1/10 dilution of template DNA. Finally, 0.5 µl of AmpliTaq® DNA polymerase (2.5 units) was added before overlaying the completed reaction mixture with 50 µl of mineral oil. The reaction tubes were loaded into a DNA thermal cycler and cycled (after an initial melt at 94° C. for 1 min) at 94° C. for 30 sec, 68° C. for 30 sec and 72° C. for 50 sec over 25 cycles. The completion of the last cycle was followed with a final extension step at 72° C. for 7 min before cooling to 4° C. A 10 µl aliquot from each PCR reaction tube was run on a 1.2% (w/v) agarose/ 1×TBE buffer gel containing 0.5 µg/ml ethidium bromide to determine size and presence of a PCR-product. Positive PCR-clones were about 420 bp in size. Those putative positive PCR products so identified were directly cloned into the pCR2.1 vector, provided by the Topo TA Cloning® kit, and transformed into TOP10 competent cells as described in the manufacturer's protocol. Colonies containing the plasmid with a correctly sized insert were identified by PCR-screening the colonies using the 1212 and 1233 oligonucleotide primers (Table 3) according to the method of Güssow and Clackson. Those putative positive clones so identified were double-stranded plasmid DNA sequenced using the ABI PRISM 310 Genetic Analyzer and the ABI PRISM BigDye™ terminator. Two positive clones each of the Topo TA cloned $V_H$ and $V_K$ genes were sequenced.

Figure 4:
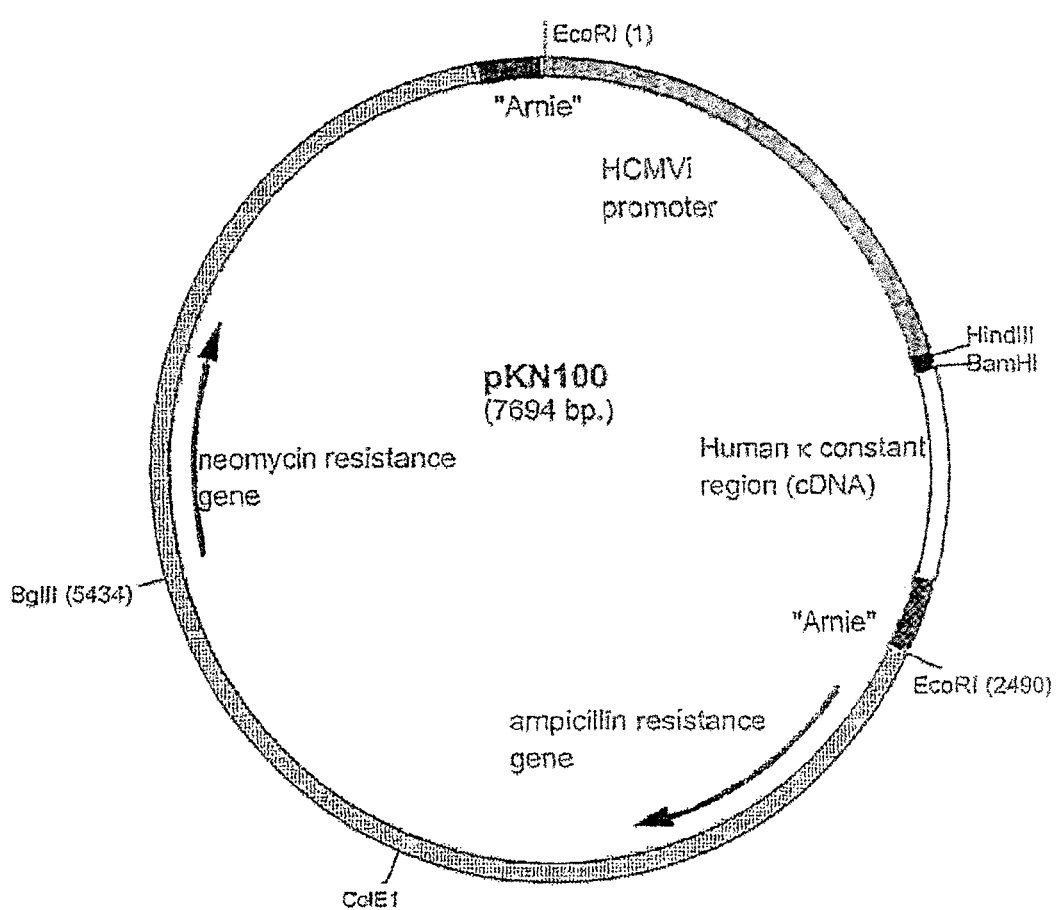
FIG. 4 is a map of the immunoglobulin kappa light chain expression vector pKN100. It consists of a pSV2 vector fragment, which has the SV40 early and crippled SV40 late promoter, the SV40 origin and the Co1E1 origin. It also has the ampicillin resistance and neo genes. The crippled SV40 late promoter drives the neo genes. It also has the HCMVi promoter, a multiple cloning site (containing the BamHI and HindIII restriction sites) for the insertion of an immunoglobulin variable region gene, and cDNA for the human kappa constant region gene terminated by a spaC2 termination signal sequence ("Arnie"), which is in the same orientation as the kappa light chain expression cassette.

Clones containing the correctly modified 11-1F4 $V_H$ and 11-1F4 $V_K$ genes were identified and the modified V genes from these clones were subcloned into their respective expression vectors to facilitate the expression of chimeric heavy and kappa light chains in mammalian cells. The modified 11-1F4 $V_K$ gene was subcloned into the expression vector pKN100 (FIG. 4) as a HindIII-BamHI fragment; this vector contains a human kappa constant region gene (allotype: Km (3 Ala153, Ser191)). The modified 11-1F4 $V_H$ gene was also subcloned as a HindIII-ApaI fragment into the expression vector pG1D200 (FIG. 5); this vector contained a human γ1 constant region gene (allotype: G1m (−1 Glu377, Met38I, −2 Ala462, 3 Arg222, Ser229)). Both the kappa and γ1 constant region allotypes used are commonly found in the caucasian population. The ligated expression constructs, 11-1F4VK.pKN100 and 11-1F4VH.pG1D200, were then used to transform DH5a competent cells, and positive clones were identified using the PCR screening method discussed above with the original PCR modification primers (Table 4). The expression vectors are readily available.

Example 3

Construction of a Single Supervector for Transient Expression of Chimeric 11-1F4 in COS Cells.

A single supervector expressing both immunoglobulin chains of the chimeric 11-1F4 antibody was constructed as follows. The 11-1F4 kappa light chain expression cassette (which contained the HCMVi promoter, the 11-1F4 kappa light chain variable region gene, and the kappa light chain constant region gene) was restriction enzyme digested (EcoRI at positions 1 and 2490) out of the 11-1F4VK.pKN100 construct (FIG. 4) and subsequently ligated into the 11-1F4VHpG1D200 construct via the unique EcoRI (position 4297, FIG. 5). This ligation resulted in the construction of a supervector construct, pG1KD200-11-1F4, containing both the heavy and kappa light chains of the 11-1F4 chimeric antibody.

Example 4

Transient Expression of the Chimeric γ1/κ.11-IF4 Whole Antibody in COS Cells

The chimeric 11-IF4 antibody was transiently expressed in COS cells from the European Collection of Cell Cultures (ECACC) in two ways:
  (i) By cotransfection of 10 µg of each of the vector constructs 11-1F4VK.pKN100 and 11-1F4VH.pG1D200. Co-transfections were carried out in duplicate.
  (ii) By transfection of 13 µg of the single supervector construct pG1KD200-11-1F4. Supervector transfections were carried out five times.

The following transfection method was used. The COS cell line was grown in DMEM supplemented with 10% (v/v) FCS, 580 µg/ml L-glutamine and 50 Units/ml penicillin/50 µg/ml streptomycin ("media") in a 150 $cm^2$ flask until confluent. The cells were trypsinized, spun down in a bench top centrifuge (250 g for 5 min), then re-suspended in 6 ml of media before dividing them equally between three 150 $cm^2$ flasks, each containing 25 ml of fresh, pre-warmed media. The cells were incubated overnight at 37° C. in 5% $CO_2$ and then harvested the next day while they are still growing exponentially. Each flask contained approximately $1\times10^7$ cells. The cells were trypsinized again, pelleted as before, and washed in 20 ml of PBS, following which they were re-suspend in sufficient PBS to create a cell concentration of $1\times10^7$ cells/ml. 700 µl of these washed COS cells were pipetted into a Gene Pulser® cuvette, to which was then added 1 µl of both the heavy chain and kappa light chain expression vector DNA (each at 10 µg) or 13 µg of the super-vector construct. A 1900 Volt, 25 µFarad capacitance pulse was delivered to the mixture using the Bio-Rad Gene Pulser® apparatus. The pulsing was repeated for each experimental transfection and a "no DNA" control (in which the COS cells were electroporated in the absence of any DNA). A positive control of a previously-expressed antibody was also carried out to test the efficiency of the COS cells.

The COS cells were allowed to recover at room temperature for 10 min, then gently pipetted the into a 10 cm diameter tissue culture dish containing 8 ml of pre-warmed DMEM supplemented with 10% (v/v) γ-globulin free FBS, 580 µg/ml L-glutamine and 50 Units/ml penicillin/50 µg/ml streptomycin, and incubated in 5% $CO_2$ at 37° C. for 72 hours before harvesting the COS cell supernatant for analysis. After incubation for 72 hours the medium was collected, spun to remove cell debris and analyzed by ELISA for chimeric antibody production and antigen binding of the c11-1F4 antibody.

Example 5

Quantification of the Chimeric γ1/κ 11-1F4 Antibody Via Capture ELISA

Following expression, the whole IgG molecules present in the COS cell supernatant were quantified using a capture ELISA assay. IgG molecules were captured on a Nunc-Immuno MaxiSorb™ plate via an immobilized goat anti-human IgG, Fcγ fragment—specific antibody, and detected via an anti-human kappa light chain peroxidase conjugated antibody. A standard curve was generated by capturing and detecting known concentrations of a standard IgG antibody on the same plate in the same way as follows. Each well of a 96-well immunoplate was coated with 100 µl aliquots of 0.4 µg/ml goat anti-human IgG antibody diluted in PBS and incubated overnight at 4° C. The excess coating solution was removed and the plate was washed three times with 200 µl/well of washing buffer (1×PBS, 0.1% TWEEN). Into all wells except the wells in column 2, rows B to G, was dispensed 100 µl of SEC buffer. A 1 µg/ml solution of the human IgG1/kappa antibody in SEC buffer was prepared to serve as a standard and 200 µl/well was pipetted into the wells in column 2, rows B and C. The medium from the transfected cos cells was centrifuged (250 g, 5 min), saving the supernatant. An aliquot of 200 µl of the supernatant from the "no DNA" control (in which COS cells were transfected in the absence of DNA) was pipetted into the well in column 2, row D, and aliquots of 200 µl/well of experimental supernatants were pipetted into the wells in column 2, rows E, F, and G. The 200 µl aliquots in the wells of column 2, rows B to G were mixed and then 100 µl was transferred from each well to the neighboring well in column 3. This process was continued to column 11 with a series of 2-fold dilutions of the standard, control, and experimental samples, following which all were incubated at 37° C. for 1 hour and all the wells were rinsed six times with 200 µl aliquots of washing buffer. The goat anti-human kappa light chain peroxidase conjugate was diluted 5000-fold in SEC buffer and 100 µl of the diluted conjugate added to each well, followed by a repetition of the incubation and rinsing steps. To each well was added 150 µl of K-BLUE substrate, followed by incubation in the dark at 25° C. for 10 min. The reaction was stopped by adding 50 µl of RED STOP solution to each well and the optical density was read at 655 nm.

Example 6

Binding Analysis of the Chimeric 11-1F4 Antibody

The chimeric 11-1F4 antibody was tested for binding to amyloid fibrils using a direct binding ELISA assay. Synthetic fibrils were formed from an immunoglobulin light chain protein and used to monitor the reactivity of the antibody in a solid-state ELISA-based assay using a "low-binding" polystyrene plates (Costar, #3474). Immediately prior to coating the plate, a mass of 250 µg of fibrils was diluted to 1 ml with coating buffer (0.1% bovine serum albumin in phosphate buffered saline pH 7.5). The sample was then sonicated for 20 sec using a Tekmar Sonic Disruptor sonicating probe, with the power set to 40% of maximum, resulting in a solution of short fibrils composed of up to 2-5 protofilaments each. This solution was then diluted to 5 ml, mixed well by vortex, and aliquoted into the wells of the plate. This process yielded 50 μl of fibril solution having a concentration of 50 μg/ml in each well. The plate was then dried overnight by placing it uncovered in a 37° C. incubator.

The ELISA assay was then performed as follows within 48 hours of preparing the plate. The wells were blocked by the addition of 100 μl of I % BSA in PBS and incubated for 1 hour at room temperature on a shaker. The plate was washed ×3 in PBS, 0.05% Tween 20 (v/v). To each well of the plate was added 50 μl of a solution of c11-1F4 (3 μg/ml antibody in 0.1% BSA/PBS) and the plate incubated at room temperature for 1 hour on a shaker. The plate was again washed ×3 (as before) and detection of bound antibody was accomplished using a biotinylated goat anti-mouse IgG antibody (Sigma #B-8774, anti-heavy and light-chain).
Results Sequence analysis of the successfully modified $V_H$ and $V_K$ genes revealed the correct sequence was present. Detailed DNA and amino acid sequences of the modified 11-1F4 $V_K$ and $V_H$ genes are presented in FIGS. 3 & 4. The modified $V_K$ and $V_H$ genes were successfully cloned into the mammalian expression vectors pG1D200 and pKN100 respectively, and the resulting 11-1F4VK.pKN100 and 11-1F4VHpG1D200 constructs were used for cotransfection of mammalian cells.

The 11-1F4VK.pKN100 and 11-1F4VHpG1D200 constructs were also subsequently used to construct a single supervector (pG1KD200-11-1F4), which expressed the chimeric 11-1F4 antibody in mammalian cells. The chimeric II-1F4 antibody expression levels, from both cotransfections and supervector transfections of ECACC COS cells were assayed. The expression levels observed from the pG1KD200-11-1F4 supervector transfections (10326 ng/ml) were 3.7 fold higher than the levels observed from the corresponding co-transfections of the 11-1F4VK.pKN100 and 11-1F4VHpG1D200 constructs (2820 ng/ml).

Figure 8:
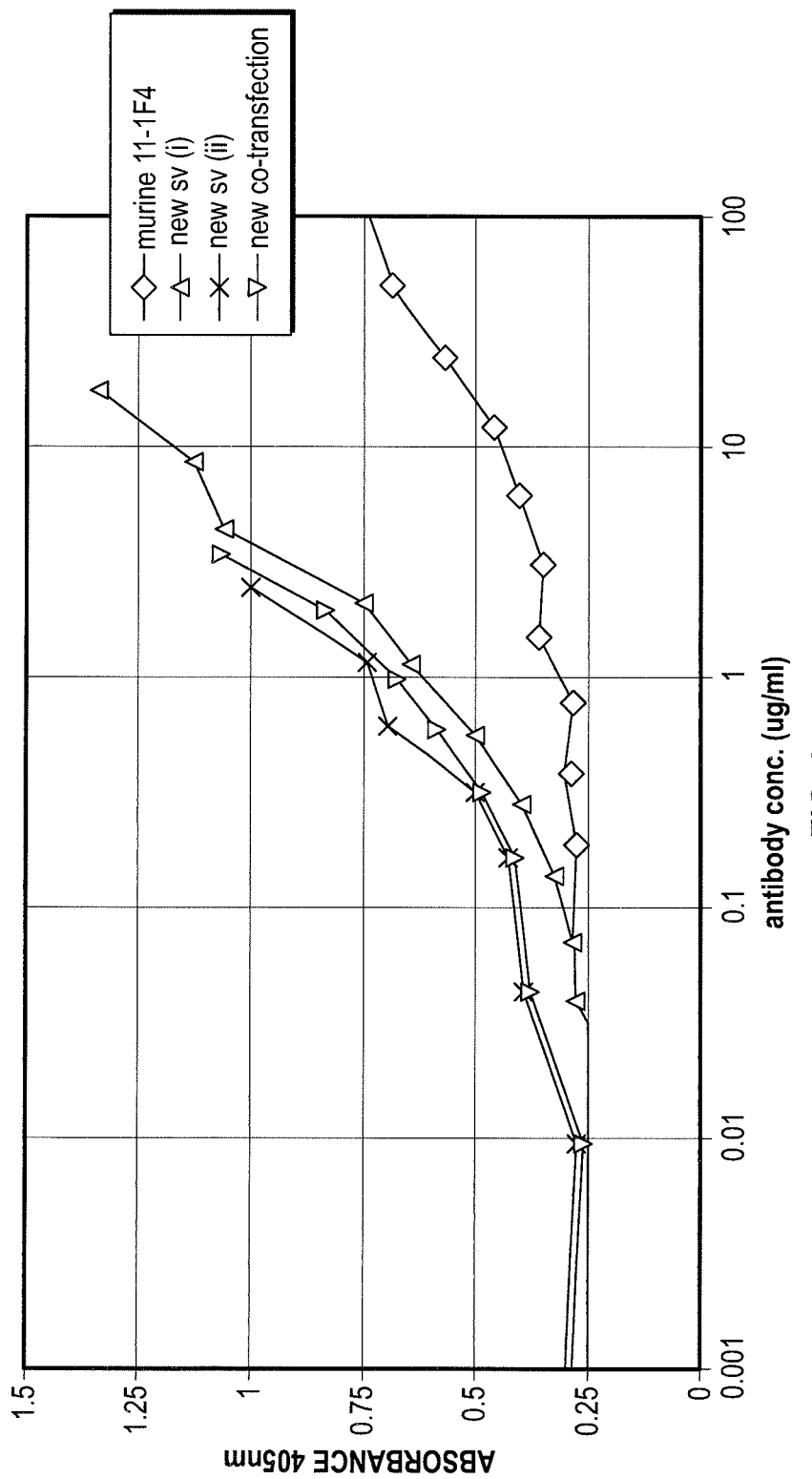
FIG. 8 is a graphical representation of the result of the amyloid fibril binding ELISA assay. The cos cell supernatants containing chimeric 11-1F4 antibody were tested separately on the same ELISA plate along with purified murine 11-1F4 antibody. The absorbance was read at OD405. New sv=pG1KD200-11-1F4. New co-transfection=11-1F4VHpG1D200 plus 11-1F4VK. pKN100.

Following expression and quantification, the chimeric 11-1F4 antibody was tested for binding to target antigen (amyloid fibrils kindly supplied by the NCI) by direct binding ELISA. The results of the binding ELISA are presented in FIG. 8. Supernatants from the two best individual pG1KD200-11-1F4 supervector transfections were assayed in parallel with one supernatant from the corresponding co-transfection.

The results indicated that the chimeric 11-1F4 antibody bound to the amyloid fibrils with a higher affinity than its murine equivalent. This result is surprising and unexpected because normally a chimeric antibody would be expected to have a binding affinity comparable to the original murine antibody. Without intending to be bound by the particular mechanism, the inventors believe it is possible that the net effect of combining the 11-1F4 murine V regions with the human γ1/κ C regions used to create the chimeric 11-1F4 antibody produced an antibody of higher affinity.

Samples of CHO cells (identified as CAEL-101) that secrete the chimeric 11-1F4 monoclonal antibody used herein were deposited with the American Type Culture Collection (ATCC Acc. NO: PTA-125146) on Jun. 27, 2018, in compliance with the Budapest Treaty.

Example 7

Mouse Amyloidoma Study with Murine 11-1F4

Amyloids were extracted from humans and characterized. Briefly, 30 to 40 g of fresh-frozen (−80° C.) or 10 g of lyophilized spleen or liver obtained postmortem from patients with AL amyloidosis were homogenized in ~300 ml of cold saline with a Virtis-Tempest apparatus (Virtis, Gardiner, N.Y.). The homogenates were centrifuged at 6° C. for 30 minutes at 17,000 rpm and residual saline-soluble material was removed by repeated homogenization and washing until the resultant supernatant had an OD of <0.10 at $A_{280}$. The pellet was then repeatedly homogenized, washed with cold deionized water, centrifuged, and the amyloid-containing supernatants lyophilized. The amount of protein recovered represented approximately one-third to one-fifth the weight of the starting material. The light chain composition and VL subgroup of the amyloid was determined by amino acid sequencing (Procise Protein Sequencing System; Applied Biosystems, Foster City, Calif.) and ionizing mass spectroscopy (PE SCIEX API 150 EX; Perkin Elmer, Norwalk, Conn.) of high-performance liquid chromatography-separated peptides obtained by trypsin digestion of reduced and pyridylethylated protein extracted from the water-soluble material with 6 mol/L guanidine HCl. The presence of the proteoglycan heparan sulfate was established using an Azure Aassay.

The composition of the amyloid extracts was established by chemical, immunoblotting, amino acid sequence, and ionizing mass spectroscopic analyses where the predominant protein species were found to be κ or λ light chain-related molecules that, in most cases, consisted primarily of the variable region (VL) plus the first ~50 residues of the constant region (CL) and, in others, VL fragments or intact molecules. Additionally, these extracts contained the expected amyloid-associated P-component, as well as the proteoglycan heparin sulfate.

Lyophilized water-soluble amyloid extracts were suspended in 25 ml of sterile saline and homogenized with a PCU-2 Polytron apparatus (Brinkman, Luzerne, Switzerland). The fibrils were sedimented by centrifugation at 6° C. for 30 minutes at 17,000 rpm; the resultant pellet was resuspended in 1 ml of sterile saline and rehomogenized. This solution was injected subcutaneously between the scapulae of BALB/c, CD-18 null, and C.B-17 SCID mice using an 18-gauge needle attached to a 6-ml syringe. The size of the resultant amyloidoma was measured by daily palpation and confirmed at necroscopy. High-resolution X-ray-computed tomography images were acquired using a microCat apparatus (Oak Ridge National Laboratory, Oak Ridge, Tenn.).

The injected material formed a readily visible, palpable mass on the backs of animals, the size of which depended on the amount of material injected (e.g., 0.2 to 2.5 cm in maximum diameter). The amyloidoma remained localized and unchanged for ~10 to 24 days, as evidenced by high-resolution X-ray-computed tomography; after that point, the amyloidomas began to regress and eventually disappeared throughout an ~4-day period. This response occurred regardless of the κ or λ nature or the VL subgroup of the amyloid extract; however, in studies involving five different κ and seven λ amyloidomas, ALλ extracts typically resolved more slowly than did ALκ (ALλ, 18+/−6 days versus ALκ, 13+/−3 days). Sufficient material was available to repeat experiments at least four times in eight of the 12 cases where it was found that this effect was reproducible in healthy, young animals regardless of the tissue source of the amyloid. However, dissolution of the induced amyloidomas was consistently delayed beyond 3 months in aged (>18 months) and immunodeficient mice.

Histological studies to determine the fate of the regressing amyloidomas demonstrated that the amyloid was not redistributed to other mouse tissues, as evidenced by Congo red staining. Additionally, the amyloidomas were infiltrated by naphthol AS-D chloroacetate-positive, a-naphthyl acetate-negative, polymorphonuclear cells, i.e., neutrophils. In contrast, this cellular response did not occur in CD-18 null mice where resolution of human AL amyloidomas required a considerably longer time period (i.e., 3 months). Further, amyloidolysis was delayed in animals rendered profoundly neutropenic by co-administration of 250 mg of the anti-neutrophil mAb Gr-1 given at the time of amyloidoma induction and again on day 3.

Amyloid removal also was dependent on a humoral murine response to the human light-chain-containing material. Approximately 10 to 20 days after amyloidoma induction, we showed in immunoblotting experiments that mouse sera contained antibodies that recognized, not only the light chain constituent of the amyloid protein injected, but also that of heterologous ALκ or ALλ extracts. In contrast, there was no reactivity with the homologous amyloid precursor protein, i.e., Bence Jones protein or any other monoclonal light chain tested. When the same amyloid preparation was re-administered to these immunized animals, its rate of disappearance increased approximately twofold.

To test the therapeutic efficacy of murine 11-1F4, a series of experiments were initiated in which 100-μg doses of the antibody were given to pairs of mice bearing human AL amyloidomas. In the case of ALκ, studies involving two different extracts revealed that even a single injection of the antibody resulted in rapid and complete disappearance of the amyloid tumor, as compared to untreated animals (Table 7; FIG. 9). The mass of an ALκλ amyloidoma was reduced >90% within 4 days after antibody injection, as compared to control animals. However, to achieve a similar response in certain ALλ-type amyloidomas, multiple doses of the reagent were required. These were given as a series of 100-μg injections beginning at the time when the amyloidoma was induced (day 0) and then again on days 2, 4, and 6 (FIG. 9B). As summarized in Table 7, in experiments in which five different human ALλ amyloidomas were tested in the mouse model, it was found that treatment with 11-1F4 decreased by as much as fourfold the time in which the amyloid tumors were eliminated. Notably, although single or repeated doses of two other anti-light chain mAbs that recognized AL fibrils (e.g., 31-8C7) expedited amyloidolysis, the 11-1F4 reagent was unique in that it accelerated removal of both ALκ and ALλ amyloid, albeit at different rates. In contrast, three other anti-light chain mAbs that were tested lacked such activity.

TABLE 7

Treatment of Mice with Human Amyloidomas with Murine 11-1F4

| Amyloidoma (V$_L$ subgroup) | Single dose* Treated 11-1F4‡ | Single dose* Treated 31-8C7‡ | Untreated | Multiple doses† Treated 11-1f4 | Multiple doses† Treated 31-8C7 | Untreated |
|---|---|---|---|---|---|---|
| ALκ(1) HIG | 4§ | 12 | 14 | NT¶ | NT | NT |
| ALκ(1) GRA | 4 | 8 | 15 | NT | NT | NT |
| ALκ(6) JON | 8 | 11 | 14 | NT | NT | NT |
| ALλ(1) SHE | 9 | 19 | 21 | 9 | 20 | 24 |
| ALλ(1) FIE | 17 | 24 | 24 | 9 | 18 | 26 |
| ALλ(2) BUE | 24 | NT | 25 | 6 | NT | 25 |
| ALλ(3) BAL | 28 | NT | 28 | 7 | NT | 28 |

*100 μg day 0;
†100 μg days 0, 2, 4, and 6;
‡mAb designation;
§time (days);
¶NT, not tested.

It was also determined that 11-1F4 recognized other forms of amyloid, as evidenced in immunohistochemical analyses of AA-, ATTR-, ALyS-, AApoA1-, and Aβ-containing tissues. In each case, similar patterns of reactivity were obtained with 11-1F4 and antibodies specific for these five different types of amyloid proteins.

Example 8

Phase 1a/b Study of the Chimeric 11-1F4 Antibody

GMP-grade amyloid fibril-reactive Chimeric IgG1 mAb 11-1F4 was produced by NCI's Biological Resource Branch for a phase 1a/b trial treating patients with refractory AL amyloidosis. The CHO cell line producing the chimeric IgG1 mAb 11-1F4 is identified as CAEL-101.

Relapsed or refractory AL Amyloidosis patients who received prior anti-plasma cell treatment were enrolled. Patients received chimeric IgG1 mAb 11-1F4 as a single intravenous infusion (phase 1a) or a series of weekly infusions for 4 weeks (phase 1b). A dose-escalation "up and down" design was used for both phase 1a and 1 b where successive doses of 0.5, 5, 10, 50, 100, 250 and 500 mg/m$^2$ were administered.

The primary objective of the study was to establish the maximum tolerated dose of chimeric 11-1F4, and secondary objectives included: (1) demonstrating a reduction in amyloid burden as evidenced by a decrease in affected organomegaly and/or improved organ function; (2) determining the pharmacokinetics of 11-1F4 when given as a single IV infusion (phase 1a) or as a series of weekly IV infusions (phase 1 b); and (3) determining the difference between 250 mg/m$^2$ and 500 mg/m$^2$ doses.

Key inclusion criteria included being 21 years of age or older, the patient had previously received systemic therapy, the patient did not require plasma cell targeted therapy, and the patient had an Eastern Cooperative Oncology Group (ECOG) performance status of less than or equal to 3.

Key exclusion criteria included intraventricular septum of greater than 2.5 mm, creatine clearance less than 30 cc/min, alkaline phosphatase more than 3 times the institutional upper limit of normal, and bilirubin higher than 3.0 mg/dL.

For the Phase 1a study, dose escalation followed an "up and down design." Once tolerated, successive patients each received progressively higher doses of chimeric 11-1F4 mAb, with two patients enrolled at a dose of 500 mg/m$^2$. Even the patients receiving the 500 mg/m$^2$ dose did not report any dose limiting toxicities. Patients were evaluated at week 0, dosed with chimeric 11-1F4 at week 1, and then reevaluated at weeks 2, 3, 4, and 8, as shown in FIG. 9A.

For the Phase 1 b study, infusions were given once a week for four weeks starting at 0.5 mg/m$^2$, Once tolerated, successive patients each received progressively higher doses of chimeric 11-1F4 mAb, with six patients enrolled at a dose of 500 mg/m$^2$. The dosing scheme is shown in FIG. 9B Results Twenty seven patients were treated with chimeric 11-1F4A antibody. Twenty six patients were evaluable for response. Eight patients completed phase 1a and nineteen patients completed treatment in phase 1 b. Median age for Phase 1a and 1b was 68. All patients tolerated the given dose of mAb chimeric 11-1F4 and up to the highest dose level of 500 mg/m$^2$ for both phase 1a and 1 b. There were no drug-related grade 4 or 5 adverse events (AEs) or dose-limiting toxicities. Two patients developed a grade 2 rash 3-4 days after infusion. One patient developed the skin rash in in phase 1a (dose level 4) and when he was retreated in phase 1 b. A skin biopsy with immunohistochemical staining showed chimeric 11-1F4 binding to amyloid fibrils with an concomitant neutrophilic infiltrate. The same patient and another patient developed a similar rash in phase 1b which further provides clinical and correlative data that chimeric 11-1F4 directly binds to light-chain amyloid fibrils. Overall, 63% (5 of 8) of evaluable patients demonstrated organ response after one infusion of mAb c11-1F4 in phase 1a. The median time to response in phase 1a was 4.5 weeks after completing therapy. In phase 1 b, 61% (11 of 18) of evaluable patients showed significant organ responses with a median time to response of 1 week after commencing therapy with the tendency of faster response in higher dosages The patient characteristics of a subset of the evaluable patients are shown in Table 8 below.

TABLE 8

Phase 1a/b Patient Characteristics

| Characteristic | Median | | | |
|---|---|---|---|---|
| Age (N = 21 patients) | 67 yrs (Range: 34-77) | | | |
| Gender | | Male | N = 15 | (68%) |
| | | Female | N = 6 | (32%) |
| Light Chain type | | λ | N = 13 | (52%) |
| | | K | N = 8 | (48%) |
| Revised Mayo Stage | II (Range: I to IV) | | | |
| Organ Involvement (No.) | 2 (Range: 1-4) | Heart | N = 11 | (52%) |
| | | Kidney | N = 11 | (52%) |
| | | Skin/Soft tissue | N = 10 | (48%) |
| | | GI | N = 8 | (38%) |
| | | Nervous system | N = 4 | (19%) |
| | | Liver | N = 3 | (14%) |
| | | Lung | N = 2 | (10%) |
| | | Musculoskeletal | N = 1 | (5%) |
| Best Hematologic Response to Therapy | | CR | N = 3 | (14%) |
| | | VGPR | N = 15 | (71%) |
| | | PR | N = 2 | (10%) |
| | | NR | N = 1 | (5%) |
| Previous Regimen (No.) | 2 (Range: 1-6) | | | |
| Baseline NT-proBNP (ng/L)[a] | 2359 (Range: 894-13,131) | | | |
| Baseline 24 hr Urine Protein (mg/24 hr)[b] | 4998 (Range: 1078-10,170) | | | |
| Time Since last Exposure to Chemotherapy (mos) | 6 (Range 1-51) | | | |

[a]Baseline NT-proBNP in patients with cardiac involvement who were evaluable for response (Baseline NT-proBNP ≥ 650 pg/mL)
[b]Baseline 24 hour urine protein in patients with renal involvement who were evaluable for response (Baseline 24 hour urine protein > 500 mg/24 h)

At the close of the Phase 1a/b studies, 18 patients had evaluable responses (N=1 had no measurable disease, N=2 did not complete treatment). Twelve of the 18 (67%) showed an improved organ response. Specifically, in the Phase 1a, 63% of patients (5 of 8) with measurable disease burden demonstrated organ response after one infusion of mAb 11-1F4 (2 renal, 2 cardiac, and 1 GI). In the Phase 1 b study, 70% of patients (7 of 10) with measurable disease burden showed organ response: 3 of 4 patients who were evaluated for response with cardiac involvement showed cardiac response; 4 of 4 patients who were evaluated for response with renal involvement showed renal response; 1 patient with GI response was evaluated; and 1 patient with soft tissue response showed an improvement of arthritis from ° 3→4° 1.

Cardiac Response

Figure 11:
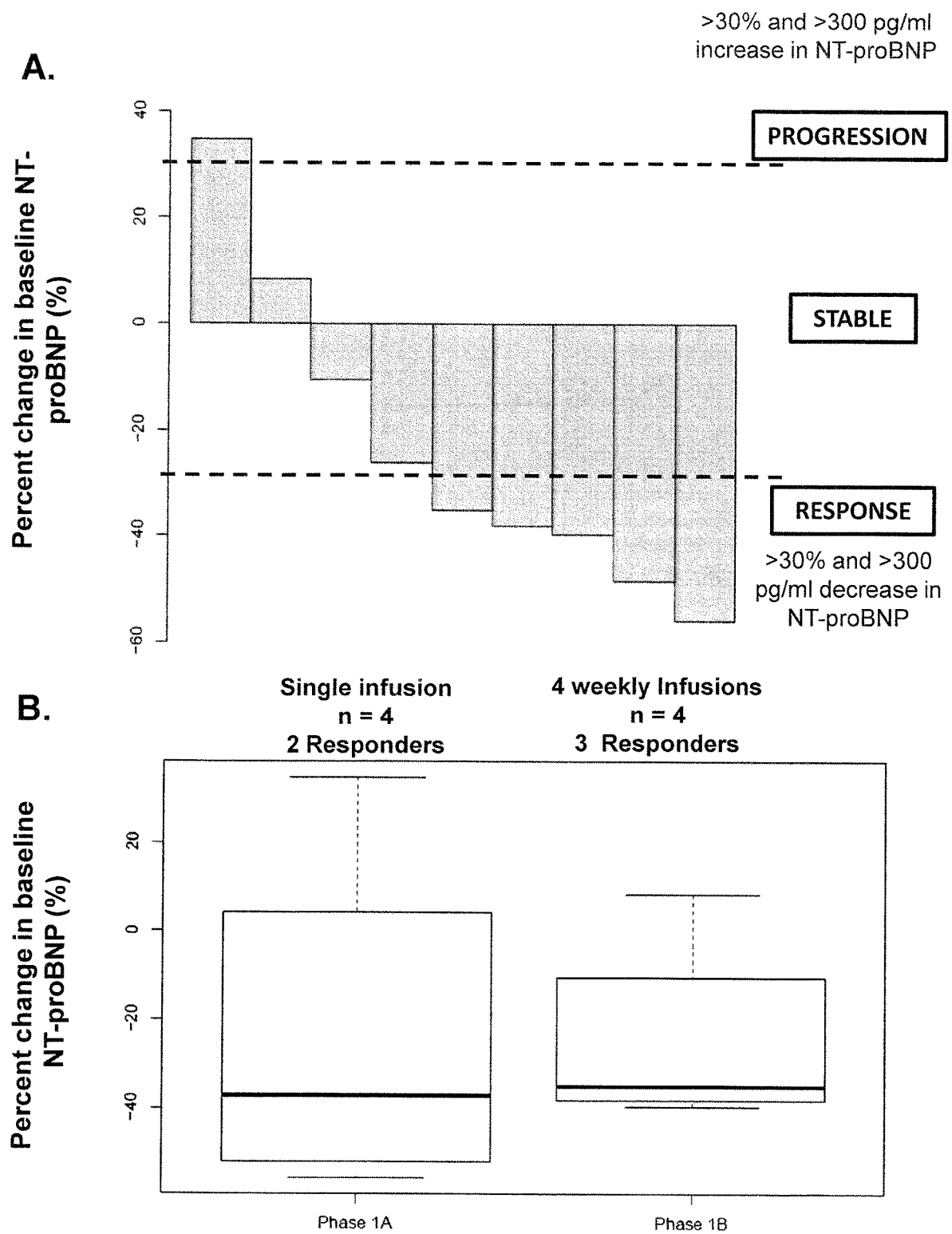
FIG. 11 shows that administration of chimeric 11-1F4 provides an improvement in cardiac function in most patients. Panel A shows the results from a Phase 1a/b trial in a bar graph, and Panel B shows the results as a box plot.
Figure 12:
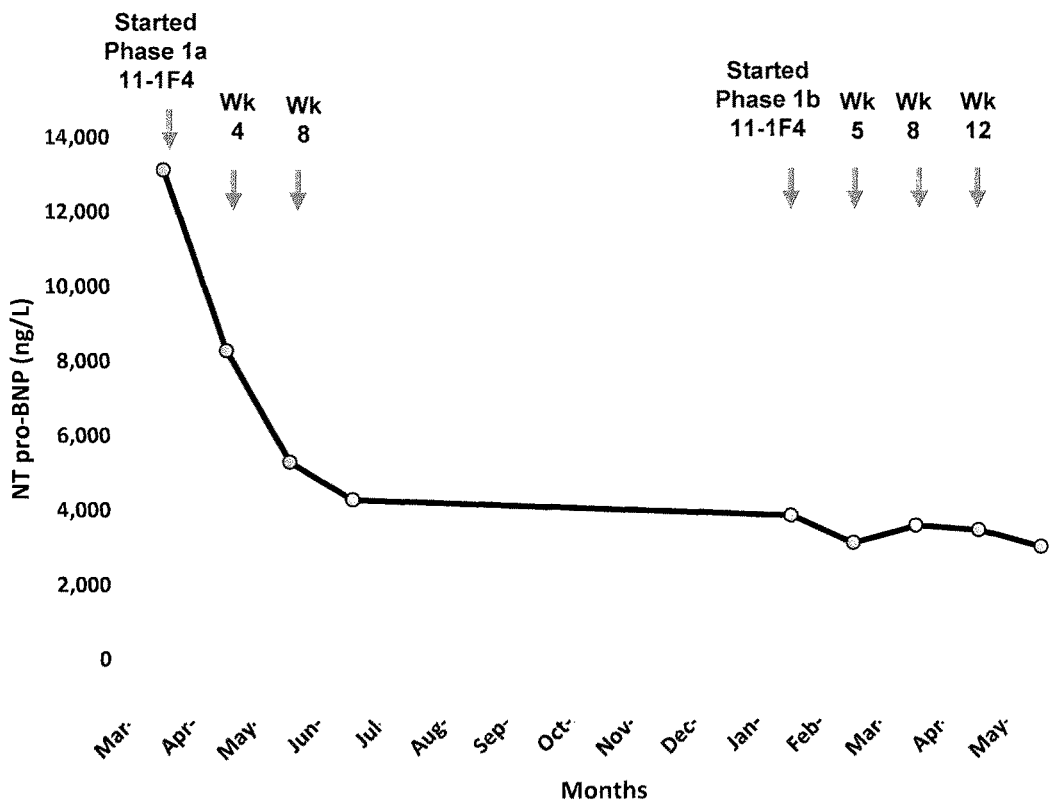
FIG. 12 shows cardiac response (NT-proBNP) in an exemplary patient during Phase 1a/b clinical trial of c11-1F4 antibody.

Eight patients were evaluated for cardiac response. Among the metrics that were evaluated were NT-proBNP and NYHA class criteria. The baseline level for all of these patients was ≥650 pg/ml. Five of the patients (63%) showed a significantly improved response (i.e., a ≥30% decrease in NT-proBNP and/or shifting from NYHA class III to class I), 2 patients remained stable, and only one showed any sign of disease progression. The cardiac results for the groups of patients are shown in FIG. 11. The decrease in NT-proBNP for one exemplary patient is shown in FIG. 12.

Renal Response

Eight patients were evaluated for renal response, with proteinuria being the primary metric for determining responsiveness. Six patients (75%) showed a significantly improved response (i.e., a ≥30% decrease in proteinuria or a decrease to <0.5 g/24 hours in the absence of renal progression), and two patients remained stable. No patients showed signs of renal disease progression (>25% worsening in eGFR). The renal results for the groups of patients are shown in FIG. 13. The decrease in proteinuria for one exemplary patient is shown in FIG. 14.

Study Overview of Results

Treatment with chimeric 11-1F4 was well tolerated and safe. There were no drug related grade 4 or 5 adverse events (AEs) or dose limiting toxicity up to an MTD of 500 mg/m$^2$. Moreover, chimeric 11-1F4 is clinically efficacious. Most patients saw an early and sustained organ response even as a single infusion or as a weekly infusion for 4 weeks. Improved responses were observed across tissues/organs, including cardiac, renal, GI, skin, and soft tissue responses. Indeed, chimeric 11-1F4 safely promotes amyloid resolution in 67% of the patients and leads to improvement in organ function after just a single dose, even in patient with ALλ deposits. Patient response to chimeric 11-1F4 was rapid and sustained. Indeed, with median response time of 4.5 weeks in the Phase 1a trial and just one week in the Phase 1b trial, chimeric 11-1F4 provides a positive response faster than any other known therapeutic targeting amyloid fibrils. The rapid destruction of amyloid fibrils by chimeric 11-1F4 can improve organ function and, by extension, significantly improve mortality in patients with this uniformly fatal disease.

Example 9

Cardiac Response to Chimeric Fibril-Reactive Monoclonal Antibody 11-1F4 in Patients with AL Amyloidosis with Global Longitudinal Strain: Results from the Phase 1b Trial An open-label phase 1 b clinical trial of the chimeric 11-1F4 mAb was completed with promising results as shown below. This study was undertaken to assess the response of myocardial function to mAb administration using global longitudinal strain (GLS).

Nineteen patients with relapse or refractory AL Amyloidosis were enrolled into the trial (age±SD, 63±12; 68% male). Fifty three percent had light chain kappa amyloid and 52% had cardiac involvement as defined by NTpro-BNP level of >650 pg/ml. NTpro-BNP screening and baseline levels of the nineteen patients are shown in Table 9 below. These cardiac patients included 2 patients who were not in the cardiac evaluable primary clinical analysis, due to differences in Screening vs Baseline NT-proBNP values.

TABLE 9

NTpro-BNP Screening and Baseline Values of Echocardiographic Analysis

| Visit | Statistics | All Phase 1B patients | Cardiac involvement | Cardiac Evaluable |
|---|---|---|---|---|
| Screening | n | 19 | 10 | 8 |
| | Mean (SD) | 992.81 (1067.07) | 1681.4 (1067.12) | 1846.9 (1127.46) |
| | Median | 662.20 | 1186.6 | 1592.6 |
| | Min, Max | 39.7, 3964.0 | 662.2, 3964.0 | 850.1, 3964.0 |
| Baseline (Week 1) | n | 19 | 10 | 8 |
| | Mean (SD) | 897.95 (1067.81) | 1560.9 (1114.99) | 1796.9 (1131.27) |
| | Median | 589.70 | 986.40 | 1261 0 |
| | Min, Max | 44.1, 3810.0 | 589.7, 3810.0 | 815.5, 3810.0 |

The mAb was administered weekly for 4 weeks with sequential doses of 0.5, 5, 10, 50, 100, 250 and 500 mg/m$^2$ in a dose-escalation design. Clinical echocardiographic (ECHO) examinations at baseline and 12 weeks post therapy were compared. Several echocardiographic variables including left ventricular ejection fraction (LVEF) (calculated using Simpson's biplane method) and global longitudinal strain (GLS) were obtained. GLS was measured using speckle-tracking (TomTec-Arena 1.2, Germany) and calculated as an average of 4-, 2-, and 3-chamber based measurements. Paired student's t-test was used to compare echocardiographic variables at baseline and 12 weeks after therapy with mAb. The analysis of the echocardiogram parameters are demonstrated in Table 10 below.

TABLE 10

The analysis of the echocardiographic parameters

| Number Patients | Screening 10 | Week 12 10 | P-value |
|---|---|---|---|
| lvidd_cm (mean (sd)) | 4.38 (0.93) | 4.32 (0.91) | 0.319 |
| ivs_cm (mean (sd)) | 1.29 (0.22) | 1.21 (0.18) | 0.119 |
| pwt_cm (mean (sd)) | 1.12 (0.27) | 1.14 (0.25) | 0.217 |
| lved_mass_g (mean (sd)) | 187.86 (43.37) | 179.30 (42.87) | 0.197 |
| ef_percent (mean (sd)) | 51.95 (9.92) | 52.28 (11.59) | 0.856 |
| mcf (mean (sd)) | 0.37 (0.11) | 0.38 (0.13) | 0.626 |
| mv_e_m_s (mean (sd)) | 8.53 (24.18) | 0.94 (0.37) | 0.347 |
| mv_a_m_s (mean (sd)) | 13.45 (34.05) | 0.72 (0.23) | NA |
| gls_percent (mean (sd)) | −15.68 (4.14) | −17.37 (3.53) | 0.004 |

While there was neither significant change between LVEF (56.2±8.6% vs. 56.2±9.5%, p=0.985) nor GLS (−19.04±−5.11% vs. −19.73±−4.1%, p=0.119) from baseline to 12 week examinations for the overall cohort, patients with cardiac involvement demonstrated an improvement in GLS (−15.58±−4.14% pre and −17.37±−3.53% post, p=0.004 as visualized in FIG. 15. An exemplary echocardiogram of a patient with cardiac involvement before treatment and at week 12 post treatment with chimeric 11-1F4 mAb is shown in FIG. 17. The patient shown in FIG. 17 had a baseline level of NT-proBNP of 2549 pg/mL and a GLS value of −9.58 before treatment. After 12 weeks of chimeric 11-1F4 mAb treatment, the patient exhibited reduction in GLS to −13.39, and a reduction in NTproBNP to 1485 pg/mL. Subgroup analysis showed an improvement in GLS in patients with lambda amyloid cardiac involvement (−14.3±−4.38% pre and −16.17±−3.74% post, p=0.02) and a trend in improvement with kappa amyloid cardiac involvement (−16.60±−4.10% pre and −18.16±−3.48% post, p=0.07). Furthermore, the Cardiac Evaluable Population as defined in the clinical analysis of the study (using the Baseline NT-proBNP values rather than the Screening Values) also resulted in a statistically significant decrease in GLS % (p-value 0.0163), with a numerically similar decrease (−1.71) as the analysis provided by the ECHO group (−1.69). Table 11 below shows the analysis of decrease in the GLS in cardiac patients versus cardiac evaluable patients and non-cardiac patients.

TABLE 11

Comparison of Cardiac Patients per Screening vs Baseline Evaluable Definitions and Non Cardiac Patients.

| | Number Patients | Baseline | Follow-up | P-value |
|---|---|---|---|---|
| GLS % Mean (Std Dev) | 10 (Cardiac Patients per Screening NT-proBNP) | −15.68 (4.14) | −17.37 (3.53) | 0.004 |
| | 8 (Cardiac Evaluable per Baseline: NT-proBNP) | −14.95 (4.32) | −16.66 (3.55) | 0.0163 |
| | 9 (Non-Cardiac Patients per Semening NT-proBNP) | −22.77 (3.12) | −22.36 (3.02) | 0.4829 |

In conclusion, this trial shows a significant improvement in GLS after exposure to an anti-fibril specific mAb in subjects with AL amyloid cardiac involvement. As shown in FIG. 15, 9 out of 10 patients with cardiac involvement improved on GLS %. The probability that 9 or more patients improving, under the null hypothesis that there is no drug effect, is ~0.0107, suggesting that observing 9 of 10 patients improving is a highly unlikely outcome unless the drug truly is effective. This preliminary data will aid in designing a larger clinical trial. Additionally, larger trials leveraging GLS to evaluate myocardial function are warranted.

Example 10

Organ Response to Chimeric Fibril-Reactive Monoclonal Antibody 11-1F4 in Patients Who are not Controlled Hematologically.

A patient that had received 6 chemotherapy treatments and had achieved a hematologic partial response on those treatments with no organ response was administered the chimeric amyloid fibril-reactive monoclonal antibody (mAb) 11-1F4. For three consecutive periods post-dose, there was consistent reduction in NT-proBNP after receiving 11-1F4, and the patient achieved an organ response as described in FIG. 16. But when taken off of antibody, free light chains increased and the patient condition worsened. Organ progression was then seen after completion of the trial. The response pattern of this patient led the investigators to conclude that organ response was due to the chimeric 11-1F4 antibody treatment and independent of chemotherapy induced hematologic response.

In the description and claims of this specification the word "comprise" and variations of that word, such as "comprises" and "comprising" are not intended to exclude other features, additives, components, integers or steps but rather, unless otherwise stated explicitly, the scope of these words should be construed broadly such that they have an inclusive meaning rather than an exclusive one.

Although the compositions and methods of the invention have been described in the present disclosure by way of illustrative examples, it is to be understood that the invention is not limited thereto and that variations can be made as known by those skilled in the art without departing from the teachings of the invention defined by the appended claims.

What is claimed is:

1. A method of treating primary amyloidosis in a human patient in need of such treatment comprising:
   administering to the patient multiple therapeutically effective doses of a pharmaceutical composition comprising a chimeric mouse-human antibody comprising a $V_K$ region comprising SEQ ID NO: 47 and a $V_H$ region comprising SEQ ID NO: 48;
   measuring N-terminal pro b-type natriuretic peptide (NT-proBNP) in the patient prior to administering the antibody to determine a baseline level and measuring NT-proBNP over a time frame of about 12 weeks, wherein a level of NT-proBNP that is reduced by at least about weeks 4 to 12 after administration by at least about 30% as compared with baseline levels prior to administration is indicative of responsiveness to the treatment; and
   measuring the patient's global longitudinal strain (GLS) level prior to administering the antibody to determine a baseline level and measuring GLS over a time frame of about 12 weeks, wherein a level of GLS that is reduced by at least about 1.79%, as calculated by the Lagrangian formula, as compared to baseline levels prior to administration is indicative of responsiveness to the treatment,
   optionally measuring are patient's urine protein level, wherein a decrease in protein in the urine by at least about 30% compared to baseline levels prior to administration of the antibody is indicative of responsiveness to the treatment, thereby treating the amyloidosis in the subject.

2. The method of claim 1, wherein the chimeric antibody is administered in doses of about 500 mg/m² or less.

3. The method of claim 1, wherein the therapeutically effective doses of the chimeric antibody are each about 2,200 mg.

4. The method of claim 1, wherein the therapeutically effective doses of the chimeric antibody are each about 1-50 mg/kg.

5. The method of claim 4, wherein the effective doses of the chimeric antibody are each about 5-40 mg/kg or 10-30 mg/kg.

6. The method of claim 1, wherein the primary amyloidosis comprises involvement of at least one organ or tissue selected from the group consisting of heart, kidneys, liver, lung, gastrointestinal tract, nervous system, muscular skeletal system, soft tissue, and skin.

7. The method of claim 6, wherein the primary amyloidosis comprises involvement of the heart.

8. The method of claim 6, wherein the primary amyloidosis comprises involvement of the kidneys.

9. The method of claim 8, wherein the doses are effective to reduce the patient's urine protein level by at least about 30% compared to baseline levels prior to administration of the chimeric antibody.

10. The method of claim 8, wherein the doses are effective to reduce the patient's urine protein level by at least about 40% compared to baseline levels prior to administration of the chimeric antibody.

11. The method of claim 8, wherein the doses are effective to reduce the patient's urine protein to less than about 7000 mg/24 hours following administration of the chimeric antibody.

12. The method of claim 8, wherein the doses are effective to reduce the patient's urine protein to less than about 6000 mg/24 hours following administration of the chimeric antibody.

13. The method of claim 8, wherein the doses are effective to reduce the patient's urine protein to less than about 5000 mg/24 hours following administration of the chimeric antibody.

14. The method of claim 8, wherein the doses are effective to reduce the patient's urine protein to less than about 4000 mg/24 hours following administration of the chimeric antibody.

15. The method of claim 1, wherein the doses are effective to produce a therapeutic response in less than about 5 weeks following administration.

16. The method of claim 1, wherein the doses are effective to reduce the patient's N-terminal pro b-type natriuretic peptide (NT-proBNP) level to less than about 9100 ng/L by about 8 weeks following administration of the chimeric antibody.

17. The method of claim 1, wherein the doses are effective to reduce the patient's N-terminal pro b-type natriuretic peptide (NT-proBNP) level to less than about 8000 ng/L by about 8 weeks following administration of the chimeric antibody.

18. The method of claim 1, wherein the doses are effective to reduce the patient's N-terminal pro b-type natriuretic peptide (NT-proBNP) level to less than about 7000 ng/L by about 8 weeks following administration of the chimeric antibody.

19. The method of claim 1, wherein the doses are effective to reduce the patient's N-terminal pro b-type natriuretic peptide (NT-proBNP) level to less than about 6000 ng/L by about 12 weeks following administration of the chimeric antibody.

20. The method of claim 1, wherein the doses are effective to reduce the patient's N-terminal pro b-type natriuretic peptide (NT-proBNP) level to less than about 5000 ng/L by about 12 weeks following administration of the chimeric antibody.

21. The method of claim 1, wherein the patient was classified as Previously Presented York Heart Association (NYHA) Functional Classification class II or III prior to administration of the chimeric antibody and is classified as class I following administration of the chimeric antibody.

22. The method of claim 1, wherein administration of the chimeric antibody does not cause any serious adverse events.

23. The method of claim 1 wherein the chimeric antibody is administered once weekly for four weeks.

24. The method of claim 1, wherein the chimeric antibody is administered in doses of about 10-1000 mg/m².

25. The method of claim 24, wherein the chimeric antibody is administered in doses of about 750 mg/m2 or about 1000 mg/m².

26. The method of claim 1, wherein the therapeutically effective doses of the chimeric antibody are each between about 50 and 5000 mg, between 60 about 4500 mg, between 70 and 4000 mg, between 80 and 3500 mg, between 90 and 3000 mg, between 100 and 2500 mg, between 150 and 2000 mg, between 200 and 1500 mg, or between 250 and 1000 mg.

27. The method of claim 1, wherein the GLS is improved by at least about 2%.

28. A method of treating a patient with primary light chain (AL) amyloidosis involving the heart comprising:
  a) administering to said patient multiple therapeutically effective doses of an antibody which comprises a $V_K$ region comprising SEQ ID NO: 47 and a $V_H$ region comprising SEQ ID NO: 48; b) measuring N-terminal pro b-type natriuretic peptide (NT-proBNP) in the patient prior to administering the antibody to determine a baseline level and measuring NT-proBNP over a time frame of about 12 weeks, wherein a level of NT-proBNP that is reduced by at least about weeks 4 to 12 after administration by at least about 30% as compared with baseline levels prior to administration is indicative of responsiveness to the treatment; and
  c) measuring the patient's global longitudinal strain (GLS) level prior to administering the antibody to determine a baseline level and measuring GLS over a time frame of about 12 weeks, wherein a level of GLS that is reduced by at least about 1.79%, as calculated by the Lagrangian formula, as compared to baseline levels prior to administration is indicative of responsiveness to the treatment, thereby treating the amyloidosis involving the heart.

29. The method of claim 28, wherein the AL amyloidosis is refractory.

30. The method of claim 28, wherein the doses are effective to produce a therapeutic response in less than 5 weeks following administration.

31. The method of claim 28, wherein the doses are effective to produce a therapeutic response within about a week or less following administration.

32. The method of claim 28, wherein the effective doses of the antibody are each 500 mg/m² or less.

33. The method of claim 28, wherein the effective doses of the antibody are each about 2,200 mg.

34. The method of claim 28, wherein the effective doses of the antibody are each about 1-50 mg/kg.

35. The method of claim 1 or 28 in which the doses are effective to reduce NT-proBNP levels, which are sustained in the patient for at least about three or about six months after the administration of the antibody.

36. The method of claim 28, wherein the antibody is administered once weekly for four weeks.

37. The method of claim 1 or 28, wherein the antibody comprises a constant region derived from a human IgG1.

38. A method of treating a patient with primary light chain (AL) amyloidosis involving the kidneys comprising: a) administering to said patient multiple therapeutically effective doses of an antibody comprising a $V_K$ region comprising SEQ ID NO: 47 and a $V_H$ region comprising SEQ ID NO: 48; and b) measuring protein levels in urine from the patient, wherein an effective treatment is determined by a reduction in proteinuria in said patient by at least 40% by at least about 8 weeks following administration of the antibody as compared to a pre-treatment baseline level.

39. The method of claim 38, wherein the AL amyloidosis is refractory.

40. The method of claim 38, wherein the antibody comprises a constant region derived from a human IgG1.

41. The method of claim 38, wherein the doses are effective to produce a therapeutic response in less than 5 weeks following administration.

42. The method of claim 38, wherein the doses are effective to produce a therapeutic response within about a week or less following administration.

43. The method of claim 38, wherein the effective doses of the antibody are each 500 mg/m² or less.

44. The method of claim 38, wherein the effective doses of the antibody are each about 2,200 mg.

45. The method of claim 38, wherein the effective doses of the antibody are each about 1-50 mg/kg.

46. The method of claim 38, wherein the doses are effective to reduce proteinuria in the patient for at least about six months after the administration of the chimeric antibody.

47. The method of claim 38, wherein the antibody is administered once weekly for four weeks.

48. A method of decreasing the amount of kappa and/or lambda light chain fibril aggregate deposits in a human patient with primary amyloidosis with kappa or lambda light chain fibril aggregate deposits comprising: a) administering to said patient multiple therapeutically effective fibril aggregate deposit reducing doses of an antibody comprising:
  a. a $V_K$ region comprising SEQ ID NO: 47,
  b. a $V_H$ region comprising SEQ ID NO: 48, and
  c. a human IgG1 constant region;
b) measuring N-terminal pro b-type natriuretic peptide (NT-proBNP) in the patient prior to administering the antibody to determine a baseline level and measuring NT-proBNP over a time frame of about 12 weeks, wherein a level of NT-proBNP that is reduced by at least about weeks 4 to 12 after administration by at least about 30% as compared with baseline levels prior to administration is indicative of responsiveness to the treatment; and
c) measuring the patient's global longitudinal strain (GLS) level prior to administering the antibody to determine a baseline level and measuring GLS over a time frame of about 12 weeks, wherein a level of GLS that is reduced by at least about 1.79%, as calculated by the Lagrangian formula, as compared to baseline levels prior to administration is indicative of responsiveness to the treatment, thereby treating the amyloidosis or assessing responsiveness to the treatment thereby decreasing the amount of kappa and/or lambda light chain fibril aggregate deposits in the patient.

49. The method of claim 48, wherein the primary amyloidosis consists of lambda light chain fibril aggregate deposits.

50. The method of claim 48, wherein the primary amyloidosis consists of kappa light chain fibril aggregate deposits.

51. The method of claim 48, wherein the primary amyloidosis consists of kappa and lambda light chain fibril aggregate deposits.

52. The method of claim 48, wherein the doses are effective produce a therapeutic response in less than 5 weeks following administration.

53. The method of claim 48, wherein the effective doses of the antibody are each 500 mg/m² or less.

54. The method of claim 48, wherein the effective doses of the antibody are each about 2,200 mg.

55. The method of claim 48, wherein the effective doses of the antibody are each about 1-50 mg/kg.

56. The method of claim 48, wherein the doses are effective to decrease organ dysfunction in the patient.

57. The method of claim 48, wherein the antibody is administered once weekly for four weeks.

58. A method of improving myocardial function in a patient with amyloid light chain amyloidosis (ALA) with cardiac involvement comprising:
   a) administering to said patient in multiple therapeutically effective doses an amount of a humanized or chimeric antibody or an antigen-binding fragment thereof to improve the myocardial function of the patient, the antibody or antigen-binding fragment comprising:
   a variable heavy chain ($V_H$) comprising: a complementarity determining region (CDR) H1 comprising SEQ ID NO:52; a CDRH2 comprising SEQ ID NO: 53; and a CDRH3 comprising SEQ ID NO: 54; and
   a variable light chain ($V_K$) comprising a CDRL1 comprising SEQ ID NO: 49; a CDRL2 comprising SEQ ID NO: 50; and a CDRL3 comprising SEQ ID NO: 51;
   b) measuring N-terminal pro b-type natriuretic peptide (NT-proBNP) in the patient prior to administering the antibody to determine a baseline level and measuring NT-proBNP over a time frame of about 12 weeks, wherein a level of NT-proBNP that is reduced by at least about weeks 4 to 12 after administration by at least about 30% as compared with baseline levels prior to administration is indicative of responsiveness to the treatment; and
   c) measuring the patient's global longitudinal strain (GLS) level prior to administering the antibody to determine a baseline level and measuring GLS over a time frame of about 12 weeks, wherein a level of GLS that is reduced by at least about 1.79%, as calculated by the Lagrangian formula, as compared to baseline levels prior to administration is indicative of responsiveness to the treatment, thereby improving myocardial function in the patient.

59. The method of claim 58, wherein the antibody or antigen-binding fragment thereof is a humanized antibody.

60. The method of claim 58, wherein the improvement in myocardial function persists for at least 8 weeks after administration of the antibody or antigen-binding fragment thereof.

61. The method of claim 58, wherein the patient exhibits a pretreatment NT-proBNP level greater than 650 pg/mL.

62. The method of claim 58, wherein the doses are effective to reduce NT-proBNP levels by about 300 pg/mL or more compared to pretreatment NT-proBNP levels.

63. The method of claim 58, wherein the patient suffers from relapsed or refractory ALA.

64. The method of claim 58, wherein the ALA is further characterized as having light chain lambda amyloid cardiac involvement.

65. The method of claim 58, wherein the ALA is further characterized as having light chain kappa amyloid cardiac involvement.

66. The method of claim 58, wherein the ALA is not hematologically controlled.

67. The method of claim 58, wherein the humanized or chimeric antibody or antigen binding fragment thereof is administered once weekly for four weeks.

68. The method of any of claim 28, 38, 48, or 58, wherein the antibody or antigen-binding fragment thereof is a chimeric antibody.

69. The method of claim 68, wherein the $V_K$ region comprises SEQ ID NO: 47 and the $V_H$ region comprises SEQ ID NO: 48.

70. The method of claim 68, wherein the antibody comprises a constant region is derived from a human IgG1.

71. A method of treating amyloid light chain amyloidosis (ALA) with cardiac involvement in a patient, wherein the ALA is not hematologically controlled, the method comprising; a) administering to said patient with ALA characterized by cardiac involvement and a lack of hematological control in multiple therapeutically effective doses a therapeutically effective amount of a humanized or chimeric antibody or an antigen-binding fragment thereof comprising:
   a variable heavy chain ($V_H$) comprising: a complementarity determining region (CDR) H1 comprising SEQ ID NO: 52; a CDRH2 comprising SEQ ID NO: 53; and a CDRH3 comprising SEQ ID NO: 54; and
   a variable light chain ($V_K$) comprising a CDRL1 comprising SEQ ID NO: 49; a CDRL2 comprising SEQ ID NO: 50; and a CDRL3 comprising SEQ ID NO: 51,
   b) measuring N-terminal pro b-type natriuretic peptide (NT-proBNP) in the patient prior to administering the antibody to determine a baseline level and measuring NT-proBNP over a time frame of about 12 weeks, wherein a level of NT-proBNP that is reduced by at least about weeks 4 to 12 after administration by at least about 30% as compared with baseline levels prior to administration is indicative of responsiveness to the treatment; and
   c) measuring the patient's global longitudinal strain (GLS) level prior to administering the antibody to determine a baseline level and measuring GLS over a time frame of about 12 weeks, wherein a level of GLS that is reduced by at least about 1.79%, as calculated by the Lagrangian formula, as compared to baseline levels prior to administration is indicative of responsiveness to the treatment, thereby treating amyloid light chain amyloidosis (ALA) with cardiac involvement in the patient.

72. The method of claim 71, wherein the antibody or antigen-binding fragment thereof is a humanized antibody.

73. The method of claim 71, wherein the antibody or antigen-binding fragment thereof is a chimeric antibody.

74. The method of claim 73, wherein the $V_K$ region comprises SEQ ID NO: 47 and the $V_H$ region comprises SEQ ID NO: 48.

75. The method of claim 73, wherein the antibody comprises a constant region derived from a human IgG1.

76. The method of claim 71, further comprising administering a chemotherapeutic compound to the patient.

77. The method of claim 71, wherein the lack of hematological control comprises detectable circulating levels of amyloid precursor protein or wherein the difference between involved and uninvolved free light chains in the subject's serum is >40 mg/L.

78. The method of claim 71, wherein the improvement in GLS occurs within three weeks of being administered the antibody or antigen-binding fragment thereof.

79. The method of claim 71, wherein the improvement in GLS sustained for at least three months following administration of the antibody or antigen-binding fragment thereof.

80. The method of claim 71, wherein the ALA is further characterized as having light chain lambda amyloid cardiac involvement.

81. The method of claim 71, wherein the ALA is further characterized as having light chain kappa amyloid cardiac involvement.

82. The method of claim 71, wherein the humanized or chimeric antibody or antigen-binding fragment thereof is administered once weekly for four weeks.

83. A method of treating primary amyloidosis in a human patient in need of such treatment comprising administering to the patient a pharmaceutical composition comprising an antibody comprising a $V_K$ region comprising SEQ ID NO: 47 and a $V_H$ region comprising SEQ ID NO: 48 in a pharmaceutically acceptable carrier, wherein administering is in multiple therapeutically effective doses thereby reducing cardiac, renal, GI, skin, and soft tissue dysfunction.

84. The method of claim 83, wherein the antibody is administered in doses of about 500 mg/m$^2$ or less.

85. The method of claim 83, wherein the effective doses of antibody are each about 2,200 mg.

86. The method of claim 83, wherein the effective doses of the antibody are each about 1-50 mg/kg.

87. The method of claim 83, wherein the antibody is a chimeric antibody or a humanized antibody.

88. The method of claim 83, wherein the reduction in dysfunction is measured at more than one time point after at least 2 administrations.

* * * * *

SEQUENCE LISTING

<160> NUMBER OF SEQ ID NOS: 57

<210> SEQ ID NO 1
<211> LENGTH: 31
<212> TYPE: DNA
<213> ORGANISM: Mus musculus

<400> SEQUENCE: 1
atgaagattg cctgttaggc tgttggtgct g                                          31

<210> SEQ ID NO 2
<211> LENGTH: 31
<212> TYPE: DNA
<213> ORGANISM: Mus musculus

<400> SEQUENCE: 2
atggagwcag acacactccc tgytatgggt g                                          31

<210> SEQ ID NO 3
<211> LENGTH: 31
<212> TYPE: DNA
<213> ORGANISM: Mus musculus

<400> SEQUENCE: 3
catgagtgtg ctcactcagg tcctggsgtt g                                          31

<210> SEQ ID NO 4
<211> LENGTH: 33
<212> TYPE: DNA
<213> ORGANISM: Mus musculus

<400> SEQUENCE: 4
atgaggrccc ctgctcagwt tyttggmwtc ttg                                        33

<210> SEQ ID NO 5
<211> LENGTH: 30
<212> TYPE: DNA
<213> ORGANISM: Mus musculus

<400> SEQUENCE: 5
atggatttwc aggtgcagat twtcagcttc                                            30

<210> SEQ ID NO 6
<211> LENGTH: 29
<212> TYPE: DNA
<213> ORGANISM: Mus musculus

<400> SEQUENCE: 6
atgaggtkcy ytgytsayct yctctgrgg                                             29

<210> SEQ ID NO 7
<211> LENGTH: 32
<212> TYPE: DNA
<213> ORGANISM: Mus musculus

<400> SEQUENCE: 7
atgggcwtca aagatggagt cacakwyycw gg                                         32

<210> SEQ ID NO 8
<211> LENGTH: 31
<212> TYPE: DNA
<213> ORGANISM: Mus musculus

<400> SEQUENCE: 8

```
atgtggggay ctktttttycm mtttttcaat g                                          31

<210> SEQ ID NO 9
<211> LENGTH: 25
<212> TYPE: DNA
<213> ORGANISM: Mus musculus

<400> SEQUENCE: 9
atggtrtccw casctcagtt ccttg                                                  25

<210> SEQ ID NO 10
<211> LENGTH: 27
<212> TYPE: DNA
<213> ORGANISM: Mus musculus

<400> SEQUENCE: 10
atgtatatat gtttgttgtc tatttct                                                27

<210> SEQ ID NO 11
<211> LENGTH: 28
<212> TYPE: DNA
<213> ORGANISM: Mus musculus

<400> SEQUENCE: 11
atggaagccc cagctcagct tctcttcc                                               28

<210> SEQ ID NO 12
<211> LENGTH: 20
<212> TYPE: DNA
<213> ORGANISM: Mus musculus

<400> SEQUENCE: 12
actggatggt gggaagatgg                                                        20

<210> SEQ ID NO 13
<211> LENGTH: 27
<212> TYPE: DNA
<213> ORGANISM: Mus musculus

<400> SEQUENCE: 13
atgaaatgca gctggggcat sttcttc                                                27

<210> SEQ ID NO 14
<211> LENGTH: 26
<212> TYPE: DNA
<213> ORGANISM: Mus musculus

<400> SEQUENCE: 14
atgggatgga gctrtatcat sytctt                                                 26

<210> SEQ ID NO 15
<211> LENGTH: 27
<212> TYPE: DNA
<213> ORGANISM: Mus musculus

<400> SEQUENCE: 15
atgaagwtgt ggttaaactg ggttttt                                                27

<210> SEQ ID NO 16
<211> LENGTH: 25
<212> TYPE: DNA
<213> ORGANISM: Mus musculus
```

<400> SEQUENCE: 16
atgractttg ggytcagctt grttt                                    25

<210> SEQ ID NO 17
<211> LENGTH: 32
<212> TYPE: DNA
<213> ORGANISM: Mus musculus

<400> SEQUENCE: 17
atgggactcc aggcttcaat ttagttttcc tt                            32

<210> SEQ ID NO 18
<211> LENGTH: 29
<212> TYPE: DNA
<213> ORGANISM: Mus musculus

<400> SEQUENCE: 18
atggcttgtc yttrgsgctr ctcttctgc                                29

<210> SEQ ID NO 19
<211> LENGTH: 27
<212> TYPE: DNA
<213> ORGANISM: Mus musculus

<400> SEQUENCE: 19
atggratgga gckggrgtct ttmtctt                                  27

<210> SEQ ID NO 20
<211> LENGTH: 23
<212> TYPE: DNA
<213> ORGANISM: Mus musculus

<400> SEQUENCE: 20
atgagagtgc tgattctttt gtc                                      23

<210> SEQ ID NO 21
<211> LENGTH: 31
<212> TYPE: DNA
<213> ORGANISM: Mus musculus

<400> SEQUENCE: 21
atggmttggg tgtggamctt gcttattcct g                             31

<210> SEQ ID NO 22
<211> LENGTH: 28
<212> TYPE: DNA
<213> ORGANISM: Mus musculus

<400> SEQUENCE: 22
atgggcagac ttaccattct cattcctg                                 28

<210> SEQ ID NO 23
<211> LENGTH: 28
<212> TYPE: DNA
<213> ORGANISM: Mus musculus

<400> SEQUENCE: 23
atggattttg ggctgatttt ttttattg                                 28

<210> SEQ ID NO 24
<211> LENGTH: 27
<212> TYPE: DNA
<213> ORGANISM: Mus musculus

```
<400> SEQUENCE: 24
atgatggtgt taagtcttct gtacctg                                            27

<210> SEQ ID NO 25
<211> LENGTH: 21
<212> TYPE: DNA
<213> ORGANISM: Mus musculus

<400> SEQUENCE: 25
cagtggatag acagatgggg g                                                  21

<210> SEQ ID NO 26
<211> LENGTH: 21
<212> TYPE: DNA
<213> ORGANISM: Mus musculus

<400> SEQUENCE: 26
cagtggatag accgatgggg g                                                  21

<210> SEQ ID NO 27
<211> LENGTH: 21
<212> TYPE: DNA
<213> ORGANISM: Mus musculus

<400> SEQUENCE: 27
cagtggatga gctgatgggg g                                                  21

<210> SEQ ID NO 28
<211> LENGTH: 21
<212> TYPE: DNA
<213> ORGANISM: Mus musculus

<400> SEQUENCE: 28
caagggatag acagatgggg c                                                  21

<210> SEQ ID NO 29
<211> LENGTH: 17
<212> TYPE: DNA
<213> ORGANISM: Artificial Sequence
<220> FEATURE:
<223> OTHER INFORMATION: Contains sequences from Homo sapiens and Mus
      musculus

<400> SEQUENCE: 29
gttttcccag tcacgac                                                       17

<210> SEQ ID NO 30
<211> LENGTH: 21
<212> TYPE: DNA
<213> ORGANISM: Artificial Sequence
<220> FEATURE:
<223> OTHER INFORMATION: Contains sequences from Homo sapiens and Mus
      musculus

<400> SEQUENCE: 30
agcggataat ttcacacagg a                                                  21

<210> SEQ ID NO 31
<211> LENGTH: 42
<212> TYPE: DNA
<213> ORGANISM: Artificial Sequence
<220> FEATURE:
<223> OTHER INFORMATION: Contains sequences from Homo sapiens and Mus
      musculus
```

<210> SEQ ID NO 32
<211> LENGTH: 46
<212> TYPE: DNA
<213> ORGANISM: Artificial Sequence
<220> FEATURE:
<223> OTHER INFORMATION: Contains sequences from Homo sapiens and Mus
      musculus

<400> SEQUENCE: 32
ccgatgggcc cttggtggag gctgaggaga cggtgactga ggttcc                    46

<210> SEQ ID NO 33
<211> LENGTH: 43
<212> TYPE: DNA
<213> ORGANISM: Artificial Sequence
<220> FEATURE:
<223> OTHER INFORMATION: Contains sequences from Homo sapiens and Mus
      musculus

<400> SEQUENCE: 33
aagcttgccg ccaccatgaa gttgcctgtt aggctgttgg tgc                       43

<210> SEQ ID NO 34
<211> LENGTH: 42
<212> TYPE: DNA
<213> ORGANISM: Artificial Sequence
<220> FEATURE:
<223> OTHER INFORMATION: Contains sequences from Homo sapiens and Mus
      musculus

<400> SEQUENCE: 34
ggatccactc acgtttgatt tccagcttgg tccccccctcc ga                       42

<210> SEQ ID NO 35
<211> LENGTH: 111
<212> TYPE: PRT
<213> ORGANISM: Mus musculus

<400> SEQUENCE: 35

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val Ser Trp Val Arg Gln Pro Gly Lys Gly Leu Glu Trp Leu
        35                  40                  45

Gly Val Ile Trp Gly Asp Gly Ser Thr Asn Tyr His Pro Asn Leu Met
    50                  55                  60

Ser Arg Leu Ser Ile Ser Lys Asp Ile Ser Lys Ser Gln Val Leu Phe
65                  70                  75                  80

Lys Leu Asn Ser Leu Gln Thr Asp Asp Thr Ala Thr Tyr Tyr Cys Val
                85                  90                  95

Thr Leu Asp Tyr Trp Gly Gln Gly Thr Ser Val Thr Val Ser Ser
            100                 105                 110

<210> SEQ ID NO 36
<211> LENGTH: 112
<212> TYPE: PRT
<213> ORGANISM: Mus musculus -continued

<400> SEQUENCE: 36

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Phe Gln Thr
                85                  90                  95

Thr Tyr Val Pro Asn Thr Phe Gly Gly Gly Thr Lys Leu Glu Ile Lys
            100                 105                 110

<210> SEQ ID NO 37
<211> LENGTH: 131
<212> TYPE: PRT
<213> ORGANISM: Artificial Sequence
<220> FEATURE:
<223> OTHER INFORMATION: Contains sequences from Homo sapiens and Mus
      musculus

<400> SEQUENCE: 37

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Arg Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Leu Tyr Phe Cys
            100                 105                 110

Phe Gln Thr Thr Tyr Val Pro Asn Thr Phe Gly Gly Gly Thr Lys Leu
        115                 120                 125

Glu Ile Lys
    130

<210> SEQ ID NO 38
<211> LENGTH: 130
<212> TYPE: PRT
<213> ORGANISM: Artificial Sequence
<220> FEATURE:
<223> OTHER INFORMATION: Contains sequences from Homo sapiens and Mus
      musculus

<400> SEQUENCE: 38

Met Ala Val Leu Gly Leu Leu Phe Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu

```
                35                  40                  45
Ser Ser Tyr Gly Val Ser Trp Val Arg Gln Pro Pro Gly Lys Gly Leu
    50                  55                  60

Glu Trp Leu Gly Val Ile Trp Gly Asp Gly Ser Thr Asn Tyr His Pro
65                  70                  75                  80

Asn Leu Met Ser Arg Leu Ser Ile Ser Lys Asp Ile Ser Lys Ser Gln
                85                  90                  95

Val Leu Phe Lys Leu Asn Ser Leu Gln Thr Asp Thr Ala Thr Tyr
            100                 105                 110

Tyr Cys Val Thr Leu Asp Tyr Trp Gly Gln Gly Thr Ser Val Thr Val
            115                 120                 125

Ser Ser
    130

<210> SEQ ID NO 39
<211> LENGTH: 333
<212> TYPE: DNA
<213> ORGANISM: Mus musculus

<400> SEQUENCE: 39
caggtgcagc tgaaggagtc aggacctggc ctggtggcgc cctcacagag cctgtccatc      60
acatgcactg tctcagggtt ctcattaagc agctatggtg taagctgggt tcgccagcct     120
ccaggaaagg gtctggagtg gctgggagta atatggggtg acgggagcac aaattatcat     180
ccaaatctca tgtccagact gagtatcagc aaggatattt ccaagagcca agttctcttc     240
aaactgaata gtctgcaaac tgatgacaca gccacgtact actgtgtcac cttcgactac     300
tggggtcaag gaacctcagt caccgtctcc tca                                   333

<210> SEQ ID NO 40
<211> LENGTH: 336
<212> TYPE: DNA
<213> ORGANISM: Mus musculus

<400> SEQUENCE: 40
gatgttgtga tgacccaaac tccactctcc ctgcctgtca gtcttggaga tcaagcctcc      60
atctcttgca gatctagtca gagccttgta catagaaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tttgggactt tatttctgtt ttcaaactac atatgttccg     300
aacacgttcg gaggggggac caagctggaa ataaaa                                336

<210> SEQ ID NO 41
<211> LENGTH: 43
<212> TYPE: DNA
<213> ORGANISM: Mus musculus

<400> SEQUENCE: 41
aagcttgccg ccaccatgaa gttgcctgtt aggctgttgg tgc                        43

<210> SEQ ID NO 42
<211> LENGTH: 422
<212> TYPE: DNA
<213> ORGANISM: Artificial Sequence
<220> FEATURE:
<223> OTHER INFORMATION: Contains sequences from Homo sapiens and Mus
      musculus
```

<400> SEQUENCE: 42

```
aagcttgccg ccaccatgaa gttgcctgtt aggctgttgg tgctgatgtt ctggattcct      60
gcttccagca gtgatgttgt gatgacccaa actccactct ccctgcctgt cagtcttgga    120
gatcaagcct ccatctcttg cagatctagt cagagccttg tacatagaaa tggaaacacc    180
tatttacatt ggtacctgca gaagccaggc cagtctccaa agctcctgat ctacaaagtt    240
tccaaccgat tttctggggt cccagacagg ttcagtggca gtggatcagg gacagatttc    300
acactcaaga tcagcagagt ggaggctgag gatttgggac tttatttctg ttttcaagac    360
tacatatgtt ccgaacacgt tcggaggggg gaccaagctg gaaatcaaac gtgagtggat    420
cc                                                                    422
```

<210> SEQ ID NO 43
<211> LENGTH: 42
<212> TYPE: DNA
<213> ORGANISM: Mus musculus

<400> SEQUENCE: 43

```
ggatccactc acgtttgatt tccagcttgg tcccccctcc ga                        42
```

<210> SEQ ID NO 44
<211> LENGTH: 42
<212> TYPE: DNA
<213> ORGANISM: Mus musculus

<400> SEQUENCE: 44

```
aagctttccg ccaccatggc tgtcctgggg ctgctcttct gc                        42
```

<210> SEQ ID NO 45
<211> LENGTH: 427
<212> TYPE: DNA
<213> ORGANISM: Artificial Sequence
<220> FEATURE:
<223> OTHER INFORMATION: Contains sequences from Homo sapiens and Mus
      musculus

<400> SEQUENCE: 45

```
aagcttgccg ccaccatggc tgtcctgggg ctgctcttct gcctggtgac attcccaagc      60
tgtgtcctgt cccaggtgca gctgaaggag tcaggacctg gcctggtggc gccctcacag    120
agcctgtcca tcacatgcac tgtctcaggg ttctcattaa gcagctatgg tgtaagctgg    180
gttcgccagc ctccaggaaa gggtctggag tggctgggag taatatgggg tgacgggagc    240
acaaattatc atccaaatct catgtccaga ctgagtatca gcaaggatat ttccaagagc    300
caagttctct tcaaactgaa tagtctgcaa actgatgaca cagccacgta ctactgtgtc    360
accttggact actggggtca aggaacctca gtcaccgtct cctcagcctc caccaagggc    420
ccatcgg                                                              427
```

<210> SEQ ID NO 46
<211> LENGTH: 46
<212> TYPE: DNA
<213> ORGANISM: Mus musculus

<400> SEQUENCE: 46

```
ccgatgggcc cttggtggag gctgaggaga cggtgactga ggttcc                    46
```

<210> SEQ ID NO 47
<211> LENGTH: 112
<212> TYPE: PRT

<213> ORGANISM: Artificial Sequence
<220> FEATURE:
<223> OTHER INFORMATION: Contains sequences from Homo sapiens and Mus
      musculus

<400> SEQUENCE: 47

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Phe Gln Thr
                85                  90                  95

Thr Tyr Val Pro Asn Thr Phe Gly Gly Gly Thr Lys Leu Glu Ile Lys
            100                 105                 110

<210> SEQ ID NO 48
<211> LENGTH: 111
<212> TYPE: PRT
<213> ORGANISM: Artificial Sequence
<220> FEATURE:
<223> OTHER INFORMATION: Contains sequences from Homo sapiens and Mus
      musculus

<400> SEQUENCE: 48

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Asn Leu Met
    50                  55                  60

Ser Arg Leu Ser Ile Ser Lys Asp Ile Ser Lys Ser Gln Val Leu Phe
65                  70                  75                  80

Lys Leu Asn Ser Leu Gln Thr Asp Asp Thr Ala Thr Tyr Tyr Cys Val
                85                  90                  95

Thr Leu Asp Tyr Trp Gly Gln Gly Thr Ser Val Thr Val Ser Ser
            100                 105                 110

<210> SEQ ID NO 49
<211> LENGTH: 27
<212> TYPE: DNA
<213> ORGANISM: Artificial Sequence
<220> FEATURE:
<223> OTHER INFORMATION: Derived from Mus musculus

<400> SEQUENCE: 49
aactggaaga attcgcggcc gcaggaa                                                27

<210> SEQ ID NO 50
<211> LENGTH: 11
<212> TYPE: DNA
<213> ORGANISM: Artificial Sequence
<220> FEATURE:
<223> OTHER INFORMATION: Derived from Mus musculus

<400> SEQUENCE: 50
ccgccrccag g                                                                   11

<210> SEQ ID NO 51
<211> LENGTH: 15
<212> TYPE: DNA
<213> ORGANISM: Artificial Sequence
<220> FEATURE:
<223> OTHER INFORMATION: Derived from Mus musculus
<220> FEATURE:
<221> NAME/KEY: misc_feature
<222> LOCATION: (11)..(11)
<223> OTHER INFORMATION: n is a, c, g, or t

<400> SEQUENCE: 51
yyyyyyyyyy ncagg                                                               15

<210> SEQ ID NO 52
<211> LENGTH: 6
<212> TYPE: PRT
<213> ORGANISM: Artificial Sequence
<220> FEATURE:
<223> OTHER INFORMATION: Derived from Mus musculus

<400> SEQUENCE: 52

Ser Tyr Gly Val Ser Trp
1               5

<210> SEQ ID NO 53
<211> LENGTH: 16
<212> TYPE: PRT
<213> ORGANISM: Artificial Sequence
<220> FEATURE:
<223> OTHER INFORMATION: Derived from Mus musculus

<400> SEQUENCE: 53

Val Ile Trp Gly Asp Gly Ser Thr Asn Tyr His Pro Asn Leu Met Ser
1               5                   10                  15

<210> SEQ ID NO 54
<211> LENGTH: 3
<212> TYPE: PRT
<213> ORGANISM: Artificial Sequence
<220> FEATURE:
<223> OTHER INFORMATION: Derived from Mus musculus

<400> SEQUENCE: 54

Leu Asp Tyr
1

<210> SEQ ID NO 55
<211> LENGTH: 27
<212> TYPE: DNA
<213> ORGANISM: Artificial Sequence
<220> FEATURE:
<223> OTHER INFORMATION: primer sequence

<400> SEQUENCE: 55
aactggaaga attcgcggcc gcaggaa                                                  27

<210> SEQ ID NO 56
<211> LENGTH: 11
<212> TYPE: DNA
<213> ORGANISM: Artificial Sequence
<220> FEATURE:
<223> OTHER INFORMATION: Kozak translation initiation site, consensus

```
    sequence

<400> SEQUENCE: 56
ccgccrccag g                                                         11

<210> SEQ ID NO 57
<211> LENGTH: 15
<212> TYPE: DNA
<213> ORGANISM: Artificial Sequence
<220> FEATURE:
<223> OTHER INFORMATION: Immunoglobulin splice acceptor site, consensus
      sequence
<220> FEATURE:
<221> NAME/KEY: misc_feature
<222> LOCATION: (11)..(11)
<223> OTHER INFORMATION: n is a, c, g, or t

<400> SEQUENCE: 57
yyyyyyyyyy ncagg                                                     15
```